US012805776B2

(12) United States Patent
Rogers et al.

(10) Patent No.: US 12,805,776 B2
(45) Date of Patent: Nov. 24, 2026

(54) WIRELESS, IMPLANTABLE CATHETER-TYPE OPTOELECTRONIC SYSTEM AND APPLICATIONS OF SAME

(71) Applicants: NORTHWESTERN UNIVERSITY, Evanston, IL (US); ANN AND ROBERT H. LURIE CHILDREN'S HOSPITAL OF CHICAGO, Chicago, IL (US)

(72) Inventors: John A. Rogers, Wilmette, IL (US); Wei Lu, Evanston, IL (US); Joseph M. Forbess, Evanston, IL (US); Zhi-Dong Ge, Evanston, IL (US)

(73) Assignees: NORTHWESTERN UNIVERSITY, Evanston, IL (US); ANN AND ROBERT H. LURIE CHILDREN'S HOSPITAL OF CHICAGO, Chicago, IL (US)

( * ) Notice: Subject to any disclaimer, the term of this patent is extended or adjusted under 35 U.S.C. 154(b) by 690 days.

(21) Appl. No.: 18/036,189

(22) PCT Filed: Nov. 10, 2021

(86) PCT No.: PCT/US2021/058705

§ 371 (c)(1),
(2) Date: May 10, 2023

(87) PCT Pub. No.: WO2022/103787

PCT Pub. Date: May 19, 2022

(65) Prior Publication Data

US 2024/0041363 A1 Feb. 8, 2024

Related U.S. Application Data

(60) Provisional application No. 63/112,011, filed on Nov. 10, 2020.

(51) Int. Cl.
*A61B 5/1455* (2006.01)
*A61B 5/00* (2006.01)
(Continued)

(52) U.S. Cl.
CPC .......... *A61B 5/1459* (2013.01); *A61B 5/0004* (2013.01); *A61B 5/0022* (2013.01);
(Continued)

(58) Field of Classification Search
CPC .................................................... A61B 5/1455
See application file for complete search history.

(56) References Cited

U.S. PATENT DOCUMENTS 4,684,245 A 8/1987 Goldring
9,339,221 B1 5/2016 Heaton, II et al.

FOREIGN PATENT DOCUMENTS

WO 2004026127 A1 4/2004
WO 2018022916 A1 2/2018

OTHER PUBLICATIONS

J. L. Kohl, et al., UVCS/SOHO empirical determinations of anisotropic velocity distributions in the solar corona. Astrophys J 501, L127-L131 (1998).

(Continued)

*Primary Examiner* — Marjan Fardanesh
(74) *Attorney, Agent, or Firm* — troutman pepper locke; Tim Tingkang Xia, Esq.

(57) ABSTRACT

The invention relates to an optoelectronic system. The optoelectronic system includes an optoelectronic probe operably attached to a target region of a subject; and an electronic module coupled with the optoelectronic probe for wireless, real-time, and continuous measurements of physiological information of the subj ect.

20 Claims, 31 Drawing Sheets

(51) Int. Cl.
*A61B 5/0215* (2006.01)
*A61B 5/026* (2006.01)
*A61B 5/1459* (2006.01)

(52) U.S. Cl.
CPC ............ *A61B 5/0215* (2013.01); *A61B 5/026* (2013.01); *A61B 5/14552* (2013.01); *A61B 5/4839* (2013.01); *A61B 5/6852* (2013.01); *A61B 2562/0247* (2013.01); *A61B 2562/12* (2013.01); *A61B 2562/164* (2013.01); *A61B 2562/166* (2013.01)

(56) References Cited

OTHER PUBLICATIONS

F. Scholkmann, et al., End-tidal CO2: An important parameter for a correct interpretation in functional brain studies using speech tasks. Neuroimage 66, 71-79 (2013).
Signs & Symptoms of Anemia in Horses. https://www.succeed-equine.com/, (Feb. 2014).
W. Bai, et al., Bioresorbable photonic devices for the spectroscopic characterization of physiological status and neural activity. Nature biomedical engineering 3, 644-654 (2019).
F. Bloos, K. Reinhart, Venous oximetry. Intensive Care Med 31, 911-913 (2005).
J. Frazier, Theory and clinical application of continuous fiberoptic central venous oximetry (scvo2) monitoring. Critical Care Marketing and Education, Edwards Lifesciences, (2009).
J. L. Waller, et al., Clinical evaluation of a new fiberoptic catheter oximeter during cardiac surgery. Anesth Analg 61, 676-679 (1982).
O. J. Liakopoulos, et al., An experimental and clinical evaluation of a novel central venous catheter with integrated oximetry for pediatric patients undergoing cardiac surgery. Anesth Analg 105, 1598-1604, table of contents (2007).
G. Marx, K. Reinhart, Venous oximetry. Curr Opin Crit Care 12, 263-268 (2006).
R. Pearse, A. Rhodes, "Mixed and central venous oxygen saturation" in Yearbook of Intensive Care and Emergency Medicine 2005 (Springer, 2005), pp. 592-602.
M. L. Landsman, et al., A fiberoptic reflection oximeter. Pflugers Archiv 373, 273-282 (1978).
B. Boville, et al., Irvine, Quick Guide to Pediatric Cardiopulmonary Care. (2011).
D. C. McGee, M. K. Gould, Preventing complications of central venous catheterization. New England journal of medicine 348, 1123-1133 (2003).
E. M. Kagel, G. M. Rayan, Intravenous catheter complications in the hand and forearm. Journal of Trauma and Acute Care Surgery 56, 123-127 (2004).
A. Bowdle, Vascular complications of central venous catheter placement: evidence-based methods for prevention and treatment. Journal of cardiothoracic and vascular anesthesia 28, 358-368 (2014).
H. S. Vats, Complications of catheters: tunneled and nontunneled. Advances in chronic kidney disease 19, 188-194 (2012).
C. Kornbau, et al., Central line complications. International Journal of Critical Illness and Injury Science 5, 170 (2015).
H. U. Chung, et al., Binodal, wireless epidermal electronic systems with in-sensor analytics for neonatal intensive care. Science 363, eaau0780 (2019).
K. Lee, et al., Mechano-acoustic sensing of physiological processes and body motions via a soft wireless device placed at the suprasternal notch. Nature biomedical engineering, 1-11 (2019).
S. Y. Heo, et al., Wireless, battery-free, flexible, miniaturized dosimeters monitor exposure to solar radiation and to light for phototherapy. Sci Transl Med 10, eaau1643 (2018).
X. Yu, et al., Skin-integrated wireless haptic interfaces for virtual and augmented reality. Nature 575, 473-479 (2019).
K. Kwon, et al., Miniaturized, light-adaptive, wireless dosimeters autonomously monitor exposure to electromagnetic radiation. Science Advances 5, eaay2462 (2019).
H. Zhang, et al., Wireless, battery-free optoelectronic systems as subdermal implants for local tissue oximetry. Science advances 5, eaaw0873 (2019).
J. Kim, et al., Miniaturized Battery-Free Wireless Systems for Wearable Pulse Oximetry. Adv Funct Mater 27, 1604373 (2017).
Y. Mendelson, B. D. Ochs, Noninvasive pulse oximetry utilizing skin reflectance photoplethysmography. IEEE Transactions on Biomedical Engineering 35, 798-805 (1988).
J. L. Reuss, Multilayer modeling of reflectance pulse oximetry. IEEE Trans Biomed Eng 52, 153-159 (2005).
E. D. Chan, et al., Pulse oximetry: understanding its basic principles facilitates appreciation of its limitations. Respiratory medicine 107, 789-799 (2013).
M. Nitzan, A. Romem, R. Koppel, Pulse oximetry: fundamentals and technology update. Medical Devices (Auckland, NZ) 7, 231 (2014).
P. Scott, in Oregon Medical Laser Center. (1999).
TEMD7000X01 datasheet. www.vishay.com Rev. 1.6, (Feb. 2015).
L. Wang, S. L. Jacques, Monte Carlo modeling of light transport in multi-layered tissues in standard C. The University of Texas, MD Anderson Cancer Center, Houston, 4-11 (1992).
A. N. Bashkatov, et al., Optical Properties of Skin, Subcutaneous, and Muscle Tissues: A Review. J Innov Opt Heal Sci 4, 9-38 (2011).
A. Bouchama, J. P. Knochel, Heat stroke. N Engl J Med 346, 1978-1988 (2002).
C. G. Crandall, T. E. Wilson, Human cardiovascular responses to passive heat stress. Comprehensive Physiology 5, 17-43 (2011).
P. G. Agache, et al., Mechanical properties and Young's modulus of human skin in vivo. Arch Dermatol Res 269, 221-232 (1980).
A. Kalra, et al., An overview of factors affecting the skins Youngs modulus. Journal of Aging Science, (2016).
A. B. Mathur, et al., Endothelial, cardiac muscle and skeletal muscle exhibit different viscous and elastic properties as determined by atomic force microscopy. J Biomech 34, 1545-1553 (2001).
P. Ingelmo, M. Barone, R. Fumagalli, Importance of monitoring in high risk surgical patients. Minerva Anestesiol 68, 226-230 (2002).
K. Reinhart, et al., Continuous central venous and pulmonary artery oxygen saturation monitoring in the critically ill. Intensive Care Med 30, 1572-1578 (2004).
R. M. McAdams, et al., Left ventricular hypertrophy is prevalent in Sprague□Dawley rats. Comparative medicine 60, 357-363 (2010).
S. E. Litwin, et al., Serial echocardiographic assessment of left ventricular geometry and function after large myocardial Infarction in the rat. Circulation 89, 345-354 (1994).
L. E. Watson, et al., Baseline echocardiographic values for adult male rats. Journal of the American Society of Echocardiography 17, 161-167 (2004).
J. Shin, et al., Bioresorbable pressure sensors protected with thermally grown silicon dioxide for the monitoring of chronic diseases and healing processes. Nat Biomed Eng 3, 37-46 (2019).
S. M. Won, et al., Multimodal Sensing with a Three-Dimensional Piezoresistive Structure. ACS Nano 13, 10972-10979 (2019).
S. R. Krishnan, et al., Epidermal electronics for noninvasive, wireless, quantitative assessment of ventricular shunt function in patients with hydrocephalus. Sci Transl Med 10, eaat8437 (2018).
R. C. Webb, et al., Epidermal devices for noninvasive, precise, and continuous mapping of macrovascular and microvascular blood flow. Sci Adv 1, e1500701 (2015).
Y. Zhang, et al., Battery-free, lightweight, injectable microsystem for in vivo wireless pharmacology and optogenetics. Proc Natl Acad Sci U S A 116, 21427-21437 (2019).
J. W. Jeong, et al., Wireless Optofluidic Systems for Programmable In Vivo Pharmacology and Optogenetics. Cell 162, 662-674 (2015).
J. Ahrens, B. Geveci, C. Law, Paraview: An end-user tool for large data visualization. The visualization handbook 717, (2005).
J. M. Stujenske, et al., Modeling the Spatiotemporal Dynamics of Light and Heat Propagation for In Vivo Optogenetics. Cell Rep 12, 525-534 (2015).

(56) References Cited

OTHER PUBLICATIONS

I. Baotic, et al., Isoflurane favorably modulates guanosine triphosphate cyclohydrolase-1 and endothelial nitric oxide synthase during myocardial ischemia and reperfusion injury in rats. Anesthesiology 123, 582-589 (2015).
Y. Liu, et al., Vascular endothelial growth factor regulation of endothelial nitric oxide synthase phosphorylation is involved in isoflurane cardiac preconditioning. Cardiovascular research 115, 168-178 (2019).
F. Fabbri, et al., Optical measurements of absorption changes in two-layered diffusive media. Phys Med Biol 49, 1183-1201 (2004).
Korean Intellectual Property Office (ISR/KR), "International Search Report for PCT/US2021/058705", Korea, Mar. 3, 2022.
Zhang, Hao et al., "Wireless, battery-free optoelectronic systems as subdermal implants for local tissue oximetry", Science Advances, Mar. 8, 2019 (Publication date), vol. 5, Article No. eaaw0873.
Kim, Jeonghyun et al., "Miniaturized battery-free wireless systems for wearable pulse oximetry", Advanced Functional Materials, Nov. 25, 2016 (Publication date), vol. 27, No. 1, Article No. 1604373.
Lu, Wei et al., "Wireless, implantable catheter-type oximeter designed for cardiac oxygen saturation", Science Advances, Feb. 10, 2021 (Publication date), vol. 7, Article No. eabe0579.

FIG. 4D
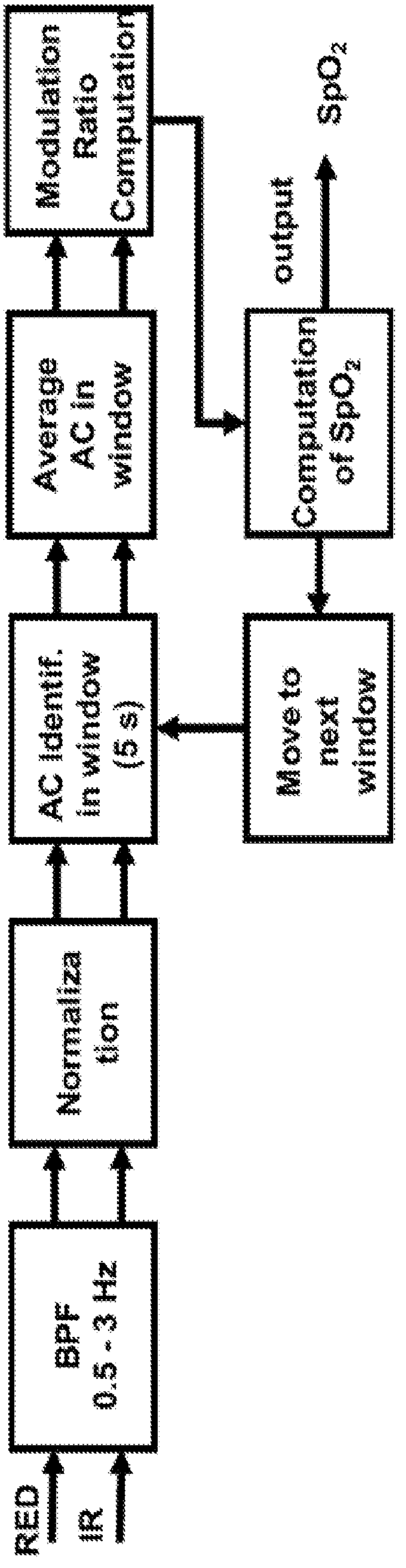
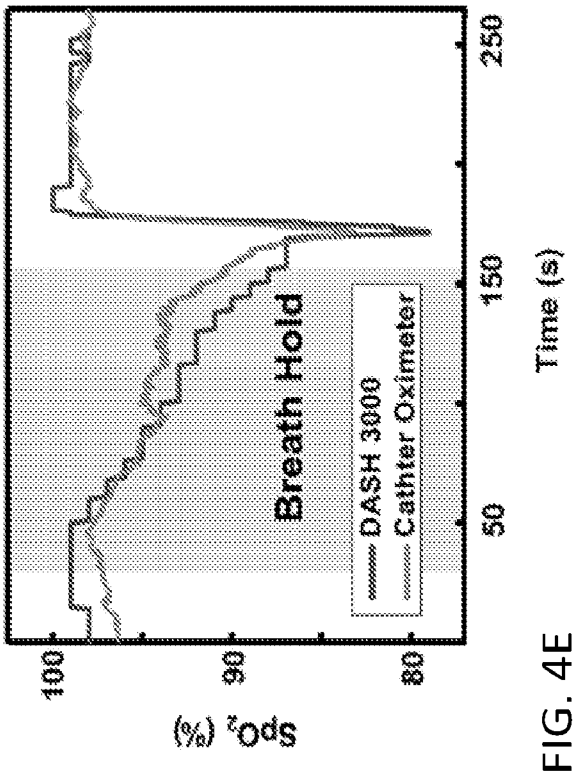
FIG. 4E
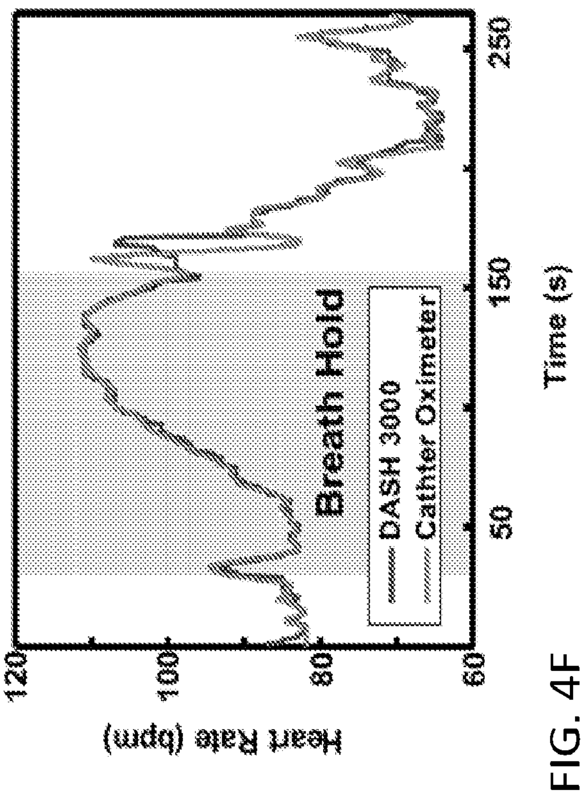
FIG. 4F

FIG. 5D
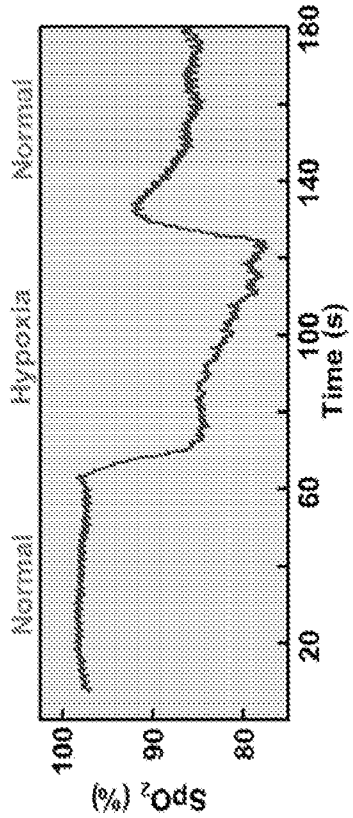
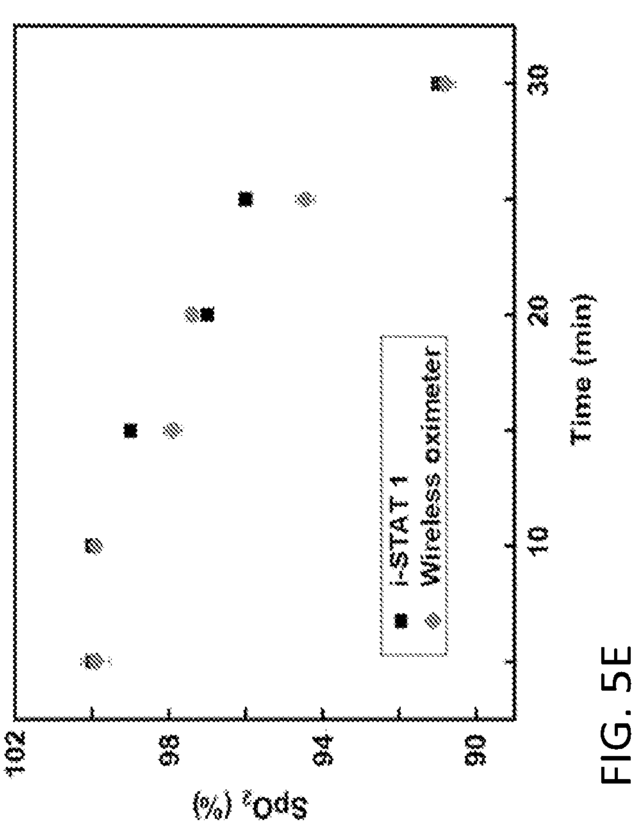
FIG. 5E
FIG. 5C
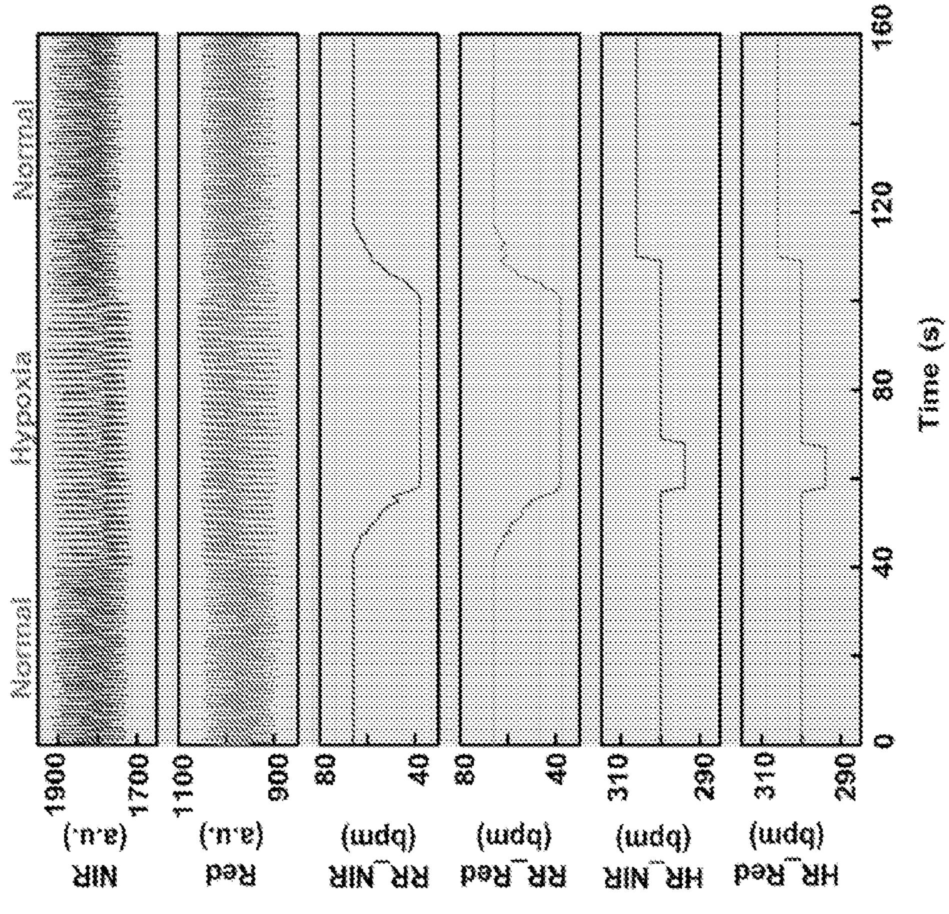

Red

NIR

WIRELESS, IMPLANTABLE CATHETER-TYPE OPTOELECTRONIC SYSTEM AND APPLICATIONS OF SAME

CROSS-REFERENCE TO RELATED PATENT APPLICATIONS

This application claims priority to and the benefit of U.S. Provisional Application Ser. No. 63/112,011, filed Nov. 10, 2020, which is incorporated herein by reference in its entirety.

FIELD OF THE INVENTION

The present invention relates generally to biosensors, and more particularly to wireless, implantable catheter-type oximeters designed for cardiac oxygen saturation and applications of same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

The cardiovascular system delivers oxygen and nutrients to tissues and cells in the body. Maintaining an adequate balance between oxygen delivery and consumption is essential for cellular physiological function. Accurate and real-time monitoring of specific intracardiac and major vascular oxygen saturations after open-heart surgery is critically important for treating patients, especially those who suffer from cyanotic congenital heart defects. The measurement of these saturations is, in fact, performed during diagnostic cardiac catheterization to calculate cardiac output and derive vascular resistances. In the intensive care unit (ICU) setting, the intravenous fiber optic oximetric catheter is used to monitor continuously blood oxygen saturation, obtained either as mixed venous oxygen saturation ($SvO_2$, a reflection of the global balance between oxygen delivery and consumption as it is measured in the pulmonary artery), or as central venous oxygen saturation ($ScvO_2$, a reflection of regional oxygen extraction from the brain and the upper part of the body as it is measured from a central vein).

Existing fiber optic catheter oximeters use hard glass fiber waveguides to deliver light from an external source to the blood at the tip of the catheter, and to transmit some fraction of the backscattered light back to an external unit for detection. Here, the fiber optic catheter connects to a light source and sensing module and an additional interface joins the system to an apparatus that contains processing and driving circuits, display monitor and controlling software. The complete system provides an effective tool for monitoring venous oxygenation via insertion of the catheter probe through a vein to a desired location, but it tethers the patient to bedside hardware, thereby limiting their freedom of movement and complicating the simultaneous use of other diagnostic or therapeutic tools. Moreover, the rigid properties of the glass fiber can induce adverse events during long-term implantation, e.g. damage to blood vessels, infection, or thrombosis. For all patients who receive catheters, mechanical complications are reported to occur in 5 to 19 percent of patients, infectious complications in 5 to 26 percent, and thrombotic complications in 2 to 26 percent. These complications are particularly frequent and severe in infants and children. An unmet clinical need is in alternative type of oximeter designed to provide real-time, accurate intravascular oxygen saturation yet avoid adverse effects that can occur in these and other high-risk patients.

Therefore, a heretofore unaddressed need exists in the art to address the aforementioned deficiencies and inadequacies.

SUMMARY OF THE INVENTION

In light of the foregoing, one of the objectives of this invention is to provide a thin, flexible catheter-type optoelectronic probe that connects to a small, wearable electronic module for wireless, real-time, and continuous measurements of intravascular oxygen saturation with clinical-grade accuracy, thereby overcoming the aforementioned challenges in cardiovascular monitoring. The probe tip in some embodiments includes high-performance, miniaturized light-emitting diodes and photodiode, fully encapsulated with medical-grade, soft, transparent silicone elastomer. The electronic module supports rechargeable powering, circuit control, signal processing, and wireless data communication based on Bluetooth protocols. A graphical user interface deployed on a smartphone or tablet computer or ICU monitoring display enables real-time visualization, storage, and analysis of measurement data. The absence of physical tethers, the soft, biocompatible construction of the probe, and the lateral (as opposed to distal) configuration of the measurement represent key defining features. The invention presents potentially important advances in wireless optoelectronic technologies for cardiovascular care.

This invention in one aspect discloses an optoelectronic system. The optoelectronic system comprises an optoelectronic probe operably attached onto a target region of a subject; and an electronic module coupled with the optoelectronic probe for wireless, real-time, and continuous measurements of physiological information of the subject. The target region can be target tissues, a surface of a desired organ, and/or regions in proximity to an organ surface. In one embodiment, the physiological information comprises a tissue oxygenation, a heart rate (HR), a respiration rate (RR), and/or a temperature.

In one embodiment, the optoelectronic probe comprises a low modulus, flexible catheter with a probe tip comprising an optoelectronic sensor mounted onto a flexible printed circuit board (fPCB) in a geometry of a narrow, thin strip that detachably and electrically connects to the electronic module.

In one embodiment, the narrow, thin strip has a width in a range of about 0.5-2 mm, a thickness in a range of about 50-180 μm, and a length in a range of about 5-20 mm.

In one embodiment, the fPCB comprises a flexible substrate and conductive traces, pads and outline defined on the flexible substrate. In one embodiment, the flexible substrate is formed of a flexible material.

In one embodiment, the optoelectronic sensor comprises optical stimulation and sensing components, and optical blocking modules.

In one embodiment, the optical stimulation and sensing components comprise at least two light-emitting diodes (LEDs) and at least one photodiode (PD).

In one embodiment, the at least two LEDs and the at least one PD are surface mount (SMT) electronic components that are placed and attached onto the fPCB using reflow soldering.

In one embodiment, the at least two LEDs comprises a red LED with a peak emission wavelength in a range of about 600-700 nm and an infrared LED with a peak emission wavelength in a range of about 850-1050 nm.

In one embodiment, the optoelectronic probe further comprises one or more LEDs with peak emission wavelengths different from that of the red LED and the IR LED for additional measurement capabilities.

In one embodiment, the optical stimulation and sensing components are arranged in a lateral configuration such that the LEDs have divergent and lateral emission features that maximize light-tissue coupling for a range of implantation sites including blood vessel and cardiac tissue.

In one embodiment, the at least two LEDs are positioned laterally to a long axis of the probe.

In one embodiment, the PD is positioned to be equidistant to the two LEDs at a distance selected to balance sensing depth, probing volume, and signal to noise ratio.

In one embodiment, the probe volume and probe depth are operably adjusted through control over of light intensity of the LEDs and the distance between the LEDs and PD, to allow optimization for measurements of localized tissue oximetry on different sites of interest. In one embodiment, the distance is in a range of about 1-3 mm.

In one embodiment, the optical blocking modules comprise at least two light-blocking structures for eliminating parasitic transmission of light from the LEDs directly to the PD without passing through surrounding tissues of interest.

In one embodiment, at least two light-blocking structures comprise two opaque silicone-based cuboid structures.

In one embodiment, one of the light-blocking structures is positioned between the PD and one side of the LEDs, and the other of the light-blocking structures is positioned at the probe tip close to the other side of the LEDs.

In one embodiment, a small plug-in connector serves as an electrical interface between the optoelectronic probe and the electronic module and allows battery recharge using a wired interface.

In one embodiment, a medical-grade, biocompatible silicone fully encapsulates the optoelectronic probe to define the low modulus, flexible catheter having a cylindrical shape and smooth surface that facilitates surgical manipulation and insertion.

In one embodiment, the low modulus, flexible catheter has a diameter in a range of about 0.5-2 mm.

In one embodiment, the optoelectronic probe is a catheter-type oximetry sensor.

In one embodiment, the optoelectronic probe further comprises sensors for measuring pressure and flow, and/or means for drug delivery.

In one embodiment, the electronic module is a bendable, miniaturized, battery-powered electronic module adapted for rechargeable powering, circuit control, signal processing, and wireless data communication.

In one embodiment, the electronic module comprises a fPCB, electronic components mounted onto the fPCB, and a battery module coupled with the electronic components, which are disposed between a bottom encapsulation layer and a top encapsulation layer.

In one embodiment, the electronic components comprises a wireless controller for performing data sampling, controlling the LEDs in low duty cycle mode, executing data processing and operating wireless communications.

In one embodiment, the wireless communications use at least one communication protocol of near field communication (NFC), Wi-Fi/Internet, Bluetooth, Bluetooth low energy (BLE), and Cellular communication protocols.

In one embodiment, the battery module comprises at least one battery. In one embodiment, the at least one battery is rechargeable.

In one embodiment, the optoelectronic system further comprises a customized app with a graphical user interface deployed on an external device that enables real-time visualization, storage, and analysis of measured data, wherein the graphical user interface provides a control interface to the optoelectronic system.

In one embodiment, the external device is a mobile device, a computer, or an ICU monitoring display.

In one embodiment, the optoelectronic system is mechanically compliant and water resistant.

In one embodiment, the optoelectronic system is devoid of physical tethers.

In one embodiment, the optoelectronic system is configured to measure changes in heart rate, respiration rate, ischemia, and arrhythmias.

In one embodiment, the optoelectronic system is useable for monitoring intravascular or intracardiac oxygen saturation at home or in a surgical operation.

In another aspect, the invention relates to a method of fabricating an optoelectronic system. The method includes forming a low modulus, flexible catheter-type optoelectronic probe; and assembling an electronic module detachably and electrically connected to the optoelectronic probe for wireless, real-time, and continuous measurements of physiological information of the subject.

In one embodiment, said forming the catheter-type optoelectronic probe comprises providing a fPCB comprising a flexible substrate and conductive traces, pads and outline defined on the flexible substrate; attaching an optoelectronic sensor onto the fPCB using reflow soldering with low-temperature solder paste to form a sensing module; connecting the sensing module to a detachable connector through a plurality of conductive wires with a desired length; placing the sensing module and the conductive wires into a flexible tube; injecting a biocompatible silicone prepolymer into the flexible tube, and curing the injected silicone prepolymer in a period of time; and removing the flexible tube to form the comprises the low modulus, flexible catheter-type optoelectronic probe.

In one embodiment, the optoelectronic sensor comprises SMT electronic components comprising a red LED, an infrared LED, and a PD.

In one embodiment, the red and infrared LEDs are positioned laterally to a long axis of the probe, wherein the PD is positioned to be equidistant to the red and infrared LEDs at a distance selected to balance sensing depth, probing volume, and signal to noise ratio.

In one embodiment, the optoelectronic sensor further comprises at least two light-blocking structures, wherein one of the light-blocking structures is positioned between the PD and one side of the red and infrared LEDs, and the other of the light-blocking structures is positioned at the probe tip close to the other side of the red and infrared LEDs.

In one embodiment, the electronic module comprises a fPCB, electronic components mounted onto the fPCB, and a battery module coupled with the electronic components.

In one embodiment, the electronic components comprises a wireless microcontroller.

In one embodiment, said providing the electronic module comprises providing a first layer of a flexible material formed in a mold and a second layer of the flexible material formed on a glass slide, served as a top encapsulation layer and a battom encapsulation layer, respectively; placing the electronic module into the first layer, pouring a solution of soft silicone to fill voids in between electronics and the first layer, and attaching the glass slide with the second layer defined a surface for a skin interface, and clamping them together to form an assembly; curing the assembly to complete encapsulation; and cutting the cured assembly to define a smooth perimeter boundary for the optoelectronic system and openings for detachable and electrical connection to the optoelectronic probe.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

FIG. 1A: Schematic illustration of the use of an implanted device for wireless blood oximetry near the cardiac surface. The system includes a catheter-type oximeter with sensing tip sutured onto the surface of the heart, interfaced to an electronic module that attaches to the skin for signal collection and wireless data transmission through Bluetooth protocols. A custom GUI displays and records the data on a computer, and serves as a control interface to the device. FIG. 1B: Exploded view schematic illustration of the device design. The electronic module contains five layers: a bottom elastomeric substrate, a flexible PCB, a collection of electronic components, a lithium ion battery, and a top elastomeric encapsulation. FIG. 1C: Exploded view schematic illustration of the device design. The enlarged image shows the sensor probe, which includes a flexible PCB, optical stimulation and sensing components, optical blocking modules. The probe has a diameter of 1.5 mm and is fully encapsulated with transparent, bio-compatible silicone. FIG. 1D: Image of a catheter oximeter wrapped around a glass rod. FIG. 1E: Image of an electronic module without encapsulation. FIG. 1F: Image of a catheter-type oximetry sensor. FIG. 1G: Schematic block diagram of the system.

FIG. 2A: Spectral properties of light emission from the red and near-infrared (NIR) LEDs used for the sensor probe. These LEDs (peak wavelengths of 645 nm and 950 nm) cover the parts of the spectrum of reversed absorption properties for deoxygenated hemoglobin [Hb] and oxygenated hemoglobin [$HbO_2$]. FIG. 2B: Measured photocurrent as a function of input current for red and NIR LEDs, with the sensor probe implanted into raw meat. The experimental setup appears in FIGS. 8A-8B. FIG. 2C: Monte Carlo simulation of the spatial distribution of normalized emission intensity profiles from the NIR and Red LEDs in cardiac tissue. FIG. 2D: Thermal image showing the temperature distribution of the skin of an adult arm with a catheter probe placed on top. FIG. 2E: Measured temperature of the oximeter sensor probe during operation, with activation at 1 min and deactivation at 4 min. The sensor induces minimal increase in temperature (less than 0.08° C.). FIG. 2F: Measured photovoltage output from the amplifier circuit as a function of time during a driving clock sequence of red and NIR LEDs, and ADC sampling. Narrowing the driving pulses for the LEDs effectively reduces the power consumption and prolongs battery lifetime. FIG. 2G: Battery voltage as a function of working time. A 45 mAh lithium battery supports operation for at least 22 hours.

FIG. 3A: Measured Young's moduli for 3 catheter probes (inset images, scale bar is 2 cm) encapsulated with 3 different biocompatible silicone elastomers (labeled: MED-1040, MED-1000, and MED-1037, respectively). The Young's moduli of the 3 catheter probes ranges from 800 kPa to 1700 kPa. FIG. 3B: Measured bending stiffness for the 3 catheter probes in FIG. 3A, a catheter probe fabricated from relative stiff copper wire encapsulated with MED-1000, and a commercial fiber optic catheter (Swan Ganz 777F8, Edwards Inc.). The bending stiffness are 1.6, 1.8, 2.3, 20 and 243 $N/mm^2$ respectively. FIG. 3C: Finite element modeling of the sensor probe and catheter subjected to a bending radius of 22 mm and 27 mm, respectively. FIG. 3D: Measured photovoltage from the catheter probe as a function of cycles of compression and bending. Experimental details appear in FIGS. 12-13. The photovoltage generated from the photodetector corresponds to operation of the two LEDs (peak wavelengths 645 nm and 950 nm, respectively) at the tip of the catheter probe. FIG. 3E: Measured photovoltage as a function of immersion time in phosphate-buffered saline (PBS) solution at 37° C. Experimental details appear in FIGS. 15 and 16A-16B. The data indicate negligible change in performance over 8 weeks. FIG. 3F: CT image of the catheter sensor after 2 weeks of implantation. FIGS. 3G-3H: Analysis of complete blood count (FIG. 3G) and blood chemistry (FIG. 3H) for mice with an oximetry probe implanted subcutaneously for 30 days (labeled as Experiment) and for mice without device implantation (labeled as Control). Abbreviations and corresponding units include, WBC: white blood cell (K/μL), RBC: red blood cell (M/μL), HGB: blood hemoglobin level (g/dL), HCT: hematocrit level (%), MCV: mean corpuscular volume (fL), MCH: mean corpuscular hemoglobin (pg), RDW: red cell distribution width (%), PLT: platelet count in blood (L/μL), GLU: glucose (mg/dL), TRIG: triglycerides (mg/dL), ALT: alanine aminotransferase (U/L), AST: aspartate transaminase (IU/L), ALP: alkaline phosphatase (IU/L), CHOL: cholesterol (mg/dL), PHOS: phosphorus (mg/dL), CAL: calcium (mg/dL). Additional blood count and blood chemistry experiment results are presented in FIGS. 18A-18B.

FIGS. 4A-4H show performance characteristics for oximetry measurements of the wireless catheter oximeter, according to embodiments of the invention. FIG. 4A: Comparisons of light emission profiles of a commercial catheter oximeter (Swan Ganz 777F8, Edwards, Inc) and the device introduced here. FIG. 4B: Comparisons of the commercial catheter oximeter and the device introduced here in measuring the oxygen saturation in blood solutions with different ratios of HbO and Hb. The inset image shows the comparison of wireless catheter probe and the commercial fiber optic catheter (scale bar is 1 cm). FIG. 4C: Measured pulse signals from the device placed on the index finger of an adult. FIG. 4D: Algorithm flow chart of the calculation of pulse oximetry based on photovoltage signals. FIGS. 4E-4F: Measured $SpO_2$ (FIG. 4E) and heart rate (FIG. 4F) during a period of rest followed by a breath hold and then another period of rest. The result match those obtained with a commercial oximeter (General Electronic, Inc). The results of additional experiments appear in FIG. 22. FIG. 4G: Bland-Altman plot of $SpO_2$ from finger (four subjects, 801 points). FIG. 4H: Bland-Altman plot of HR from finger (4 subjects, 801 points).

FIGS. 5A-5E show in-vivo demonstration for real-time monitoring of cardiac physiology in a rodent model, according to embodiments of the invention. FIG. 5A: 3D schematic illustration of the placement of the catheter oximeter around the heart of a rat with the wireless module placed on the back. FIG. 5B: Signal waveform captured with this system. Modifying the settings associated with the ventilator that supports respiration provides access to different cardiac conditions (labeled as Normal, Hypoxia, and Arrhythmia). FIG. 5C: Measurements of cardiac activity (beating patterns, heart rate, and respiration rate). FIG. 5D: Measured oxygenation of the heart. Induced changes in cardiac pulse oximetry ($SpO_2$) match well with the changes on ventilator machine. FIG. 5E: Measured cardiac oxygenation using the wireless catheter oximeter and using a commercial blood gas analyzer. The analyzer measures blood sampled from left ventricle, while the wireless the catheter oximeter measures the oxygen saturation from the heart surface immediately after collecting blood samples.

FIG. 7A: Relative spectral sensitivity vs. wavelength. FIG. 7B: Measured photocurrent from the photodiode at the sensing probe as a function of time for illumination with light after passing through a chopper (red light, wavelength: 633 nm; optical power: 4 mW).

FIG. 8A: Test platform for measuring NIR and RED LED optical responses, for FIG. 2B. FIG. 8B: Test platform for measuring the thermal characteristics of the catheter oximeter probe, for FIG. 2E.

FIG. 9A: Light intensity decay from catheter/muscle boundary, along the z-axis right on top of red LED and NIR LED respectively. FIG. 9B: The illumination volume in cardiac tissue for red and NIR LEDs as a function of irradiance threshold. FIG. 9C: Light penetration depth in tissue as a function of LED irradiance, for threshold 0.01 $mW/mm^2$. FIG. 9D: Light illumination volume in tissue as a function of LED irradiance, for threshold of 0.01 $mW/mm^2$.

FIG. 10A: Temperature change distribution in the ZX plane at the middle (Y=0 mm) of the Red and NIR LEDs. FIG. 10B: Temperature change distribution in the ZY plane at the middle (X=0.3 mm) of the Red LEDs. FIG. 10C: Temperature change distribution in the ZY plane at the middle (X=−0.3 mm) of the NIR LED. FIG. 10D: Temperature change distribution as a function of time of four representative points (FIGS. 10A-10D) in proximity with the LEDs. Maximum temperature change based on FEA is 0.2° C.

FIG. 11A: MED-1040. FIG. 11B: MED-1000. FIG. 11D: MED-1037.

FIG. 13A: Red pulse signal in THE different stretch cycles. FIG. 13B: NIR LED pulse signal in THE different stretch cycles.

FIG. 20A: Image shows the fiber optic catheter and the monitoring machine (Edwards). FIG. 20B: In vitro test of calculated blood oxygen saturation derived from measurements with a wireless catheter oximeter, with comparison to measurements performed with a commercial fiber optic oximeter (Swan Ganz 777F8, and HemoSphere advanced monitoring platform).

FIG. 21A: Measurement method of using the wireless catheter oximeter to measure global pulse oximetry. During measurement, the probe is fully covered by the finger. FIG. 21B: A clinical standard pulse oximeter, GE DASH 3000, used in this comparison experiment.

FIG. 23A: Animal experiment set up, including an adult female rat under surgery, wireless catheter oximeter, small animal ventilator (Braintree Scientific Inc.), rodent pulse oximeter (MouseSTAT Jr., Kent Scientific Corporation), blood gas analyzer. FIG. 23B: The blood gas analyzer (VetScan i-STAT 1, Abaxis, Inc.) and the cartridge used in this experiment.

DETAILED DESCRIPTION OF THE INVENTION

Figure 1A:
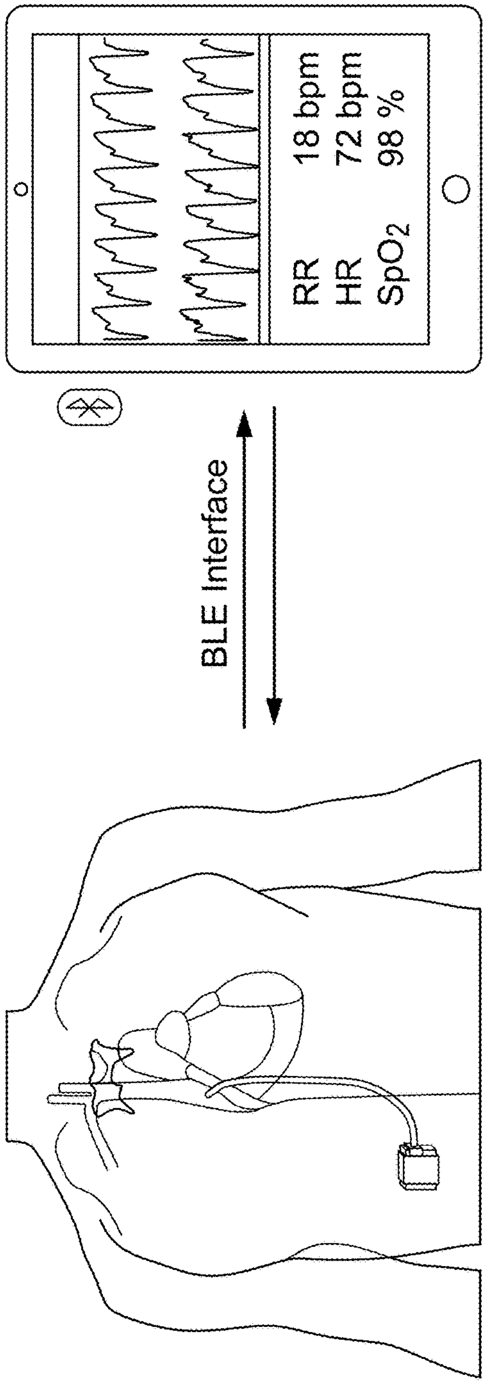
FIGS. 1A-1G show implantable, wireless catheter oximeter for real-time monitoring of cardiac physiology in the context of surgical procedures, according to embodiments of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout. The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of "a", "an", and "the" includes plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising", or "includes" and/or "including", or "has" and/or "having", or "carry" and/or "carrying", or "contain" and/or "containing", or "involve" and/or "involving", "characterized by", and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in the disclosure, the phrase "at least one of A, B, and C" should be construed to mean a logical (A or B or C), using a non-exclusive logical OR. As used herein, the term "and/or" includes any and all combinations of one or more of the associated listed items.

As used in the disclosure, the term "bidirectional wireless communication system" refers to onboard components of sensors, wireless controller and other electronic components that provides capability of receiving and sending signals using at least one communication protocol of near field communication (NFC), Wi-Fi/Internet, Bluetooth, Bluetooth low energy (BLE), and Cellular communication protocols for wireless communication. In this manner, an output may be provided to an external device, including a cloud-based device, personal portable device, or a caregiver's computer system. Similarly, a command may be sent to the sensor, such as by an external controller, which may or may not correspond to the external device. Machine learning algorithms may be employed to improve signal analysis and, in turn, command signals sent to the medical sensor, including a stimulator of the medical sensor for providing haptic signal to a user of the medical device useful in a therapy. More generally, these systems may be incorporated into a processor, such as a microprocessor located on-board or physically remote from the electronic device of the medical sensor. An example of the wireless controller is a near field communication (NFC) chip, including NFC chips. NFC is a radio technology enabling bi-directional short range wireless communication between devices. Another example of a wireless controller is a Bluetooth® chip, or a BLE system-on-chip (SoC), which enables devices to communicate via a standard radio frequency instead of through cables, wires or direct user action.

The term "flexibility" or "bendability", as used in the disclosure, refers to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and open or mesh geometries.

The term "bending stiffness" refers to a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The terms "Young's modulus" and "modulus" are used interchangeably and refer to a mechanical property of a material, device or layer which refers to the ratio of stress to strain for a given substance. Young's modulus may be provided by the expression;

$$E = \frac{(\text{stress})}{(\text{strain})} = \left(\frac{L_0}{\Delta L}\right)\left(\frac{F}{A}\right),$$

where E is Young's modulus, $L_0$ is the equilibrium length, $\Delta L$ is the length change under the applied stress, F is the force applied and A is the area over which the force is applied. Young's modulus may also be expressed in terms of Lame constants via the equation:

$$E = \frac{\mu(3\lambda + 2\mu)}{\lambda + \mu}$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably 10 times larger for some applications, more preferably 100 times larger for other applications and even more preferably 1000 times larger for yet other applications. "Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material.

The term "elastomer", as used in the disclosure, refers to a polymeric material which can be stretched or deformed and return to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers useful include, but are not limited to, thermoplastic elastomers, styrenic materials, olefenic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to, silicon containing polymers such as polysiloxanes including poly (dimethyl siloxane) (i.e. PDMS and h-PDMS), poly(methyl siloxane), partially alkylated poly(methyl siloxane), poly (alkyl methyl siloxane) and poly(phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In one embodiment, a flexible polymer is a flexible elastomer.

The term "encapsulate" or "encapsulation", as used in the disclosure, refers to the orientation of one structure such that it is at least partially, and in some cases completely, surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. The invention includes devices having partially or completely encapsulated electronic devices, device components and/or inorganic semiconductor components.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Accurate, real-time monitoring of intravascular oxygen levels can be a crucial aspect of tracking the cardiopulmonary health of patients after open-heart surgery. Existing technologies use intravascular placement of glass fiber optic probes which can expose patients to the usual risks of blood vessel damage, thrombosis and infection, associated with indwelling catheters. In addition, the physical tethers that connect currently utilized probes to external light sources, detectors, and data acquisition hardware limit freedom of movement and add clutter to the intensive care unit (ICU) environment.

In view of the foregoing, the invention discloses an alternative oximeter technology that avoids these disadvantages through the application of a miniaturized, implantable optoelectronic catheter that incorporates light emitting and detecting components on the probe itself, encapsulated by soft biocompatible materials. A small, skin-interfaced module serves as a wireless interface to a tablet computer that continuously displays oxygen saturation, as well as cardiac and respiratory activity. In vitro and in vivo testing shows that this platform offers measurement accuracy and precision equivalent to those of clinically used pulse oximeter and clinical fiber optic technologies for pulse oximetry, heart rate and for intravascular oximetry, with results that match values determined with a blood gas analyzer. These findings establish the foundations of advanced wireless technology for monitoring specific intracardiac oxygenation saturation following cardiothoracic surgery.

Referring to FIGS. 1A-1G, the optoelectronic system in one embodiment is a wireless, flexible catheter-type oximeter. The optoelectronic system comprises an optoelectronic probe operably attached onto a target region of a subject, such as the heart; and an electronic module coupled with the optoelectronic probe for wireless, real-time, and continuous measurements of physiological information of the subject. The target region can be target tissues, a surface of a desired organ, and/or regions in proximity to an organ surface. The physiological information comprises, but is not limited to, a tissue oxygenation level, a heart rate (HR), a respiration rate (RR), and/or a temperature.

In some embodiments, the optoelectronic probe comprises a low modulus, flexible catheter with a probe tip comprising an optoelectronic sensor mounted onto a flexible printed circuit board (fPCB) in a geometry of a narrow, thin strip that detachably and electrically connects to the electronic module. In one embodiment, the narrow, thin strip has a width in a range of about 0.5-2 mm, a thickness in a range of about 50-180 μm, and a length in a range of about 5-20 mm.

In some embodiments, the fPCB comprises a flexible substrate and conductive traces, pads and outline defined by, for example, patterned ablation of the copper using a UV laser system, on the flexible substrate. In one embodiment, the flexible substrate is formed of a flexible material. On embodiment of the flexible material includes, is not limited to, a medical-grade, soft, transparent silicone elastomer.

In some embodiments, the optoelectronic sensor comprises optical stimulation and sensing components, and optical blocking modules.

In one embodiment, the optical stimulation and sensing components comprise at least two light-emitting diodes (LEDs) and at least one photodiode (PD). In one embodiment, the at least two LEDs and the at least one PD are surface mount (SMT) electronic components that are placed and attached onto the fPCB using reflow soldering. In one embodiment, the at least two LEDs comprises a red LED with a peak emission wavelength in a range of about 600-700 nm and an infrared LED with a peak emission wavelength in a range of about 850-1050 nm.

In some embodiments, the optical stimulation and sensing components are arranged in a lateral configuration such that the LEDs have divergent and lateral emission features that maximize light-tissue coupling for a range of implantation sites including blood vessel and cardiac tissue. In one embodiment, the at least two LEDs are positioned laterally to a long axis of the probe. In one embodiment, the PD is positioned to be equidistant to the two LEDs at a distance selected to balance sensing depth, probing volume, and signal to noise ratio. In one embodiment, the probe volume and probe depth are operably adjusted through control over of light intensity of the LEDs and the distance between the LEDs and PD, to allow optimization for measurements of localized tissue oximetry on different sites of interest. In one embodiment, the distance is in a range of about 1-3 mm.

In some embodiments, the optical blocking modules comprise at least two light-blocking structures for eliminating parasitic transmission of light from the LEDs directly to the PD without passing through surrounding tissues of interest. In one embodiment, at least two light-blocking structures comprise two opaque silicone-based cuboid structures. In one embodiment, one of the light-blocking structures is positioned between the PD and one side of the LEDs, and the other of the light-blocking structures is positioned at the probe tip close to the other side of the LEDs.

In some embodiments, a small plug-in connector serves as an electrical interface between the optoelectronic probe and the electronic module and allows battery recharge using a wired interface.

In some embodiments, a medical-grade, biocompatible silicone fully encapsulates the optoelectronic probe to define the low modulus, flexible catheter having a cylindrical shape and smooth surface that facilitates surgical manipulation and insertion. In one embodiment, the low modulus, flexible catheter has a diameter in a range of about 0.5-2 mm.

In some embodiments, the optoelectronic probe is a catheter-type oximetry sensor.

In some embodiments, the optoelectronic probe may further comprise one or more LEDs with peak emission wavelengths different from that of the red LED and the IR LED for additional measurement capabilities.

In some embodiments, the optoelectronic probe further comprises sensors for measuring pressure and flow, and/or means for drug delivery.

In some embodiments, the electronic module is a bendable, miniaturized, battery-powered electronic module adapted for rechargeable powering, circuit control, signal processing, and wireless data communication.

In some embodiments, the electronic module comprises a fPCB, electronic components mounted onto the fPCB, and a battery module coupled with the electronic components, which are disposed between a bottom encapsulation layer and a top encapsulation layer.

In some embodiments, the electronic components comprises a wireless controller for performing data sampling, controlling the LEDs in low duty cycle mode, executing data processing and operating wireless communications. In one embodiment, the wireless communications use at least one communication protocol of near field communication (NFC), Wi-Fi/Internet, Bluetooth, Bluetooth low energy (BLE), and Cellular communication protocols.

In some embodiments, the battery module comprises at least one battery. In one embodiment, the at least one battery is rechargeable.

In some embodiments, the optoelectronic system further comprises a customized app with a graphical user interface deployed on an external device that enables real-time visualization, storage, and analysis of measured data. The graphical user interface provides a control interface to the optoelectronic system. The external device can be a mobile device, a computer, or an ICU monitoring display.

In some embodiments, the optoelectronic system is mechanically compliant and water resistant.

In some embodiments, the optoelectronic system is devoid of physical tethers.

In some embodiments, the optoelectronic system is configured to measure changes in heart rate, respiration rate, ischemia, and arrhythmias.

In some embodiments, the optoelectronic system is useable for monitoring intravascular or intracardiac oxygen saturation at home or in a surgical operation.

In one aspect, the invention relates to a method of fabricating an optoelectronic system. The method includes forming a low modulus, flexible catheter-type optoelectronic probe; and assembling an electronic module detachably and electrically connected to the optoelectronic probe for wireless, real-time, and continuous measurements of physiological information of the subject.

In some embodiments, said forming the catheter-type optoelectronic probe comprises providing a fPCB comprising a flexible substrate and conductive traces, pads and outline defined on the flexible substrate; attaching an optoelectronic sensor onto the fPCB using reflow soldering with low-temperature solder paste to form a sensing module; connecting the sensing module to a detachable connector through a plurality of conductive wires with a desired length; placing the sensing module and the conductive wires into a flexible tube; injecting a biocompatible silicone prepolymer into the flexible tube, and curing the injected silicone prepolymer in a period of time; and removing the flexible tube to form the comprises the low modulus, flexible catheter-type optoelectronic probe. The plurality of conductive wires in some embodiments includes four Teflon-coated copper wires.

In some embodiments, the optoelectronic sensor comprises SMT electronic components comprising a red LED, an infrared LED, and a PD.

In some embodiments, the red and infrared LEDs are positioned laterally to a long axis of the probe, wherein the PD is positioned to be equidistant to the red and infrared LEDs at a distance selected to balance sensing depth, probing volume, and signal to noise ratio.

In some embodiments, the optoelectronic sensor further comprises at least two light-blocking structures, wherein one of the light-blocking structures is positioned between the PD and one side of the red and infrared LEDs, and the other of the light-blocking structures is positioned at the probe tip close to the other side of the red and infrared LEDs.

In some embodiments, the electronic module comprises a fPCB, electronic components mounted onto the fPCB, and a battery module coupled with the electronic components.

In some embodiments, the electronic components comprises a wireless microcontroller.

In some embodiments, said providing the electronic module comprises providing a first layer of a flexible material formed in a mold and a second layer of the flexible material formed on a glass slide, served as a top encapsulation layer and a battom encapsulation layer, respectively; placing the electronic module into the first layer, pouring a solution of soft silicone to fill voids in between electronics and the first layer, and attaching the glass slide with the second layer defined a surface for a skin interface, and clamping them together to form an assembly; curing the assembly to complete encapsulation; and cutting the cured assembly to define a smooth perimeter boundary for the optoelectronic system and openings for detachable and electrical connection to the optoelectronic probe.

According to the invention, the absence of physical tethers and the flexible, biocompatible construction of the probe represent key defining features, resulting in a high-performance implantable oximeter that can monitor localized tissue oxygenation, heart rate and respiratory activity in a patient-friendly mode with wireless, real-time, continuous operation. In vitro and in vivo testing shows that this platform offers measurement accuracy and precision equivalent to those of existing clinical standards.

These and other aspects of the present invention are further described below. Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLE

Wireless, Implantable Catheter-Type Oximeter for Cardiac Oxygen Saturation

Accurate, real-time monitoring of intravascular oxygen levels is important in tracking the cardiopulmonary health of patients after cardiothoracic surgery. Existing technologies use intravascular placement of glass fiber-optic catheters that pose risks of blood vessel damage, thrombosis, and infection. In addition, physical tethers to power supply systems and data acquisition hardware limit freedom of movement and add clutter to the intensive care unit.

This exemplary study introduces a wireless, miniaturized, implantable optoelectronic catheter system incorporating optical components on the probe, encapsulated by soft biocompatible materials, as alternative technology that avoids these disadvantages. The absence of physical tethers and the flexible, biocompatible construction of the probe represent key defining features, resulting in a high-performance, patient-friendly implantable oximeter that can monitor localized tissue oxygenation, heart rate, and respiratory activity with wireless, real-time, continuous operation. In vitro and in vivo testing shows that this platform offers measurement accuracy and precision equivalent to those of existing clinical standards.

The platform includes a thin, flexible catheter-type optoelectronic probe that connects to a small, wearable electronic module for wireless, real-time, and continuous measurements of intravascular oxygen saturation with clinical-grade accuracy. The probe tip in this exemplary embodiment includes high-performance, miniaturized light-emitting diodes (LEDs) and photodiode (PD), fully encapsulated with medical-grade, soft, transparent silicone elastomer. The electronic module supports rechargeable powering, circuit control, signal processing, and wireless data communication based on Bluetooth protocols. A graphical user interface deployed on a smartphone or tablet computer or ICU monitoring display enables real-time visualization, storage, and analysis of measurement data. The absence of physical tethers, the soft, biocompatible construction of the probe, and the lateral (as opposed to distal) configuration of the measurement represent key defining features. Systematic studies of these systems inform optimized choices for the materials, the mechanical layouts, the thermal management approaches, the encapsulation strategies, and the optical setups. Tests on healthy human volunteers yield data that are in excellent agreement with clinical standard pulse oximeters for global oxygen saturation and heart rate measurement. Investigations using rat models show that the catheter can be implanted and sutured to the cardiac surface, and that the measured oximetry values match those determined using a clinical blood gas analyzer. These results represent potentially important advances in wireless optoelectronic technologies for cardiovascular care.

Materials and Methods

Fabrication of Catheter Type Oximeter Probe

Referring to FIGS. 1A-1G, a flexible sheet of copper-clad polyimide (Cu/Polyimide/Cu, 18 μm/75 μm/18 μm, AP8535R, Dupont, Pyralux) served as the substrate for the flexible printed circuit board (fPCB), with conductive traces, pads and outline defined by patterned ablation of the copper using a UV laser system (ProtoLaser U4, LPKF). The surface mount (SMT) electronic components, RED, NIR LEDs and PD were placed and attached using reflow soldering with low-temperature solder paste (Ind. 290, Indium Corporation). This electronics module connected to a detachable connector through four Teflon-coated copper wires (40 AWG enameled copper, Remington Industries) with a length between a few centimeters to 30 cm, depending on the application. Both the electronics module and the thin wires inserted into a flexible tube (Tygon S3 E3630 Flexible Tubings, FisherScientific Inc.). A biocompatible silicone (MED-1000, Avantor Inc., mixed with 5% of Silc-Pig silicone opaque dye) prepolymer injected into the tube using a syringe was fully cured in 12 h. The flexible tube was then removed.

Design and Fabrication of the Electronic Modules

The wireless electronics module was designed using EAGLE 8.5 (Autodesk Inc.). The schematic and PCB layout are described above. A micropower, zero input crossover distortion amplifier (ADA4505-1, Analog Devices Inc) acts as a transimpedance amplifier. A Bluetooth Low Energy (BLE) microcontroller (NRF52832, Nordic Semiconductor Inc.) with a custom program performs data sampling, controls the LEDs in low duty cycle mode, executes data processing and operates Bluetooth communication. With a feedback resistor of 2 mega ohm, the catheter probe and the wireless electronic module have a dark noise (root mean square, RMS) of 1.9 mV for NIR LED, 1.72 mV for Red, which correspond to a photocurrent sensitivity of 0.95 nA for NIR LED, 0.86 nA for Red.

Fabrication involved procedures similar to those described above, with an fPCB patterned using the laser ablation tool, and SMT components assembled using reflow soldering. A 3-axis milling machine (Roland MDX 540) formed aluminum molds in geometries defined by 3D CAD drawings created using ProE Creo 3.0. Films of a soft silicone material (Silbione RTV 4420; Part A & Part B, mixed with 5% of Silc-Pig silicone opaque dye) created in the mold by drop-casting and other films formed by spin-casting (250 rpm) on glass slides, both thermally cured in an oven (70° C. for 30 min), served as top and bottom layers, respectively, for a soft, encapsulating enclosure. Placing the fully assembled electronic module into the molded layer, pouring a solution of soft silicone to fill the voids in between electronics and the top layer, and attaching the glass slides with silicone films defined the surface for the skin interface. Clamping the parts together and placing the entire assembly into an oven for curing (70° C. for 30 min) completed the encapsulation. A final cutting process with a $CO_2$ laser (ULS) defined a smooth perimeter boundary for the system, and a manual cutting process with a small blade defined openings for the connector and switch.

Characterization of the Optoelectronic Performance

Spectroscopic measurements (using FOIS-1 Fiber Optic Integrating Sphere, Ocean Optics; FLAME-S-UV-VIS Spectrometer, Ocean Optics) yielded the emission spectra for the red and NIR LEDs. Exposing the photodetector to light passed through a chopper and recording the photocurrent using a data acquisition system (PXI-1031, National Instruments) provided measurements of the response time.

Monte Carlo Simulation of the Optical Characteristics

Simulations of light transport in biological tissues used Monte Carlo methods for the devices reported here and for conventional fiber optic systems to define the spatial illumination profiles. The simulations used a three-dimensional computational space with 700×700×700 bins of $2\times10^{-9}$ $cm^3$ volume, and a total of $11\times10^6$ photon packets for each simulation. Commercial light-emitting diodes (LEDs) with peak emission wavelengths at 645 nm (red) and 950 nm (near infrared, NIR) served as light sources, both with active illumination areas of 0.25×0.25 $mm^2$ and emission angles of ±60°. For the optical fiber system, the optical core had a diameter of 0.2 mm a numerical aperture of 0.22, to yield illumination in a ±9.5° emission cone in aqueous solution ($n_{aqueous}$=1.38). The irradiances at the illumination surfaces for both setups were 9.21 mW/$mm^2$ for red and 14.4 mW/$mm^2$ for NIR. Light propagation was simulated in cardiac muscle tissue with the corresponding wavelength dependent scattering anisotropy factor ($g_{Red-m}$=0.93, $g_{NIR-m}$=0.93), absorption coefficient ($\mu_{a-Red-m}$=0.56 $cm^{-1}$, $\mu_{a-NIR-m}$=0.46 $cm^{-1}$) and scattering coefficient ($\mu_{a-Red-m}$=79 $cm^{-1}$, $\mu_{s-NIR-m}$=64 $cm^{-1}$). Additional simulations in aqueous solution defined the illumination profiles produced by both systems at the red wavelength. The scattering anisotropy factor ($g_{Red-a}$=0.95), scattering coefficient ($\mu_{s-Red-a}$=1 $cm^{-1}$) and absorption coefficient ($\mu_{a-Red-a}$=0.43 $cm^{-1}$) were used for a solution with 1.6 μM concentration of fluorescent dye (Alexa Fluor 647) as a local illumination reporter (MW=1.25 kDa and i=$270\times10^3$ $cm^{-1}M^{-1}$). The illumination profile was extracted from the simulation volume given by the photon fluence (Φ) which represents the phenomenological optical irradiance.

Figure 2A:
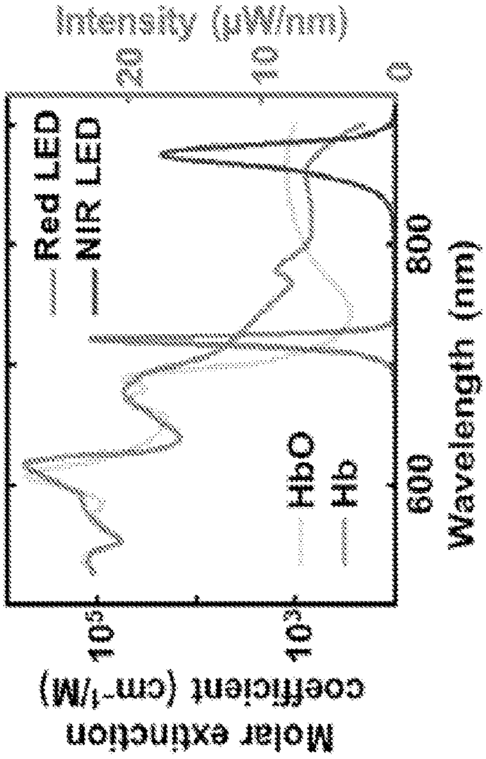
FIGS. 2A-2G show optical, thermal and electronic characteristics of the wireless catheter oximeter, according to embodiments of the invention.
Figure 2B:
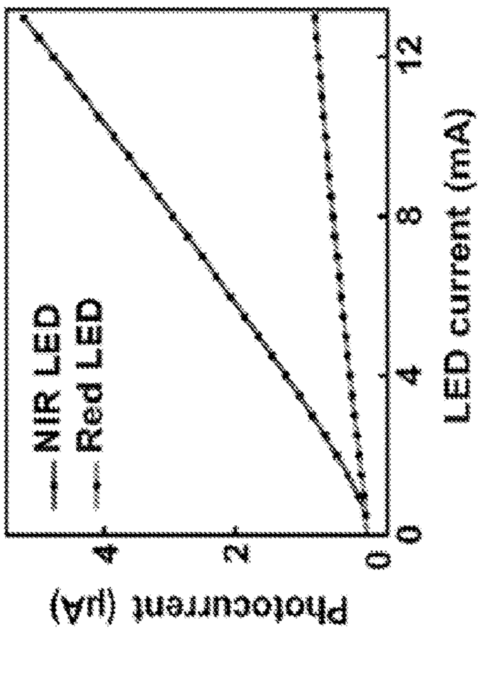
Figure 2C:
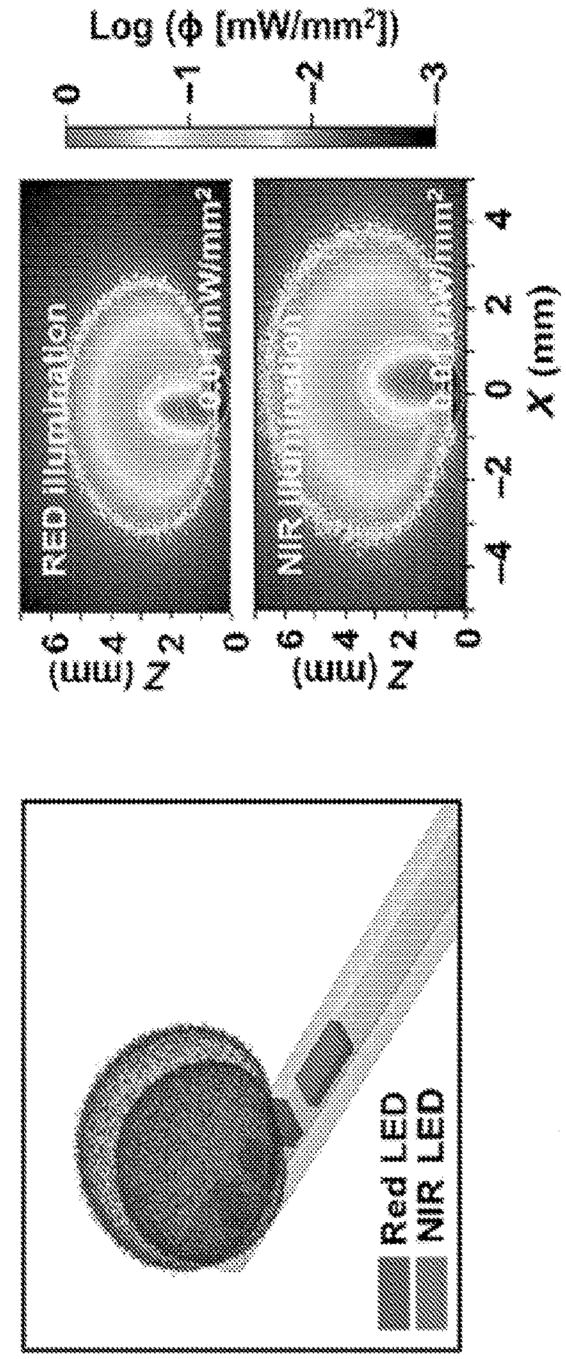
Figure 4A:
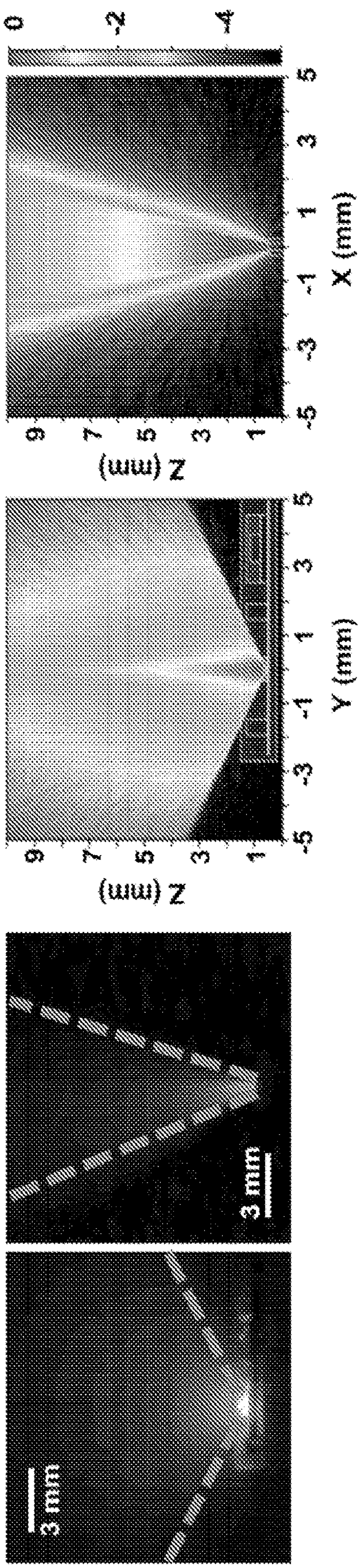
Figure 9A:
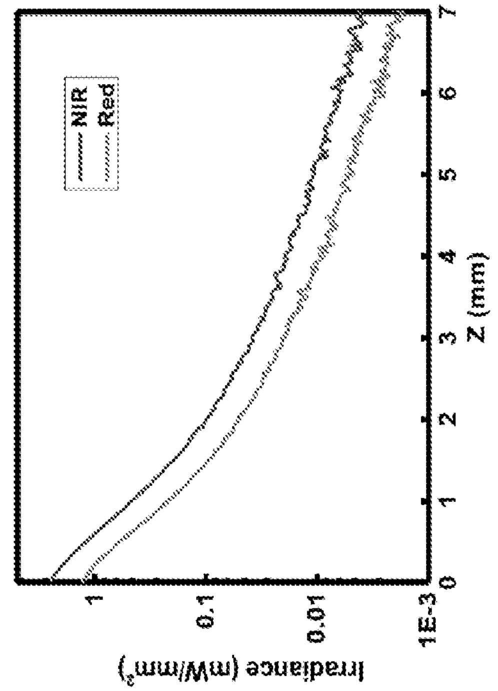
FIGS. 9A-9D show Monte Carlo simulation of the optical characteristics.
Figure 9B:
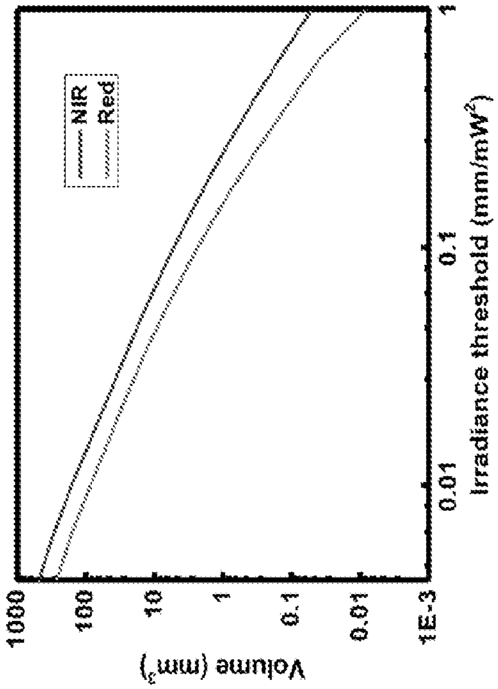

FIG. 2C (right) presents results of simulations for the catheter probe in cardiac muscle tissue. FIG. 2C (left), presented as a 3D rendering (Paraview 5.7.0), highlights the 0.01 mW/$mm^2$ fluence contour for red and NIR illumination. FIG. 9A shows the light decay from the catheter-muscle tissue interface along the LED's normal direction. Furthermore, FIG. 9B shows the illumination volume in muscle tissue predicted by the simulations at different irradiance thresholds. For an illumination threshold of 0.01 mW/$mm^2$, the penetration depth from the catheter-muscle interface along the LED's normal direction is 3.84 and 5.16 mm and the illumination volume of the tissue is 85.3 $mm^3$ and 159.8 $mm^3$ for the red and near-infrared wavelengths, respectively. FIG. 4A (right) shows the simulated illumination profiles, produced by red light for the catheter-type probe and the optical fiber in aqueous solution.

Characterization of the Thermal Properties of the Catheter Oximeter Probe

An NTC component (ERTJZEG103FA, with dimensions of 600 μm×300 μm×300 μm, Panasonic Co.) attached to the outer encapsulation layer, at a position directly above the LEDs, yielded measurements of temperature for the case of insertion inside a piece of pork belly. The thermistor connected to the input of a digital multimeter (PXIE-4065, National Instrument) through Teflon-coated copper wires (40 AWG enameled coppwer, Remington Industries), for continuous resistance measurements. The oximeter probe was activated at 1 min and de-activated at 4 min, for a total recording of 6 min. Converting the resistances into temperatures using manufacturers specifications yielded changes in temperature as a function of time during this simple on-and-off cycle, as shown in FIG. 2E.

Heat transfer analysis shown in FIGS. 10A-10D was performed with the commercial software COMSOL 5.2a (Heat-Transfer Modeling User's Guide) to compute the change in temperature (ΔT) in the heart as a result of the thermal power associated with operation of the LEDs and with absorption of the emitted light. Heat generated by cardiac metabolism and the effects of blood perfusion were not considered in the simulation. The Pennes' bio-heat equation is then written as $$\rho C_p\frac{\partial T}{\partial t}+\nabla\cdot(-k\nabla T)=Q_{the}+\Phi\mu_a$$

where T is temperature, t is time; k, ρ, and Cp are the thermal conductivity, mass density and heat capacity of the heart, respectively; $Q_{the}$ is the heat generated from thermal power of the LEDs. The heat associated with light emission was calculated as the product of the light fluence rate Φ obtained in the optical simulation and the absorption coefficient j a of the cardiac muscle tissue. The optical and thermal properties appear in Tables 1 and 2. The cardiac tissue, probe geometry, and the LEDs were modeled using 4-node tetrahedral elements. Convergence tests of the mesh size were performed to ensure accuracy. The total number of elements in the models was approximately 650,000.

TABLE 1

Cardiac muscle tissue absorption coefficients ($cm^{-1}$) used in the optical simulations at red and NIR wavelengths.

| | Red light (645 nm) | NIR Light (950 nm) |
|---|---|---|
| Cardiac tissue | 0.56 | 0.46 |

TABLE 2

Thermal properties of materials and cardiac tissues used in the thermal simulations

| | Thermal Conductivity k ($W\ m^{-1}\ K^{-1}$) | Specific Heat Capacity Cρ ($J\ kg^{-1}\ K^{-1}$) | Density ρ ($kg\ m^{-3}$) |
|---|---|---|---|
| Cardiac | 0.493 | 3212 | 1041 |
| Copper | 377 | 385 | 8960 |
| Polyimide (PI) | 0.21 | 2100 | 909 |
| PDMS | 0.2 | 1460 | 970 |
| μ-ILED | 130 | 490 | 6100 |

Measurements of Young's Moduli

The Young's moduli of different coating materials were measured by indentation testing (Hysitron BioSoft Indenter, Bruker) with an indenter radius of r=200 μm. Tests on films of different materials (~1 mm in thickness) generated force-displacement curves upon contact of the indenter and the film surface. The Young's modulus was calculated by fitting the force-displacement data within an indentation depth (δ=20 μm using a Hertzian contact model.

Measurements of Bending Stiffness

Figure 12B:
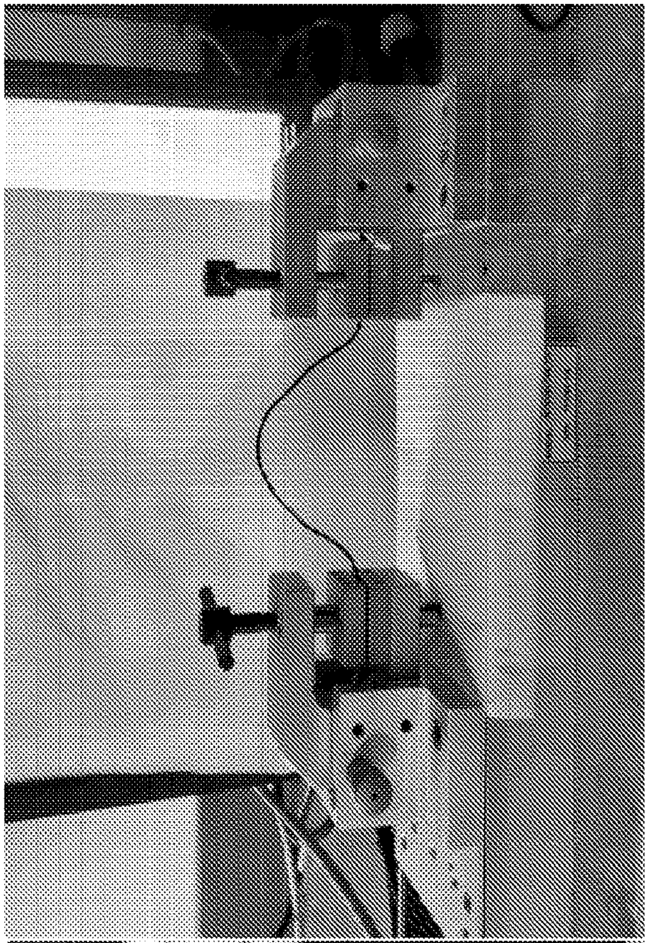
FIGS. 12A-12B show respectively dynamic mechanical tester setup for measuring the bending stiffness of the catheter probes, and test platform for measuring the catheter oximeter probe during bending and stretching for FIG. 3E.
Figure 12A:
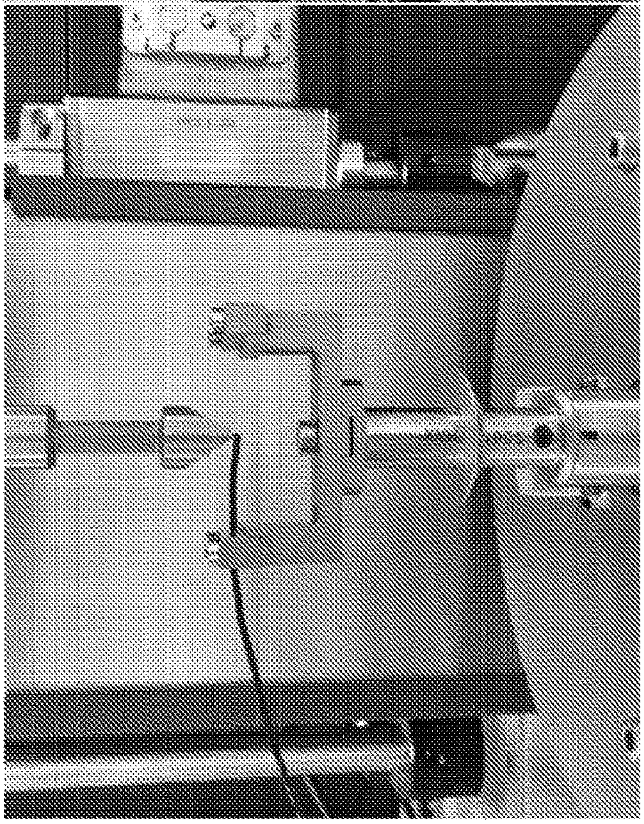

Catheter tubes with different coating materials and conductive copper wire diameters exhibit different bending stiffness, as measured by cantilever bending tests using a dynamic mechanical analyzer (RSA-G2, TA Instruments). A wire sample (L=19 mm) with one end clamped and the other end under a point load applied by an indenter served as a cantilever for bending stiffness measurement (FIG. 12A). For a cantilever beam with point load at the end, under small deflections, the relationship among the end deflection δ, force and bending stiffness EI is given by $$\delta = \frac{FL^3}{3EI}, \text{ for } \delta << L.$$

The bending stiffness EI can then be calculated as $$EI = \frac{FL^3}{3\delta}.$$

For each measurement, the force-displacement data from the initial deflection of 6=0.2 mm upon contact between the indenter and the wire was used for the calculation of bending stiffness. Four measurements at different sections of the wire were taken for each sample.

Characterization of the Mechanical Properties of the Catheter Oximeter Probe

The finite element analysis (FEA) commercial software ABAQUS (Analysis User's Manual 2010, V6.10) was utilized to study the mechanics and to optimize the design layouts and materials selections. The objective was to decrease the strains in the Cu wire interconnects and the Cu layers in the sensor probe during mechanical deformations. The silicone, Cu wires (80 μm diameter), and PI films (75 μm thick) were modeled by hexahedron elements (C3D8R) while the thin Cu layer (18 μm thick) of the flexible printed circuit board were modeled by shell elements (S4R). The minimal element size was 115 th of the width of the narrowest interconnects (15 μm), to ensure the convergence of the mesh, and the accuracy of the simulation results. The values of the elastic modulus (E) and Poisson's ratio (ν) used in the analysis were $E_{Cu}$=119 GPa, $\nu_{Cu}$=0.34, $E_{PI}$=2.5 GPa, $\nu_{PI}$=0.34, $E_{Slicone}$=1 MPa, and $\nu_{slicone}$=0.49.

Cyclic Bending and PBS Soaking Tests

The two ends of a device were clamped (distance between the two clamped ends is 4 cm) to two translational stages. Repeatedly moving one translational stage towards the other back and forth by a distance of 3 cm led to bending of the probe to minimum bending radius of −5 mm. After every 2000 bending cycles, the probe was removed from the apparatus, inserted into an integrating sphere (Fiber Optic Spectrometer FOIS-1 Integrating Sphere, Ocean Optics), connected to the electronic module, and activated to yield measurements of photovoltages corresponding to emission from the two LEDs. Gripping the tip of the probe between the thumb and index finger, connecting the probe to the electronic module, and operating the system yielded photoplethysmograms. Such tests were performed up to 10,000 bending cycles. The soak tests began with immersion of the probe into a chamber filled with phosphate-buffered saline (PBS) and mounting in an oven at 37° C. Evaluations of the devices occurred once per week, according to procedures described above, for a total of 8 weeks.

In Vivo Tests of Biocompatibility

A medical-grade autoclave system (Tuttnauer EZ10 Fully Automatic Autoclave) was used to sterilize the optical sensing probe, with LEDs, PD and light blocking elements on the fPCB and fully encapsulated with a medical-grade silicone material (MED-1000) in a cylinder (diameter: 1.5 mm, length: 16 mm) just prior to implantation. The procedures involved anaesthetizing a female CD-1 mouse (Charles River Laboratories) with isoflurane gas (~2%), opening a 2-cm-length pocket at the subcutaneous region on the back near the spine, inserting the device into the pocket, and suturing to close the surgical opening. The procedures were approved by the Institutional Animal Care and Use Committee of Northwestern University (protocol IS00005877). The health status of each animal was checked daily. Euthanizing the mice at 1 month after device implantation preceded the extraction of blood. Charles River Laboratories conducted complete blood counts and blood chemistry tests on samples collected in K-EDTA tubes and gel tubes, respectively.

Figure 3A:
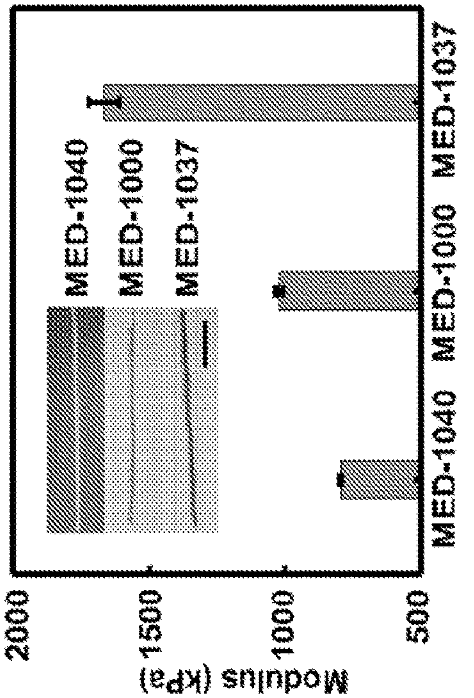
FIGS. 3A-3H show mechanical, encapsulation and biocompatibility characteristics of the wireless catheter oximeter, according to embodiments of the invention.
Figure 3B:
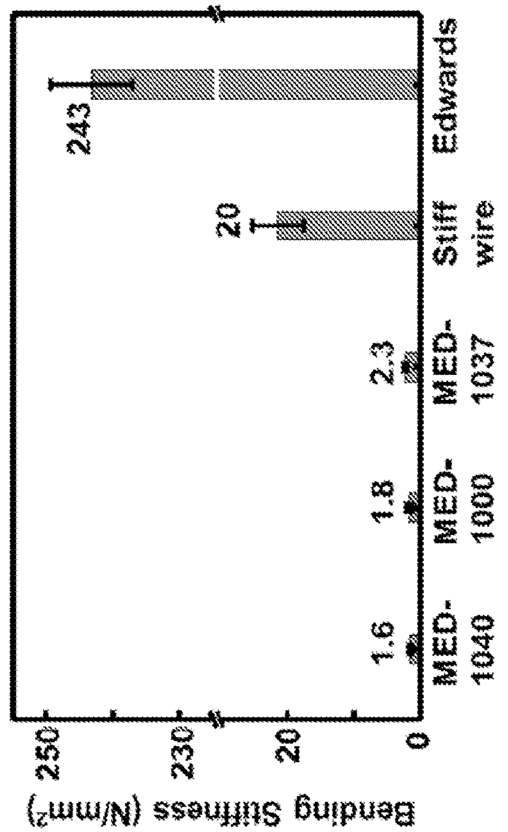
Figure 18A:
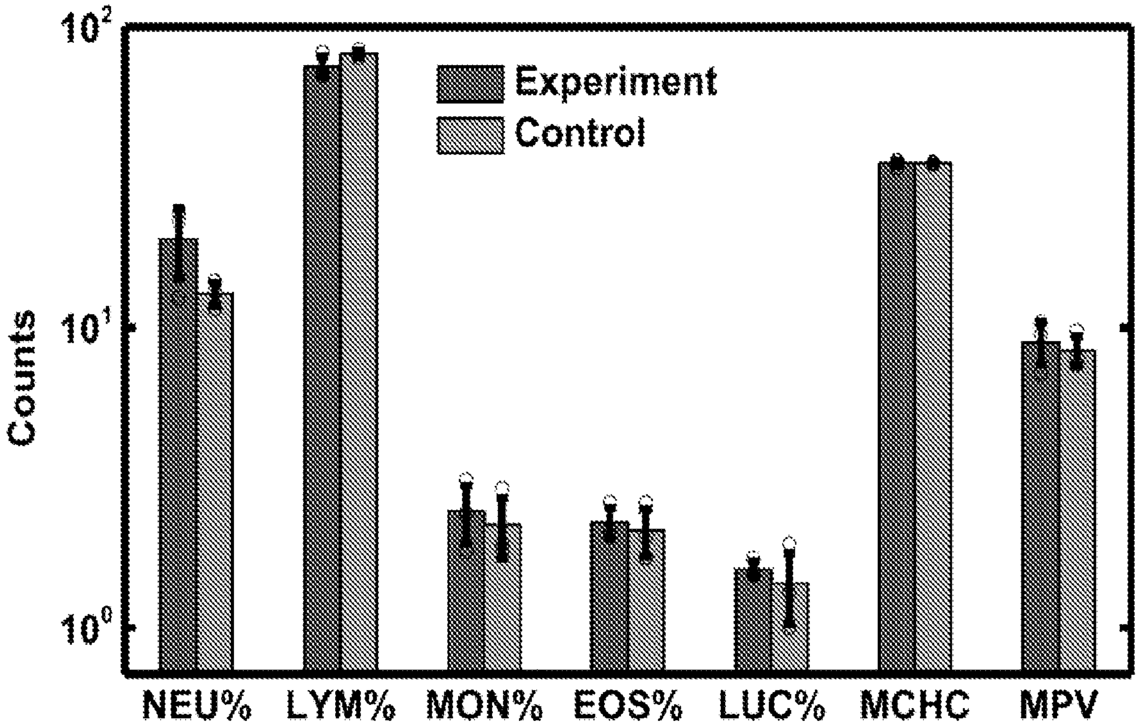
FIGS. 18A-18B show analysis of complete blood count (FIG. 18A) and blood chemistry (FIG. 18B) for the mice with catheter oximeter probe implanted subcutaneously for 30 days (labeled as Experiment) and the mice without device implantation (labeled as Control). Abbreviations and corresponding units include, NEU %: percentage of neutrophils (%), LYM %: percentage of lymphocytes (%), MON %: percentage of monocytes (%), EOS %: percentage of eosinophils (%), LUC %: percentage of large unstained cells (%), MCHC: mean corpuscular hemoglobin concentration (g/dL), MPV: mean platelet volume (fL), TP: total protein (g/dL), CREA: creatinine (mg/dL), TBIL: total bilirubin level (mg/dL), ALB: albumin (g/dL), GLOB: globulin (g/dL), Na: sodium (mEq/L), K: potassium (mEq/L), Cl: chloride (mEq/L).
Figure 18B:
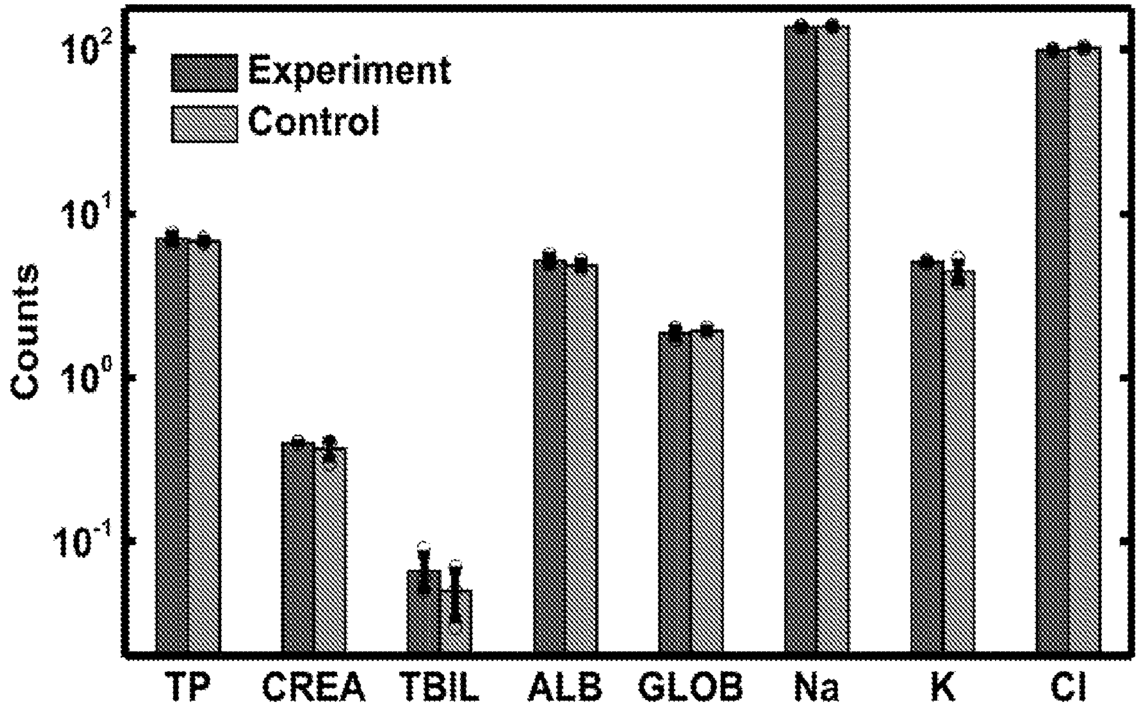

Analysis of complete blood count (FIG. 3G) and blood chemistry (FIG. 3H) for mice with the probe implanted in subcutaneous region on the back near the spine for 30 days (labeled as Experiment) and for mice without device implantation (labeled as Control), indicated no sign of organ damage or injury, and no change in the electrolyte and enzyme balance for 1 month. During the period of study, the data showed no significant change in average count of white blood cells (WBC), red blood cells (RBC), platelets (PLT), hemoglobin (HGB), hematocrit (HCT), mean corpuscular volume (MCV), mean corpuscular hemoglobin (MCH), red cell distribution width (RDW), platelet count (PLT), and mean platelet volume (MPV) compared with control group, indicating absence of any abnormalities, including anemia, nutritional deficiency, liver disease, bleeding disorder, and heart attack, as shown in FIGS. 3G and 18A. Tests of blood chemistry yielded information on enzymes and electrolytes, as diagnostic biomarkers of organ-specific diseases and metabolic disorders. In all cases, the results fell within confidence intervals of control values, as shown in FIGS. 3H and 18B. Specifically, normal levels of albumin (ALB), total protein (TP), alanine aminotransferase (ALT), alkaline phosphatase (ALP), aspartate transaminase (AST) indicated normal liver function. Normal levels of blood urea nitrogen (BUN), creatine (CREA) indicated normal kidney function. Normal levels of glucose (GLU), calcium (Ca), sodium (Na), potassium (K), chloride (Cl), and phosphorus (PHOS) suggested normal function of the metabolic system.

In Vitro Experiments to Compare the Performance of the Wireless Catheter Oximeter with a Conventional Fiber Optic Device Defibrinated horse blood (100 ml, from Fisher Scientific) contained in a cylindrical reservoir (diameter: 4 cm, height: 30 cm) was maintained at 37.0±0.1° C. by a temperature controller (Fisher Scientific). Inserting both the catheter probe of the wireless sensing system and a commercial fiber optic catheter oximeter (Swan Ganz 777F8, recorded by HemoSphere monitoring platform, Edwards Life Science Inc) into the reservoir with the sensing tips 3 cm below the surface of the horse blood and in the center of the reservoir to eliminate effects of the reservoir sidewalls enabled comparative measurements of oxygenation. Adding reducing agents (ranging from 0.01 to 0.1 mg. sodium dithionite, purchased from Millipore Sigma) into the reservoir converted some of the oxygenated hemoglobin into deoxygenated hemoglobin, to define, in a controlled manner, the oxygenation level across a relevant range from 35% to 73%.

Human Tests of Pulse Oximetry

Figure 4B:
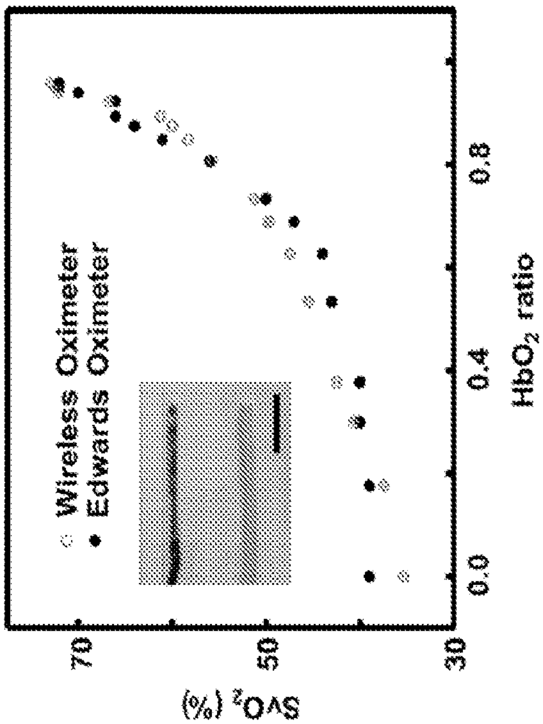
Figure 4C:
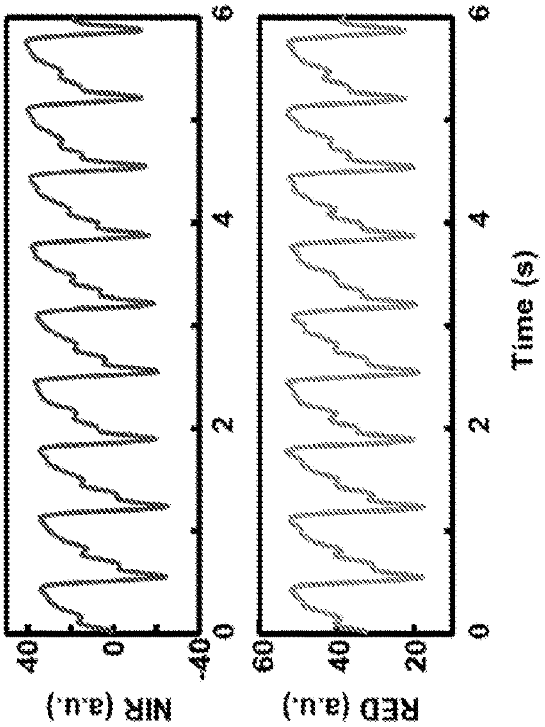
Figure 4G:
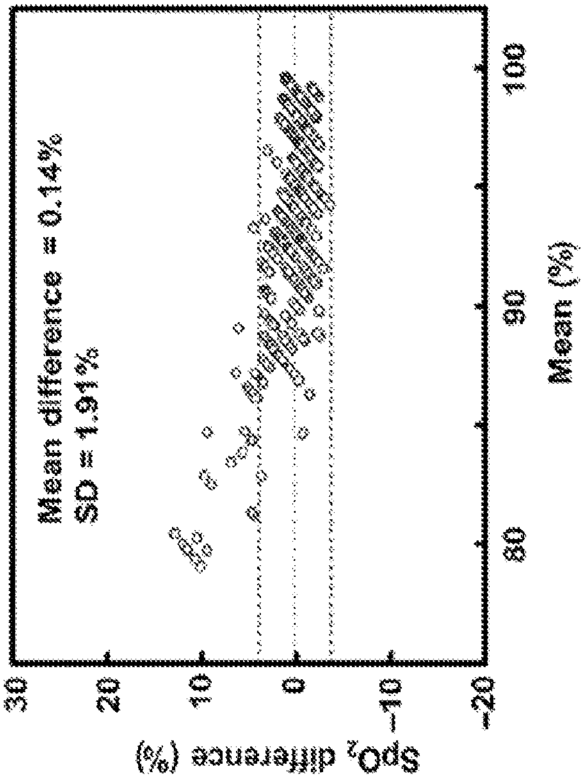
Figure 20A:
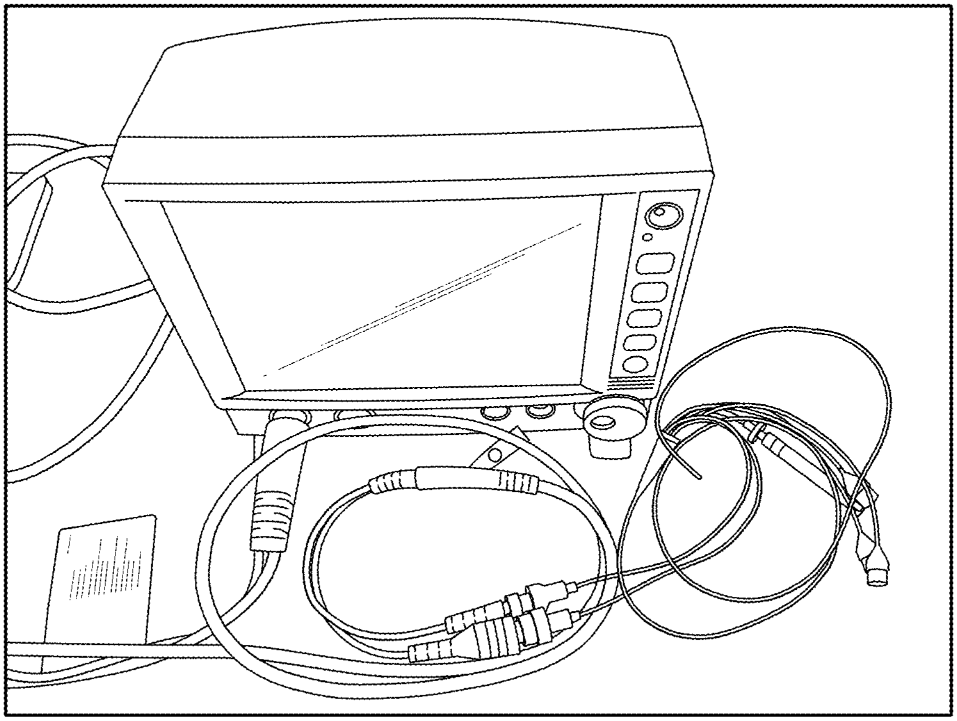
FIGS. 20A-20B show commercial fiber optic catheter oximeter system, and the in vitro comparison test between this system and the wireless catheter oximeter.
Figure 20B:
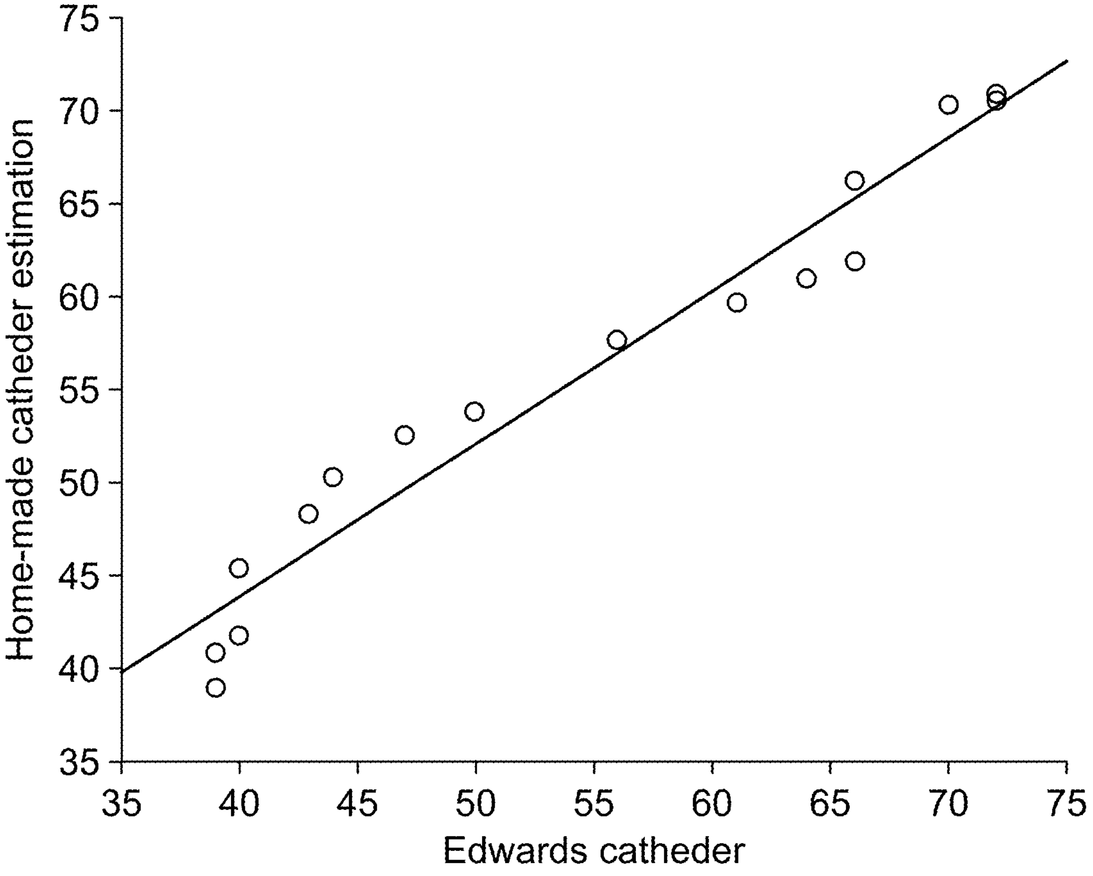
Figure 22:
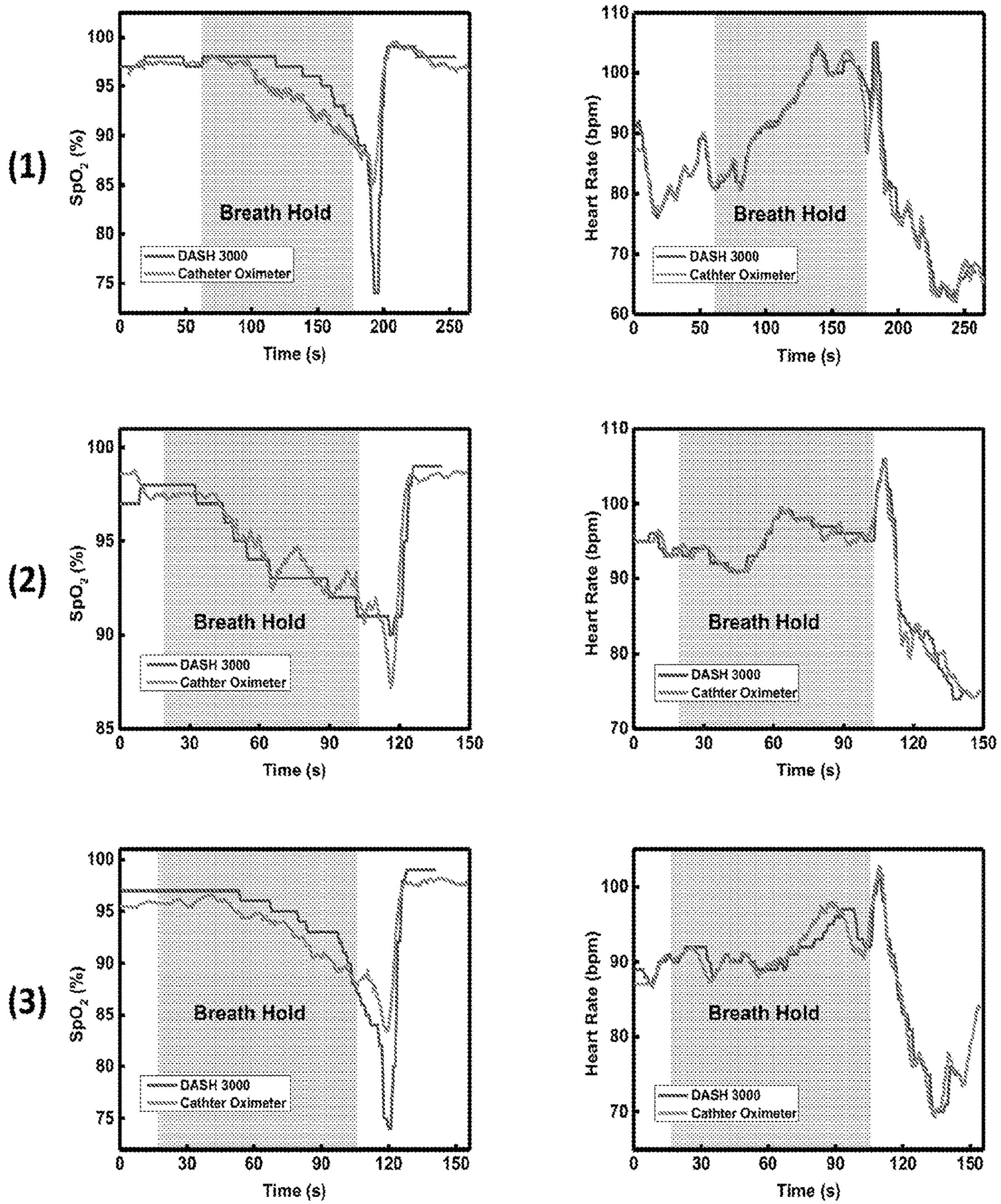
FIG. 22 shows additional comparison tests (3 more) between wireless catheter oximeter and clinical standard pulse oximeter. Measured $SpO_2$ (left) and heart rate (right) from the wireless catheter oximeter attached to the finger during a period of rest followed by a breath hold and then another period of rest, and comparison of the results to measurements performed using a commercial oximeter attached to the other finger (DASH 3000, General Electronics Inc.).

Testing on human subjects involved placing the wireless catheter probe on the index figure. A standard transmissive oximeter (GE DASH 3000) was clasped on the index finger of the other hand, as shown in FIGS. 20A-20B. Both systems recorded heart rate and oximetry information from subjects simultaneously for roughly 4 min, as shown in FIGS. 4F-4G and 22. In the experiment, the subject remained at rest for the first 30 s to define a base line, then began to breath hold, followed by normal breathing until the end of experiment. A diverse group of subjects (N>4, including East Asian, Indian and Caucasian demonstrated the device capabilities across a range of physical conditions and skin types.

In Vivo Experiments to Measure Cardiac Physiology

Male Sprague Dawley rats (weight: 400-500 g; age: 14-16 weeks) were purchased from Charles River Laboratories International. Inc. (Wilmington, MA). The animals were kept on a 12-h light-dark cycle in a temperature-controlled room. The experimental procedures were approved by the Animal Care and Use Committee of the Northwestern University and conformed to the Guide for the Care and Use of Laboratory Animals (Institute for Laboratory Animal Research, National Academy of Sciences, USA, 8th edition, 2011).

Sprague Dawley rats were initially anesthetized in a chamber with isoflurane gas (5% isoflurane, 100% oxygen). Once consciousness was lost, the animals were intubated with a 16-gauge flexible catheter, and endotracheal tube was connected to a mechanical ventilator (Braintree VentStar ventilator) that provided positive-pressure ventilation with oxygen/isoflurane. The ventilator was set based on animal weight: tidal volume (Vt, mL)=$6.2\times M^{1.01}$ and respiratory rate (RR, $min^{-1}$)=$53.5\times M^{-0.26}$, M=animal weight in kilograms. Each rat was connected to a vaporizer that delivers approximately 2.0% isoflurane driven by 100% oxygen. Rats were placed in the dorsal decubitus position on a warming platform. Intradermal bupivicaine was infiltrated at the incision sites approximately 10 min prior to incisions. Rats were maintained at approximately 37° C. on a heating pad, with body temperature monitored throughout the experiment using a rectal temperature probe. The animal's hair was removed from the surgical site with hair removal cream NAIR post shaving. The surgical areas were scrubbed and disinfected with a povidone iodine prep pad and the area was then wiping with an alcohol prep pad. Peripheral blood oxygen saturation was monitored throughout the experiment using a commercial pulse oximetry system (MouseSTAT Jr., Kent Scientific Co.).

Figure 24:
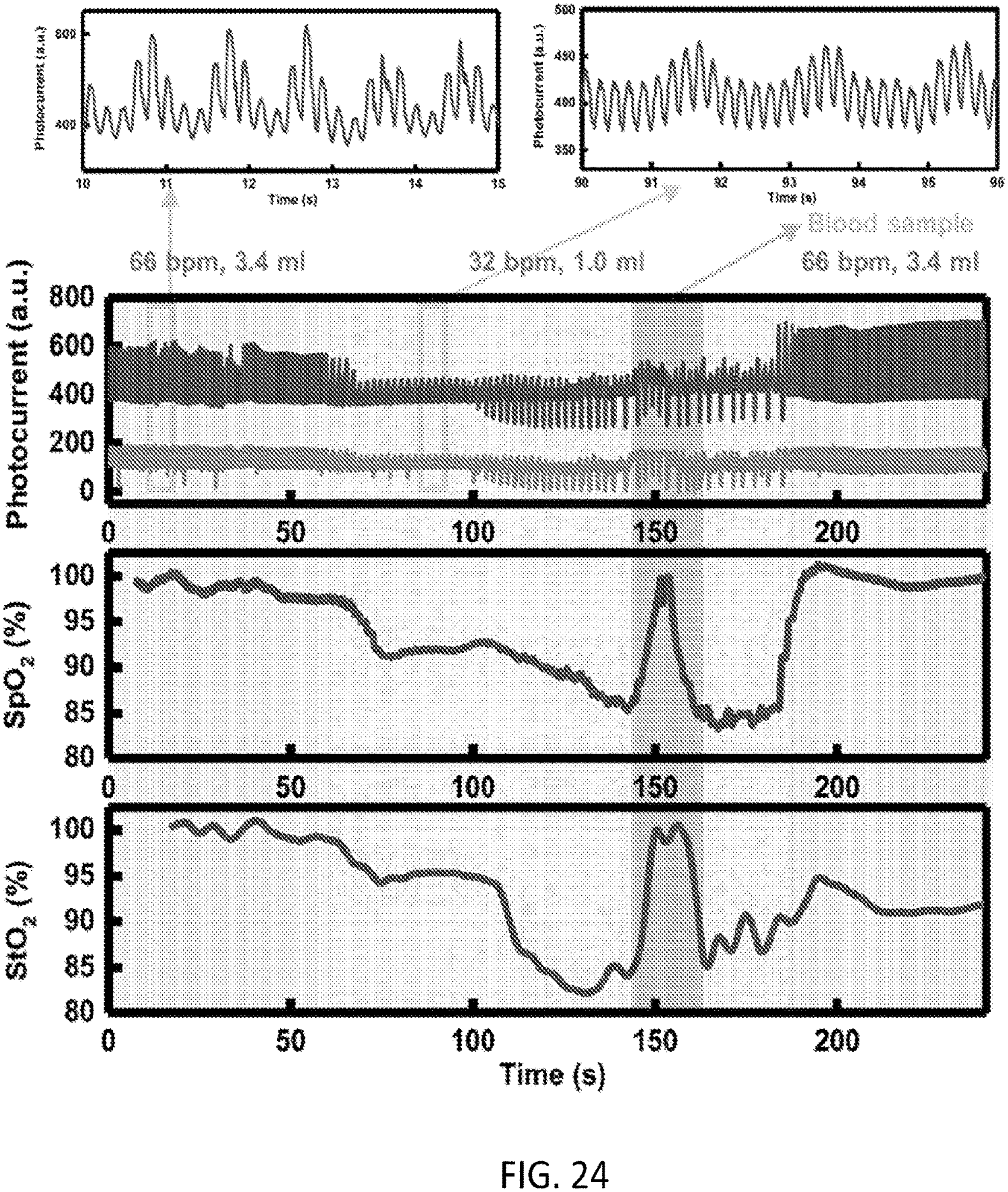
FIG. 24 shows raw data and calculated oxygen saturation from a wireless catheter oximeter, recorded from a rat heart during changes in the oxygen supply environment. The left ventricle blood was sampled and measured in the middle of the recording.

Details of thoracotomy in rats appear elsewhere. Briefly, isoflurane-anesthetized rats were ventilated with room air supplemented with 100% oxygen. A left thoracotomy was performed at the fourth intercostal space, and the heart was suspended in a pericardial cradle. The left lung will be gently pushed away from the pericardium with a small sponge. The oximeter probe was sutured to the anterior wall of the left ventricle close to the left anterior descending coronary artery with a nylon 6-0 suture, avoiding injuring coronary vessels. The oximeter wire went through a subcutaneous tunnel to the head. After instrumentation was completed, all rats were stabilized for 30 min and subjected to hypoxia by adjusting ventilation rate and tidal volume of the ventilator. The blood was withdrawn from the chamber of the left ventricle using a 27 G needle with 1.0 ml syringe, as shown in FIG. 24. The blood samples were used to measure pH, $SO_2$, $PO_2$, and $PCO_2$ by a blood gas analyzer (i-STAT 1, Abaxis Inc.).

Data Analysis and Calculation of $SpO_2$

Analysis of pulse oximeter data relied on a commercial software package (MATLAB® R2016b, The MathWorks Inc.). Data acquired from the two LEDs (Red: R, 640 nm, InfraRed: IR, 950 nm) were provided by the system at a sampling frequency of 100 Hz. The signal at each wavelength was bandpass filtered (0.5-3 Hz for human data, 3.5-6 Hz for animal data, 4th order, zero-lag Butterworth digital filter) to extract the main frequency of the pulsating component, AC(t), and low-pass filtered (0.5 Hz, 4th order, zero-lag Butterworth digital filter) to estimate the slow fluctuating signal unrelated to pulsation, DC(t), e.g. induced by respiration. The relative pulsatile signal intensity S(t) was computed as the ratio of the two signals for both the red and the infrared wavelengths:

$$S(t) = \frac{AC\ (L)}{DC\ (L)} \tag{1}$$

A local minima (m) and maxima (M) identification algorithm in the signal S(t) identified the peaks of each pulse cycle and yielded an interpolated modulation amplitude, A(t), as:

$$A(t) = M(t) - m(t). \tag{2}$$

The ratio R(t) between the red and infrared pulsatile components at every sample was evaluated in a moving integration window of 5 s as:

$$R(t) = \sum_{5S} \frac{\ln(A(L)_R + 1)}{\ln(A(L)_{IR} + 1)}. \tag{3}$$

From photon-diffusion theory and the modified Lambert-Beer equation, the following equation can be derived to express the relationship between the percent of arterial blood saturation, $SpO_2(t)$, and the R(t):

$$S_pO_2(t) = \frac{\varepsilon_{Hb_R} DPF_{R/IR} - \varepsilon_{Hb_{IR}} R(t)}{\left(\varepsilon_{Hb_R} - \varepsilon_{HbO_{2_R}}\right) DPF_{R/IR} + \left(\varepsilon_{HbO_{2_{IR}}} - \varepsilon_{Hb_{IR}}\right) R(t)} \cdot 100, \tag{4}$$

where $\varepsilon_{HbO_R}$ and $\varepsilon_{HO_R}$ are the extinction coefficients of oxy- and deoxyhemoglobin ($HbO_2$ and Hb) for the red light, $\varepsilon_{HbO_{IR}}$ and $\varepsilon_{HO_{IR}}$ are the extinction coefficients of oxy- and deoxyhemoglobin for the infrared light, and $DPF_{R/IR}$ describes the ratio between differential pathlength factors (DPFs) at the two wavelengths of interest. The extinction coefficients of the two forms of hemoglobin at the wavelengths of interest were extracted from Zijlstra and colleagues: $\varepsilon_{HbO_{2R}}$=0.011 $min^{-1}$, $\varepsilon_{Hb_R}$=0.106 $min^{-1}$, $\varepsilon_{HbO_{2IR}}$= 0.028 $min^{-1}$, $\varepsilon_{Hb_{IR}}$=0.018 $min^{-1}$. The quantity $DPF_{R/IR}$ describes the effects of the dissimilar optical path lengths. The color dependence of the optical path length depends on the scattering nature of the biological tissue and its dependence on the light wavelength. A practical problem when using Equation 4 for $SpO_2$ estimation is that the DPF ratio depends on the baseline optical properties of the tissue, including the tissue microstructure and the $SpO_2$ itself. This issue can be addressed by calibrating the oximeter empirically. A constant DPF ratio can be considered over narrow ranges of saturation (80%|100%). Based on literature and empirical results from our measurements, we set $DPF_{R/IR}$=1.4. This value accounted for the increased optical path length of red light compared to infrared light. Equation 4 yielded arterial oxygen saturation levels close the those determined by the commercial system on several subjects and across the full range of saturation levels investigated. The data were also used to determine the beats per minute, BPM(t). The time dependence of the BPM was estimated from the inter-beat frequency f(t), evaluated as the inverse of the difference between the times of two consecutive maxima M(t) in the NIR, within an integration period of 5 s as:

$$BPM(t) = 60 f(t)_{IR,5s}. \tag{5}$$

Calculation of Blood Oxygen Saturation

Evaluation of blood saturation in in-vitro experiments used averages of red and IR values converted into optical densities (ODs) according to the equation:

$$OD(i) = -\ln\left(I(i)/I_0\right), \tag{6}$$

where I(i) is the recorded signal intensity in each experimental phase and $I_0$ is its value in the first phase. In the absence of pulsating signals, assumptions on the baseline hemoglobin concentration and its oxygen saturation are required to infer changes in the saturation. We assumed a concentration of 15 g/dl for hemoglobin in the blood solution and, based on the commercial catheter oximeter, an oxygen saturation of 39% in the first experimental phase. When considering that the molar mass of hemoglobin is 65 kg/Mol, these assumptions yielded a baseline $HbO_2$ and Hb concentration in blood of $HbO_{20}$=0.90 mM and $Hb_0$=1.41 mM, respectively. Calculation of changes in $HbO_2$, $\Delta HbO_2$, and Hb, $\Delta Hb$, were evaluated employing the modified Lambert-Beer law.

$$\begin{bmatrix} \Delta HbO_2(i) \\ \Delta Hb(i) \end{bmatrix} = \frac{1}{\rho_{eff}} \begin{bmatrix} \varepsilon_{HbO_{2_R}} & \varepsilon_{Hb_R} \\ \varepsilon_{HbO_{2_{IR}}} & \varepsilon_{Hb_{IR}} \end{bmatrix}^{-1} X \begin{bmatrix} OD_R(i) \\ ODI_R(i) \end{bmatrix}, \tag{7}$$

where $\rho_{eff}$ is the effective photon path in the backreflection recording geometry and are the extinction coefficients for the two chromophores.

The saturation of blood for each phase was estimated as:

$$SO_2(i) = \frac{HbO_{20} + \Delta HbO_2(i)}{HbO_{20} + \Delta HbO_2(i) + Hb_0 + \Delta Hb_2(i)}.$$

The effective photon path of the probe was estimated experimentally by fitting to $SO_2$(i) the commercial catheter oximeter saturation values, as shown in FIG. 20B.

Results

Design Features

FIG. 1A illustrates the operational characteristics of an implantable, wireless catheter-type optoelectronics system, highlighting its miniaturized, biocompatible design and capabilities for wireless (Bluetooth low energy, BLE), real-time monitoring at the surface of the heart. The integrated platform, fully encapsulated with a medical-grade silicone layer, includes three main components: (1) a low modulus, flexible catheter with an optoelectronic sensor that contains two light-emitting diodes (LEDs with emission wavelengths of 645 nm and 950 nm) and one silicon photodiode (PD), (2) a bendable, miniaturized, battery-powered BLE electronic module that can gently mount onto the skin and (3) a custom graphical user interface (GUI) deployed on a handheld device that supports real-time visualization, storage, and analysis of measurement data, and provides a control interface for setting the illumination parameters for the LEDs (FIG. 1A). In the use case considered here, the sensing probe can be placed on the surface of the desired cardiovascular structure, where it is mechanically stabilized with fine sutures. Electrical interconnects attach to the BLE module, secured with a skin-safe adhesive onto the chest.

Figure 1B:
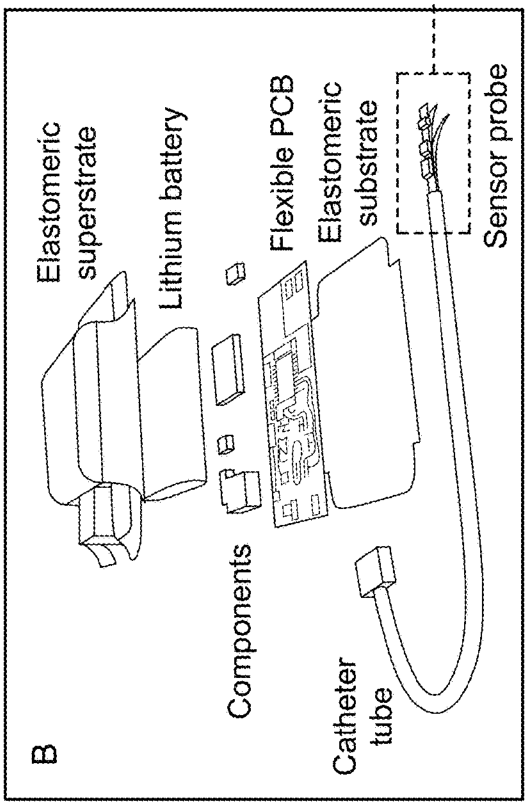
Figure 1C:
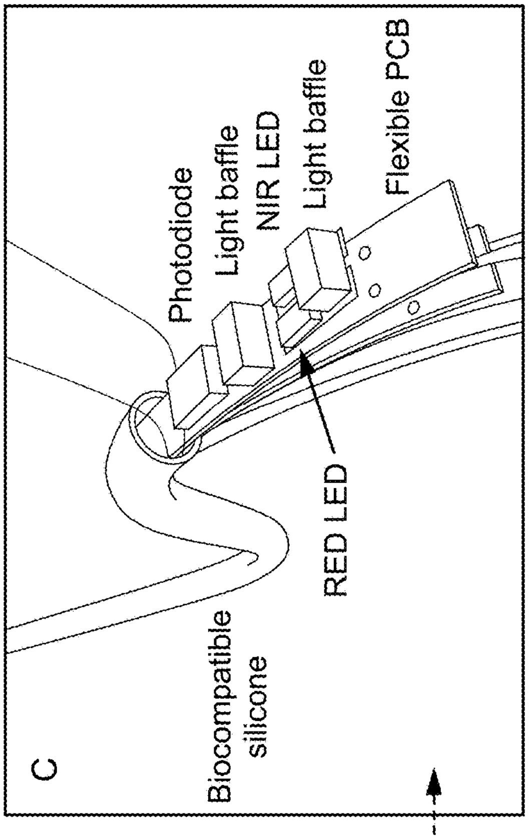

The exploded view schematic illustration of this module shown in FIG. 1B highlights an elastomeric substrate (Silbione RTV 4420, Elkem), a flexible printed circuit board (fPCB) with a collection of electronic components, a rechargeable lithium-ion battery, and a top encapsulation layer (Silbione RTV 4420, Elkem). FIG. 1C presents a magnified view of the probe, with its two LEDs and PD, and two opaque silicone-based cuboid structures (polydimethylsiloxane (PDMS) mixed with 5% of Silc-Pig silicone opaque dye; L×W×H: 1 mm×0.5 mm×0.8 mm) for light blocking, all mounted on an fPCB in the geometry of a narrow, thin strip (width 1.3 mm, thickness 111 μm, length 14 mm), that connects, through thin, Teflon-coated copper wires (diameter: 80 μm), to the BLE module. A small plug-in connector serves as an electrical interface between the probe and the module and allows battery recharge using a wired interface. A medical-grade, biocompatible silicone (MED-1000, Avantor Inc) fully encapsulates the optical sensing probe, to define a cylindrical shape (diameter: 1.5 mm) and smooth surface that facilitates surgical manipulation and insertion. The light-blocking elements lie between the PD and LEDs, and at the probe tip close to the other sides of the LEDs, to eliminate parasitic transmission of light from the LEDs directly to the PD without passing through the surrounding tissue of interest. The distance between the LEDs and the PD sets the characteristic depth associated with the detected backscattered light. Increasing this distance enlarges the effective probing volume and enhances the changes in signal associated with changes in blood oximetry, but also decreases the amount of light detected by the PD due to increased absorption and scattering events in the light path. The geometry reported here positions the PD equidistant between the two LEDs, at a distance of 2 mm, selected to balance sensing depth, probing volume, and signal to noise ratio.

Figure 1D:
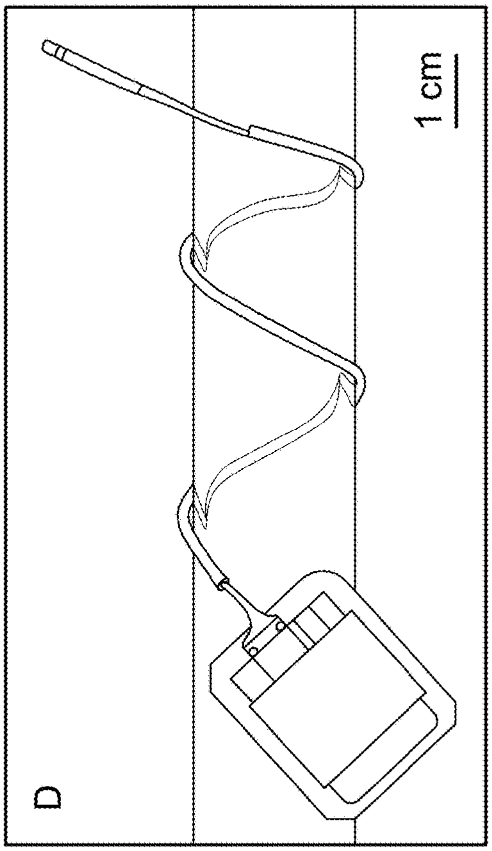
Figure 1E:
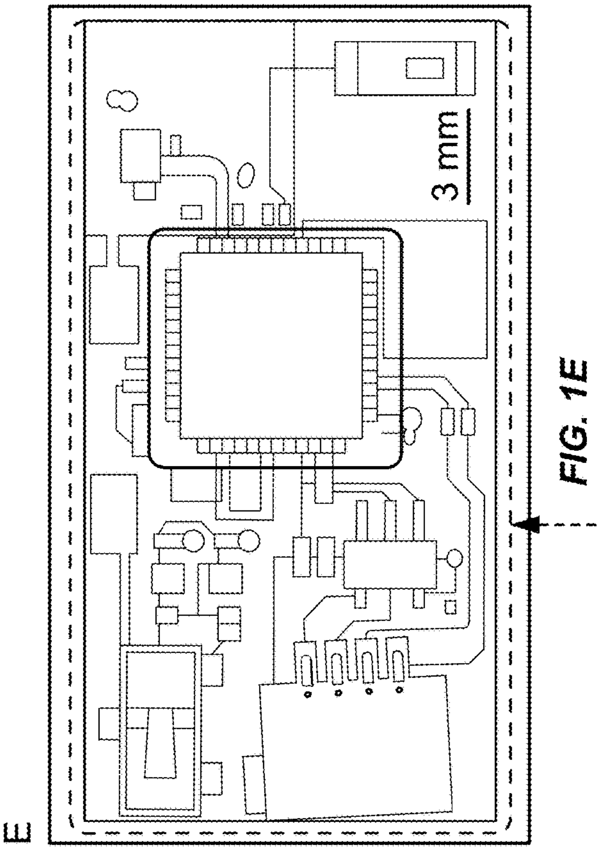
Figure 1F:
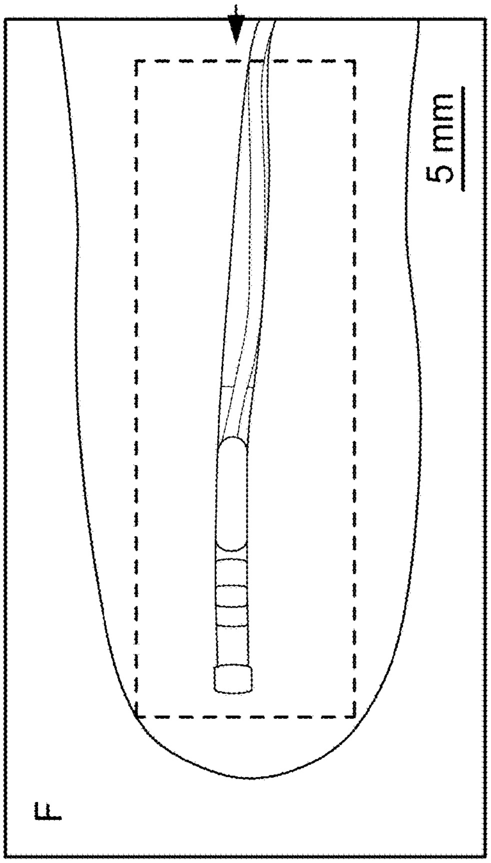
Figure 1G:
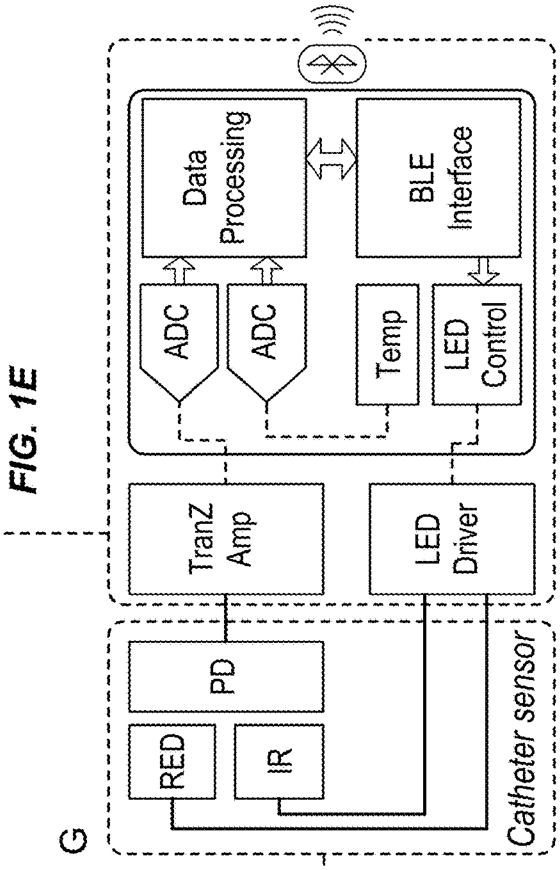

FIG. 1D presents an image of a device wrapped onto a glass rod with radius around 1 cm, to highlight its flexibility. FIGS. 1E-1F show top-down views of the layout of the electronic components, with a corresponding schematic block diagram shown in FIG. 1G. The red and NIR LEDs at the tip end of the probe receive power from driving circuitry modulated by a microcontroller unit (MCU) in the BLE module, such that the LEDs turn off and on out of phase. The PD output passes through a trans-impedance amplifier to yield an amplified voltage signal. A 14-bit analog-digital converter (ADC) supports signal sampling at a rate of 200 Sa/s, corresponding to 100 Sa/s for each LED. The MCU performs smoothing on the raw data with a finite impulse response (FIR) 7-point moving average filter, as a low pass filter with cut-off frequency of 6.4 Hz at sampling speed of 100 Sa/s. Data transfer occurs wirelessly to a personal computer through BLE protocols. A custom GUI software serves as a control interface and mechanism for data storage and display. Established data analytics routines yield heart rate and oximetry values, as described in the section of Materials and Methods.

Optical, Thermal and Electrical Characterization

Oxy-hemoglobin ($HbO_2$) and deoxy-hemoglobin (Hb) correspond to hemoglobin with and without bound oxygen, respectively. Well-known optical approaches provide effective estimates of blood oxygen saturation, defined as the fraction of $HbO_2$ relative to total hemoglobin ($HbO_2$+Hb), by comparing the distinct absorption spectra of $HbO_2$ and Hb in the visible and NIR spectral range. FIG. 2A shows the measured emission spectral profiles of the red and NIR LEDs and their peak emission wavelengths at 645 nm and 950 nm, respectively, along with the molar extinction coefficient (Y) spectra of HbO2 and Hb. The data show an isosbestic point near 800 nm where the Hb and $HbO_2$ have the same Y. For wavelengths above and below, the values of Y for $HbO_2$ and Hb change in relative magnitude. The large differences at 645 nm and 950 nm establish the basis of optical measurement of blood oxygenation based on the Beer-Lambert law.

Figure 7A:
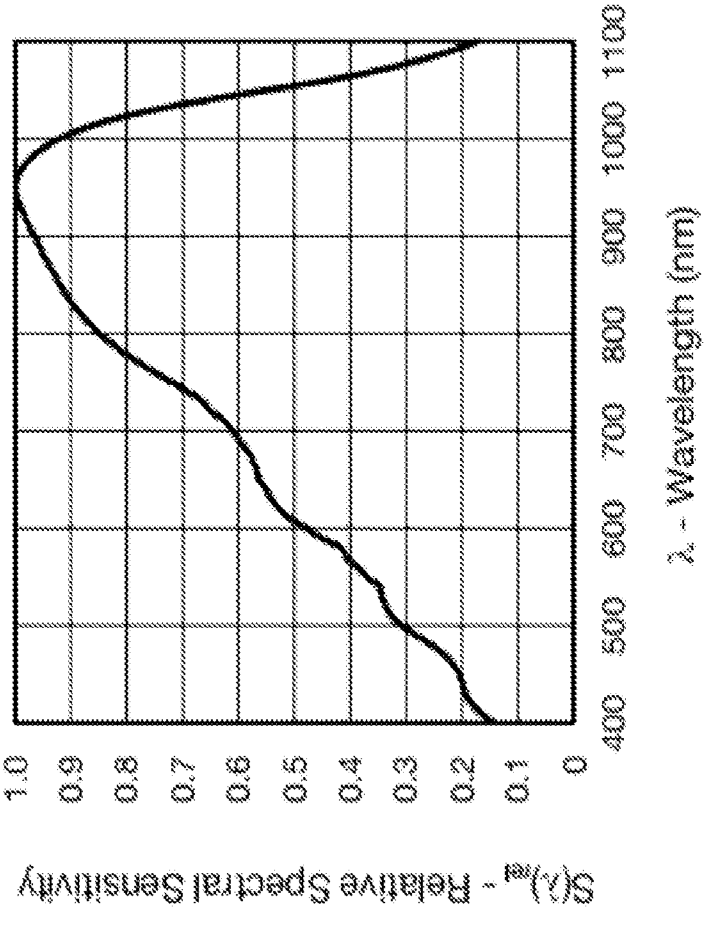
FIGS. 7A-7B show photoelectric characterization of the miniaturized photodiode, according to embodiments of the invention.
Figure 7B:
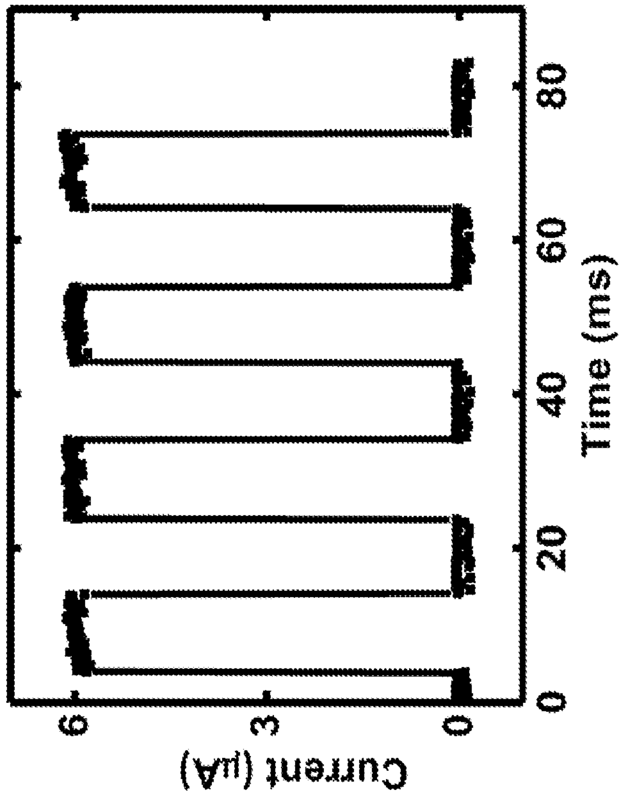
Figure 8A:
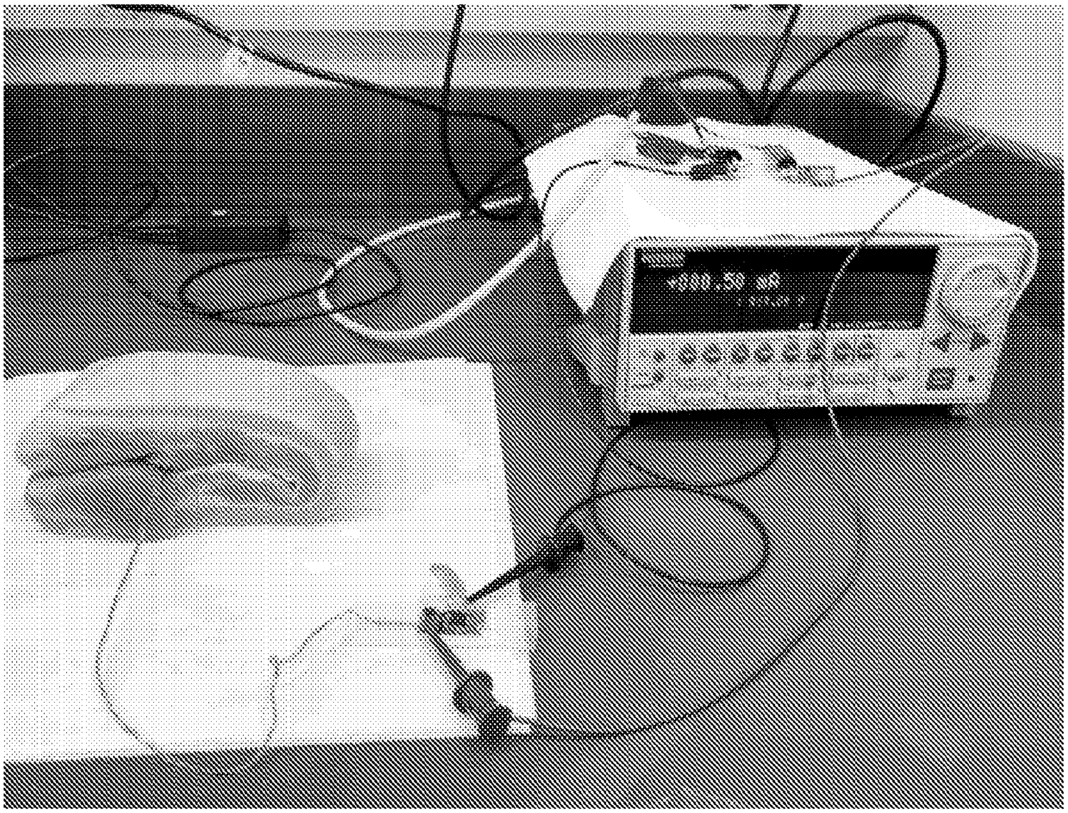
FIGS. 8A-8B show test platforms for measuring the optical response and thermal characteristics of the catheter oximeter probe.

The optical sensing probe uses a single high-speed photodiode (TEMD7000X01, Vishay Semiconductors Inc.) with relative spectral sensitivities S(Z) at 950 nm and 640 nm of 99% and 54%, respectively, as shown in FIG. 7A. FIG. 7B illustrates the photocurrent response to illumination with light passed through a chopper (red light, wavelength: 633 nm). The results suggest response times less than 1 ms, sufficient for current purposes. FIG. 2B shows the photocurrent from the red and NIR LEDs with probe buried inside raw meat (FIG. 8A). The red light induces lower photocurrent response compared to the NIR by a factor of ~6.5 for the same drive current, consistent with differences in the efficiencies of the two LEDs and in the spectral response of the PD. The PD exhibits a linear response with illumination intensity at both wavelengths. Based on these observations and on power and circuit considerations, the devices use drive currents of 3.1 mA (9.2 mW/mm$^2$) and 1.8 mA (14.4 mW/mm$^2$) for the red and NIR LEDs respectively, thereby generating corresponding photocurrents with a ratio of 1:2.3.

Figure 9C:
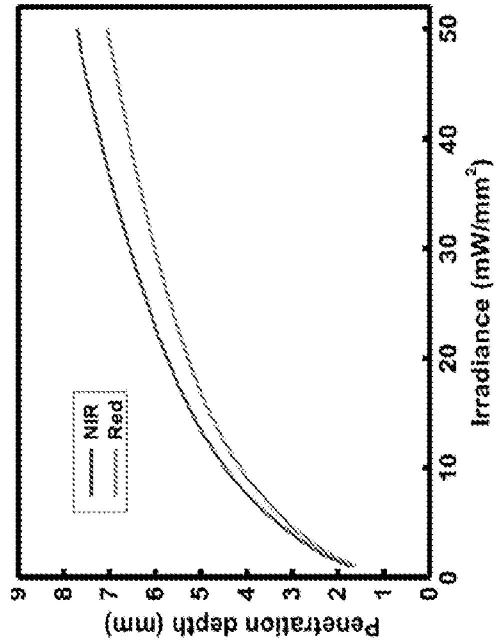
Figure 9D:
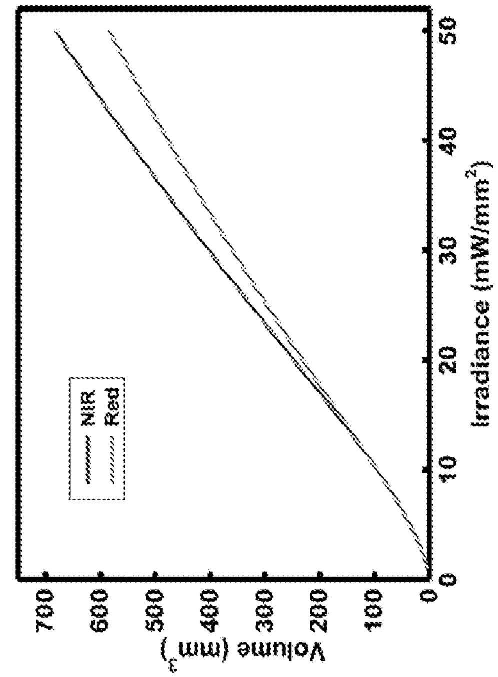
Figure 10A:
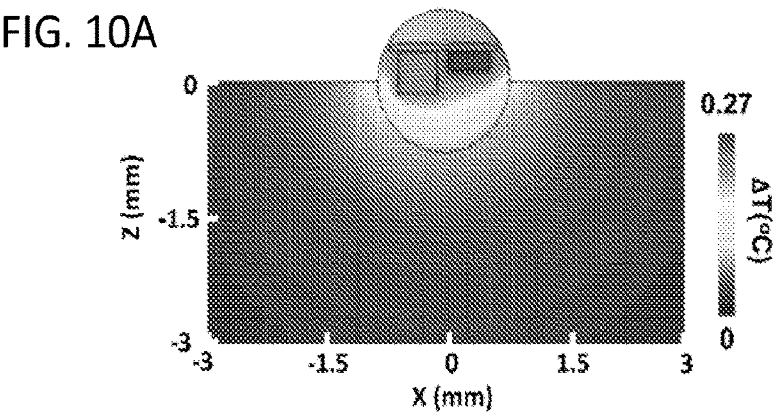
FIGS. 10A-10D show Finite Element Analysis (FEA) results of temperature change in the tissue and catheter probe after the probe operation of 120 s.
Figure 10B:
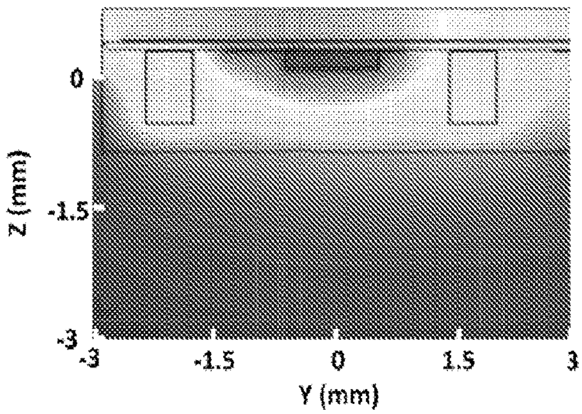
Figure 10C:
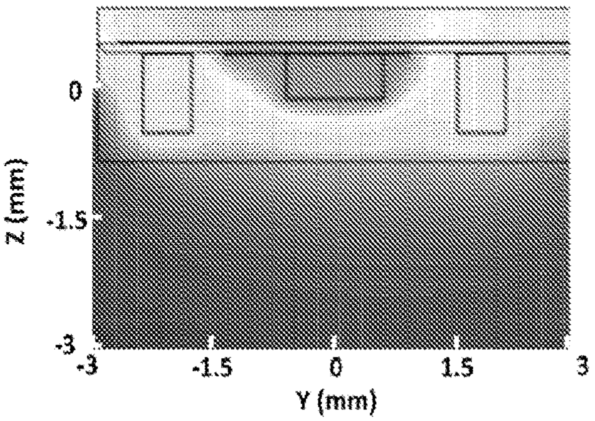
Figure 10D:
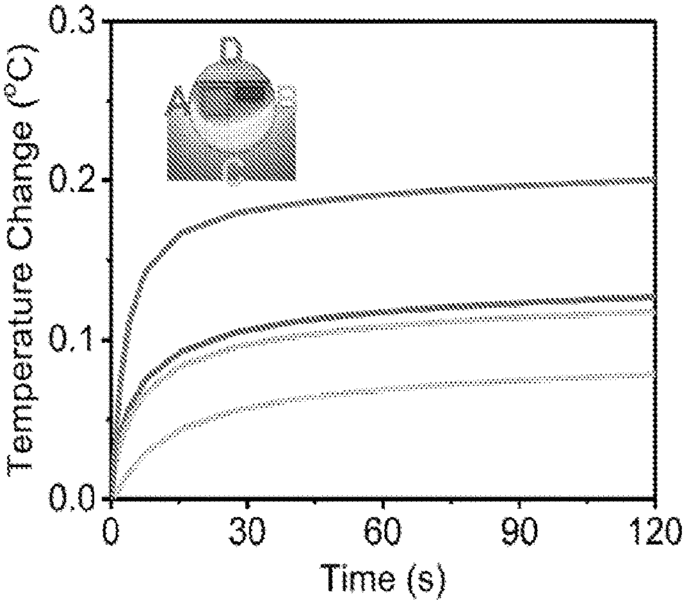

The physics of light transport in biological tissues can be captured numerically using the Monte Carlo method. The results provide quantitative insights into the illumination distributions around the LEDs and into aspects of light detection by the PD, as shown in FIG. 2C. The model uses the optical properties of human cardiac muscle tissue found in the literature. Other details of the simulation appear in the section of Materials and Methods. FIG. 2C shows normalized emission intensity profiles of the red and NIR LEDs as a function of distance, in three-dimensions (left), and in two-dimensions at a cross-sectional plane across the LEDs (right). The penetration depth, where the optical irradiance decreases to 0.01 mW/mm$^2$, is 3.84 mm and 5.16 mm for the red and NIR LEDs, respectively. In the same token, the illumination volume is 85.3 mm$^3$ and 159.8 mm$^3$, respectively for red and NIR LEDs (FIGS. 9A-9B). Moreover, by varying the intensity from 0 to 50 mW/mm$^2$ (FIGS. 9C-9D), the penetration depth varies from 0 to 7 mm, with an illumination volume up to 600 mm$^3$. This adjustable illumination depth and volume can be useful for different application requirements, from thin tissues associated with blood vessels to thick tissues such as those of the myocardium, to measure either intracardiac or intravascular oxygenation.

Figure 2D:
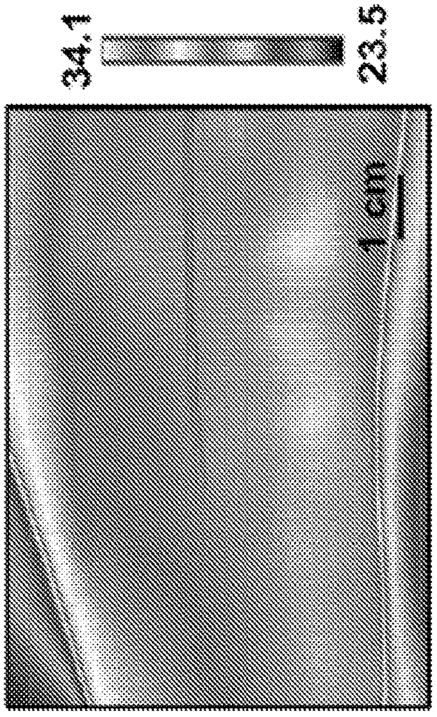
Figure 2E:
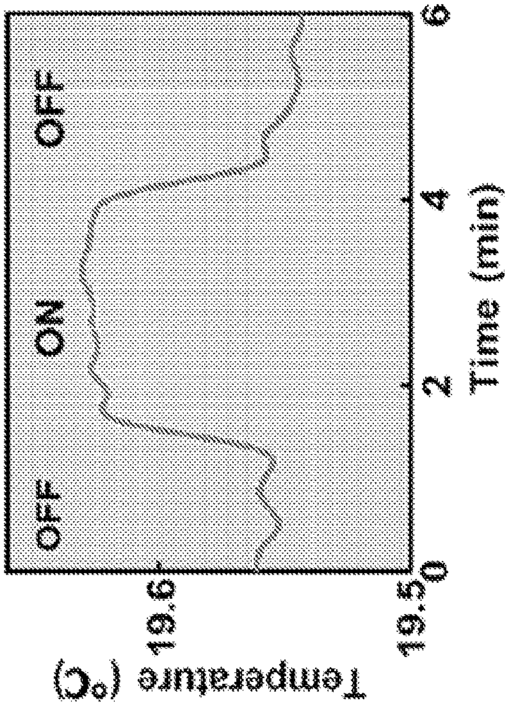
Figure 2F:
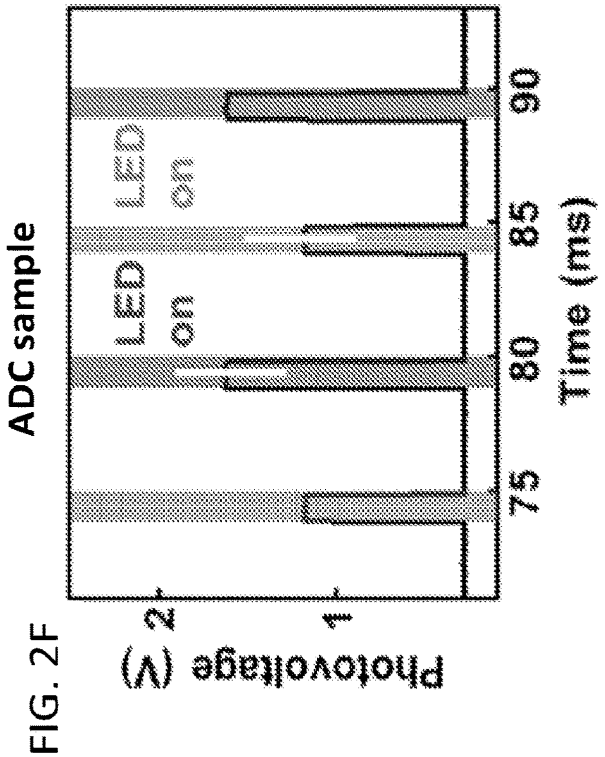
Figure 8B:
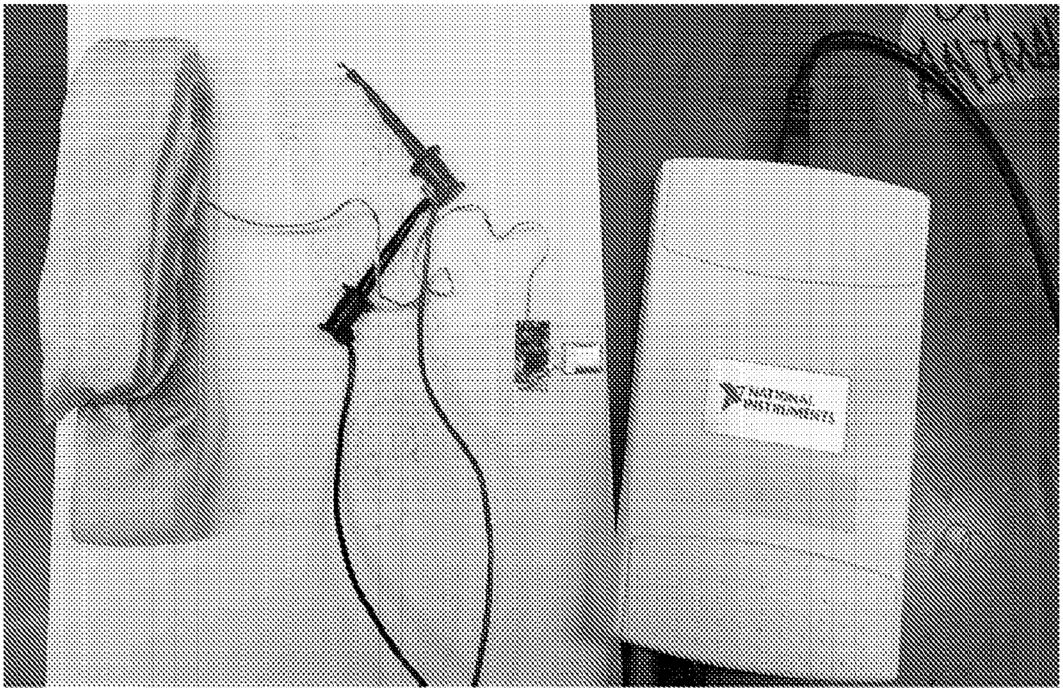

Thermal images shown in FIG. 2D collected with an IR camera (FLIR A325SC, FLIR Systems) show no apparent increase in temperature around the LEDs during operation of a device pressed against the skin. Driving the LEDs and sampling the PD response at low duty cycles (10% duty cycle with 1 ms pulse widths at 100 Hz sampling rate, as shown in FIG. 2F) leads to low power consumption and low heat generation while preserving well-defined modulation, as shown for the case of the probe placed at the fingertip (FIG. 4C). A small-scale negative-temperature-coefficient (NTC) thermistor allows quantitative evaluation of the temperature near a probe inserted into pieces of raw meat (FIG. 8B). The measurements indicate a small increase in temperature (~0.08° C.) during operation of the device (FIG. 2E), consistent with the results of Finite Element Analysis (FEA), in which the average temperature rise of four points around the active LEDs in the probe is roughly 0.1° C., as shown in FIGS. 10A-10D. This value is more than thirty times lower than the maximum allowed increase in internal temperature, 3° C. The measured rise time is comparable to that determined by simulation, i.e. ~20 s. Details on this measurement and simulation appear in the section of Materials and Methods.

Figure 2G:
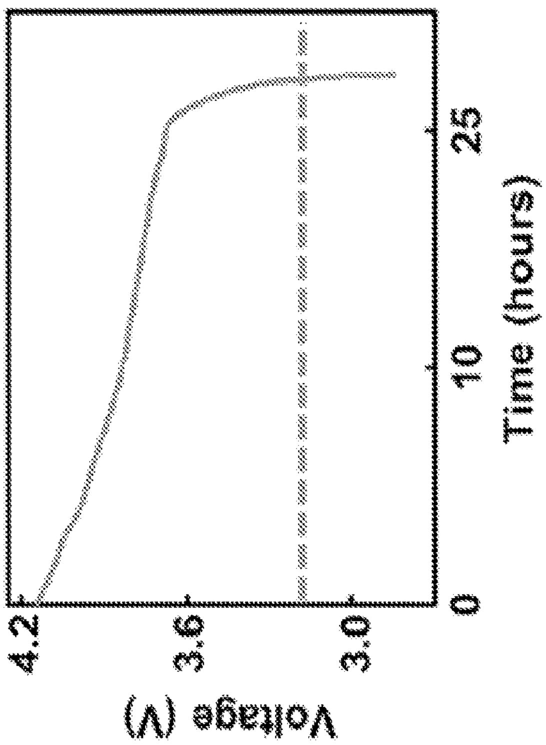

Minimizing the duty cycle also reduces the power consumption of the system and thereby extends the battery life. The system reported here uses a 45 mAh rechargeable lithium battery. For operational parameters described previously, this battery supports continuous operation and wireless data streaming at 200 Sa/s for more than 22 h using a 10% duty cycle (FIG. 2G). Reducing the sampling frequency can further prolong the battery life, depending on requirements. For instance, measurements performed every 5 min, for a duration of 5 s, with the system in sleep mode for other times will extend the battery life by 60 times, corresponding to roughly 1300 h.

Mechanical Characterization and Encapsulation Performance

Figure 11A:
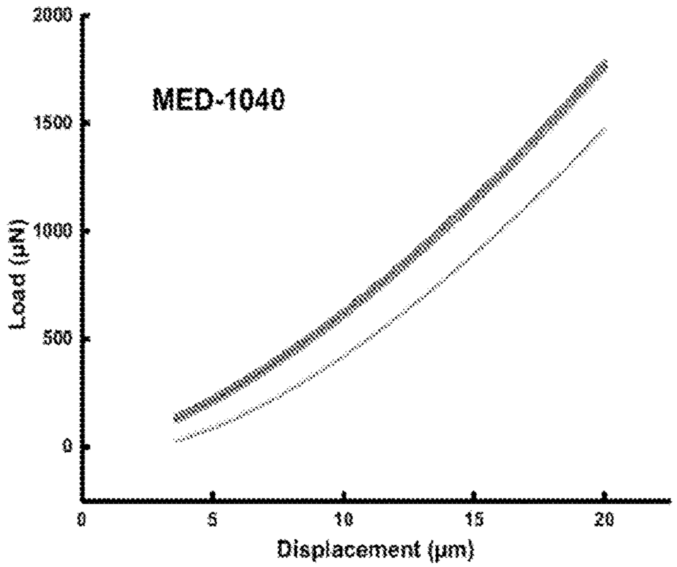
FIGS. 11A-11C show load-displacement curves from indentation tests on three different bio-compatible silicone materials.
Figure 11B:
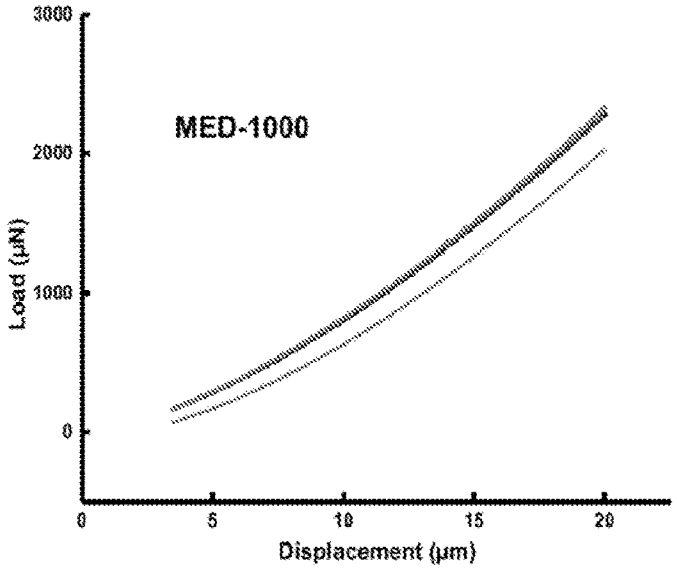
Figure 11C:
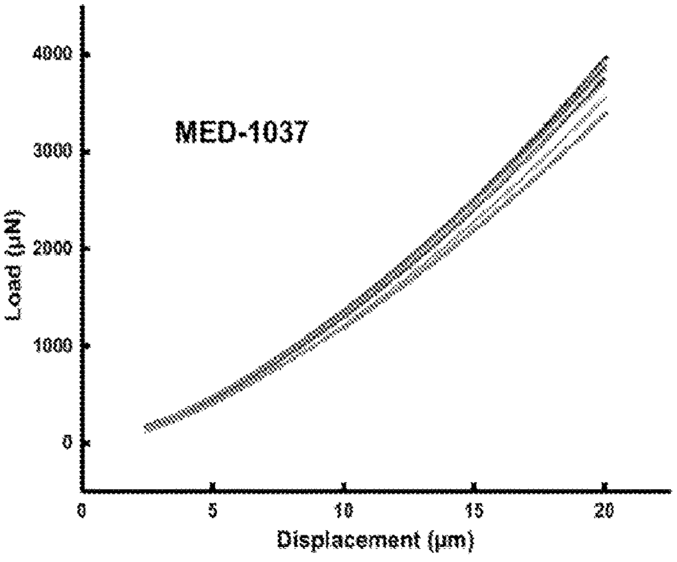

The compliant mechanical properties of the device minimize mechanical forces on adjacent biological tissues, for improved biocompatibility. Human skin has Young's modulus between ~400 to ~800 kPa, while human cardiac muscles have Young's moduli of ~100 kPa. The BLE module uses a biocompatible silicone (Silbione RTV 4420) for encapsulation, with a modulus in the range of human skin. The catheter oximeter probe uses three different biocompatible silicones (MED-1040, MED-1000, MED-1037, Avantor Inc), with Young's modulus values of 797, 1022 to 1667 kPa as in FIG. 3A, which measurement data are shown in FIGS. 11A-11C, suitable for different medical applications. Choices of the silicone and the diameter of the copper wire can be selected to achieve bending stiffnesses of 1.6, 1.8, 2.3 to 20 N/mm$^2$. By comparison, commercial catheter oximeters for central venous applications use optical fibers (e.g. Swan Ganz 777F8, Edwards Inc.) with bending stiffnesses of ~250 N/mm$^2$ (FIG. 3B), which is 10 to 200 times larger than those of devices reported here.

Figure 3C:
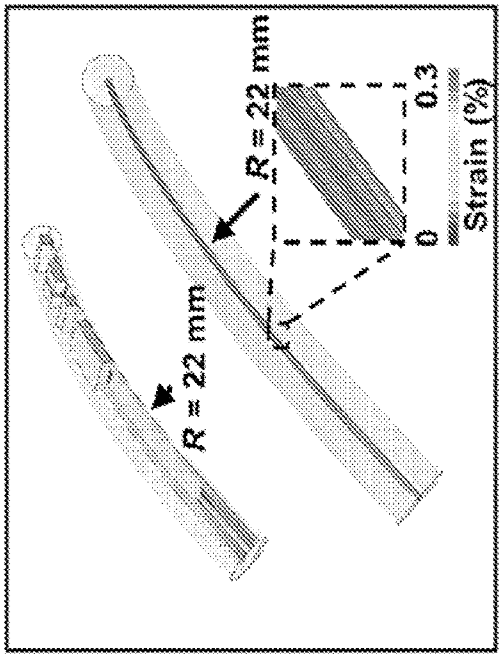
Figure 3D:
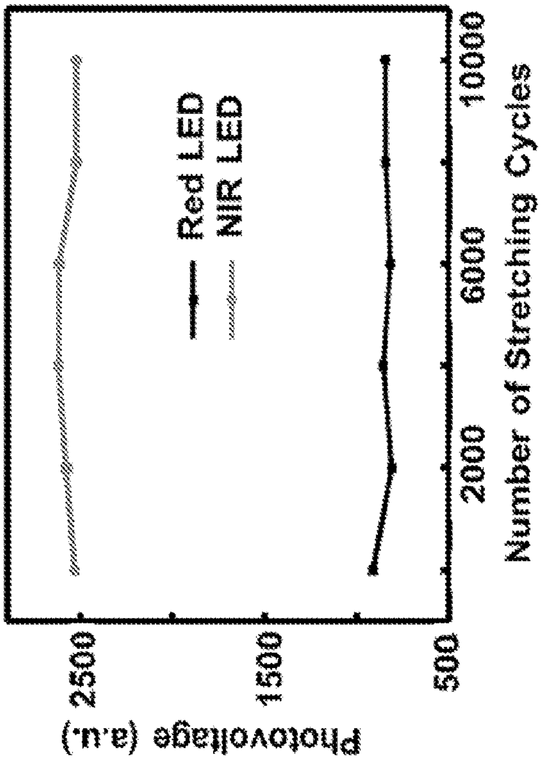
Figure 3E:
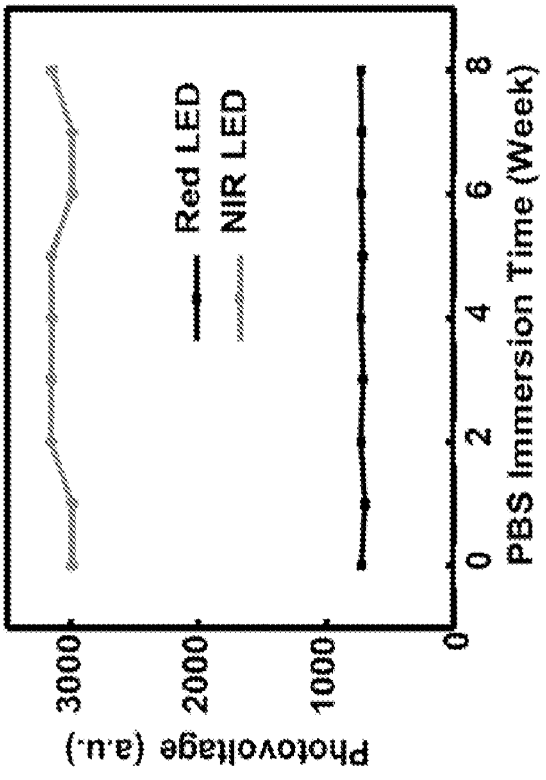
Figure 13A:
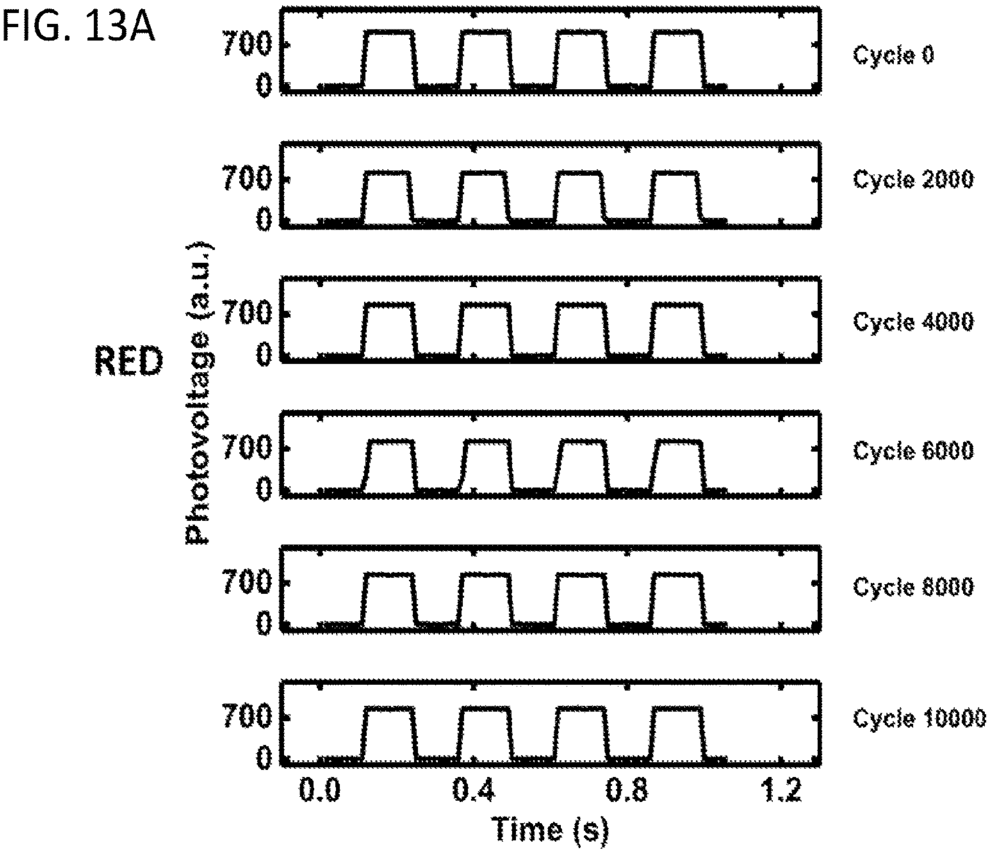
FIGS. 13A-13B show pulse signal emitted by the LED and measured by the photodiode, with catheter oximeter probe in different stretch cycles.
Figure 13B:
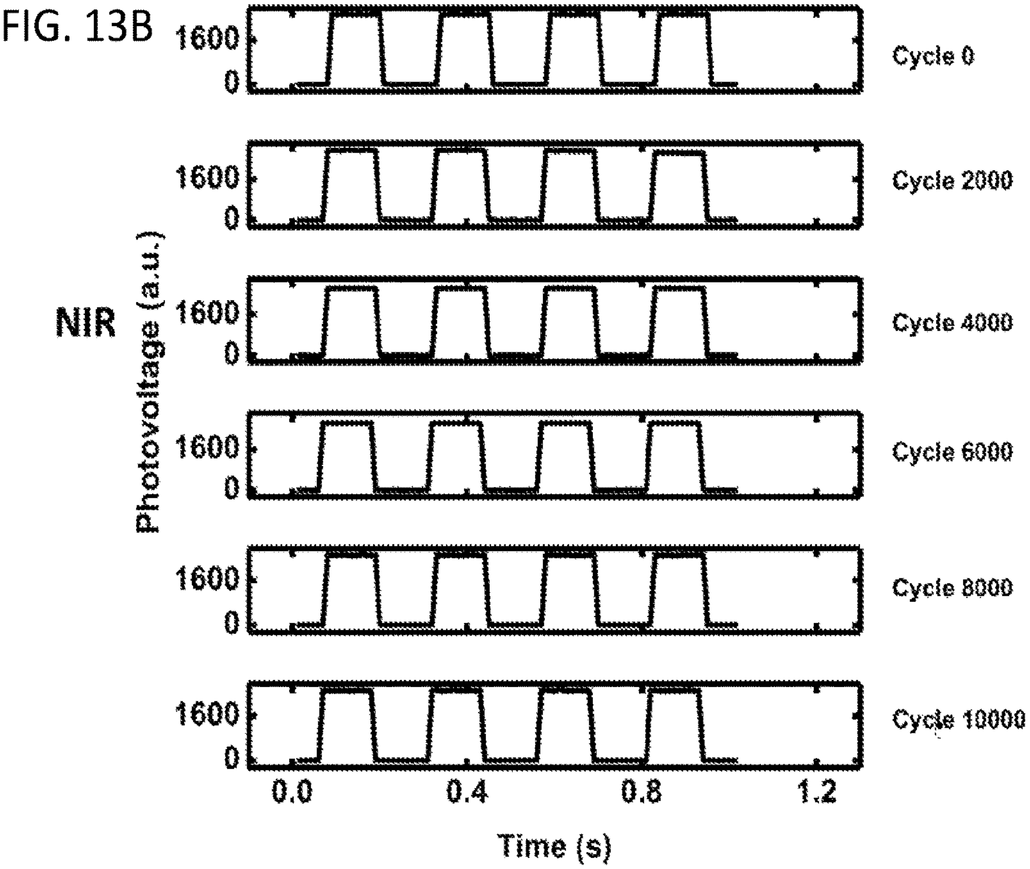
Figure 14A:
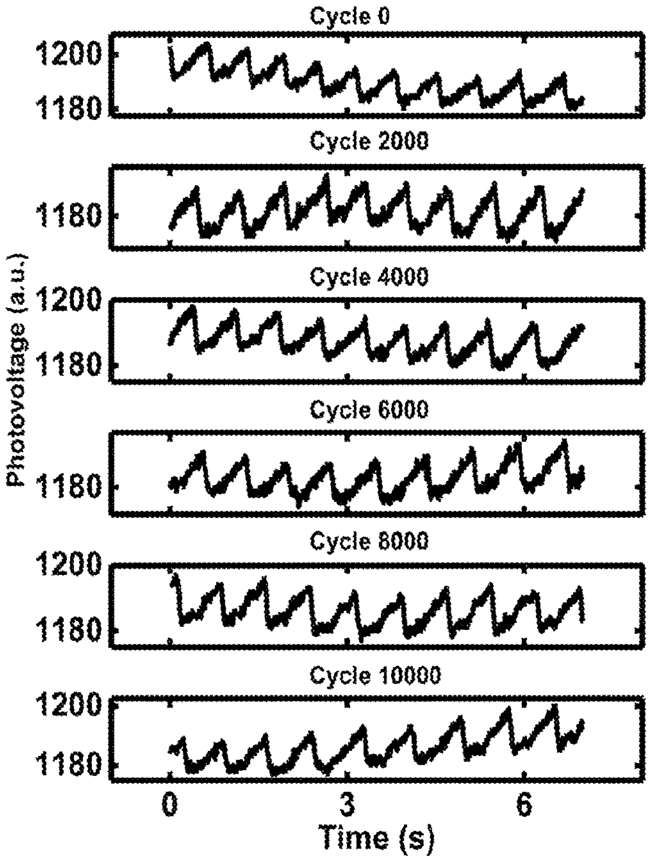
FIGS. 14A-14B show measured human pulse signal by wireless catheter oximeter, with the catheter probe after different stretch cycles. Human pulse signal from (FIG. 14A) Red, (FIG. B) NIR LEDs respectively.
Figure 14B:
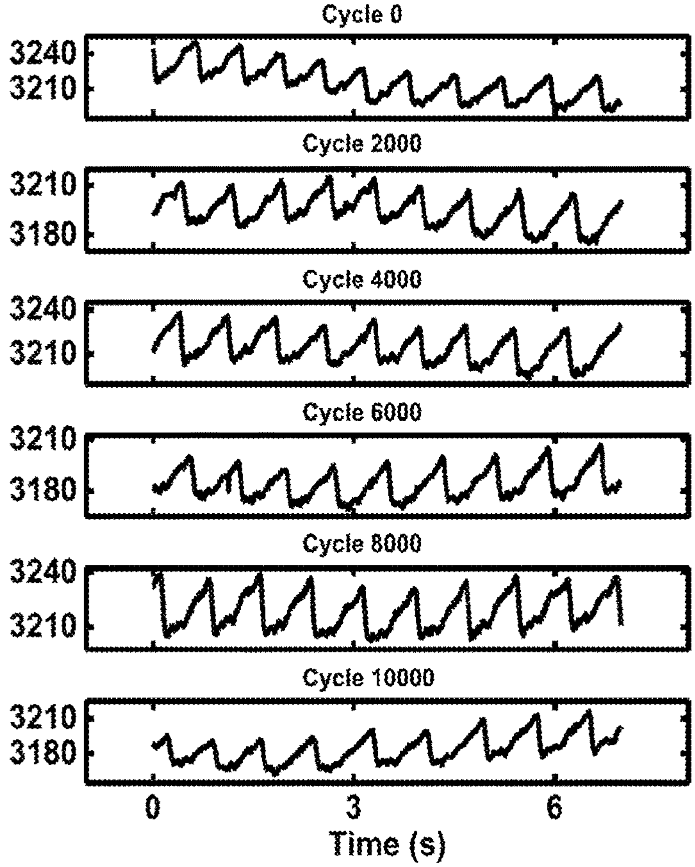
Figure 15:
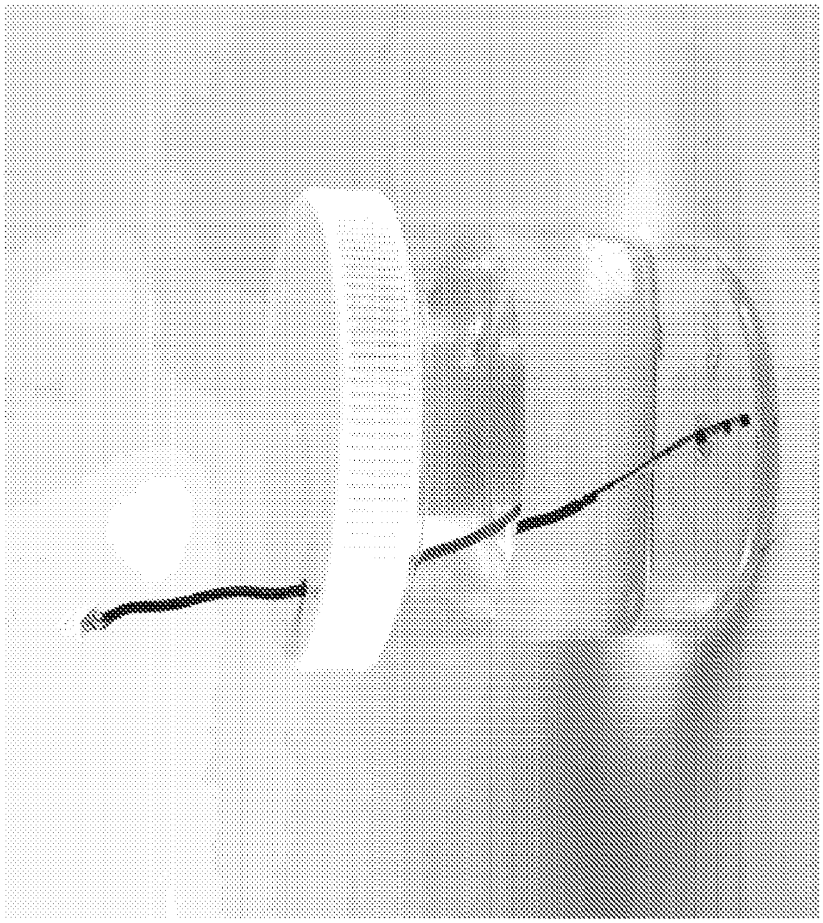
FIG. 15 shows an image of the setup for the phosphate-buffered saline (PBS) soak test. The catheter oximeter probe is immersed in PBS solution. The entire system is placed inside an oven at 37° C.
Figure 16B:
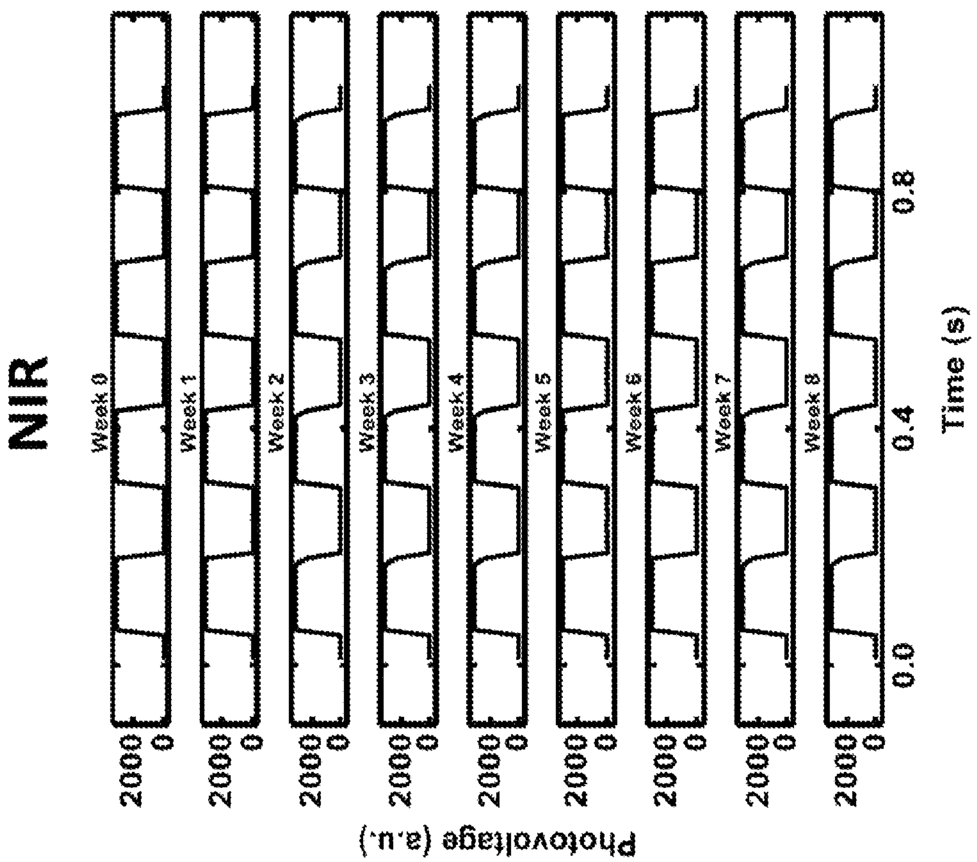
FIG. 16 shows pulsed emission from the LEDs and measured by the photodiode, with a catheter oximeter probe immersed for different times in phosphate-buffered saline (PBS) solution at 37° C. (A) Red and (B) NIR LED pulse signal at different immersion time.
Figure 16A:
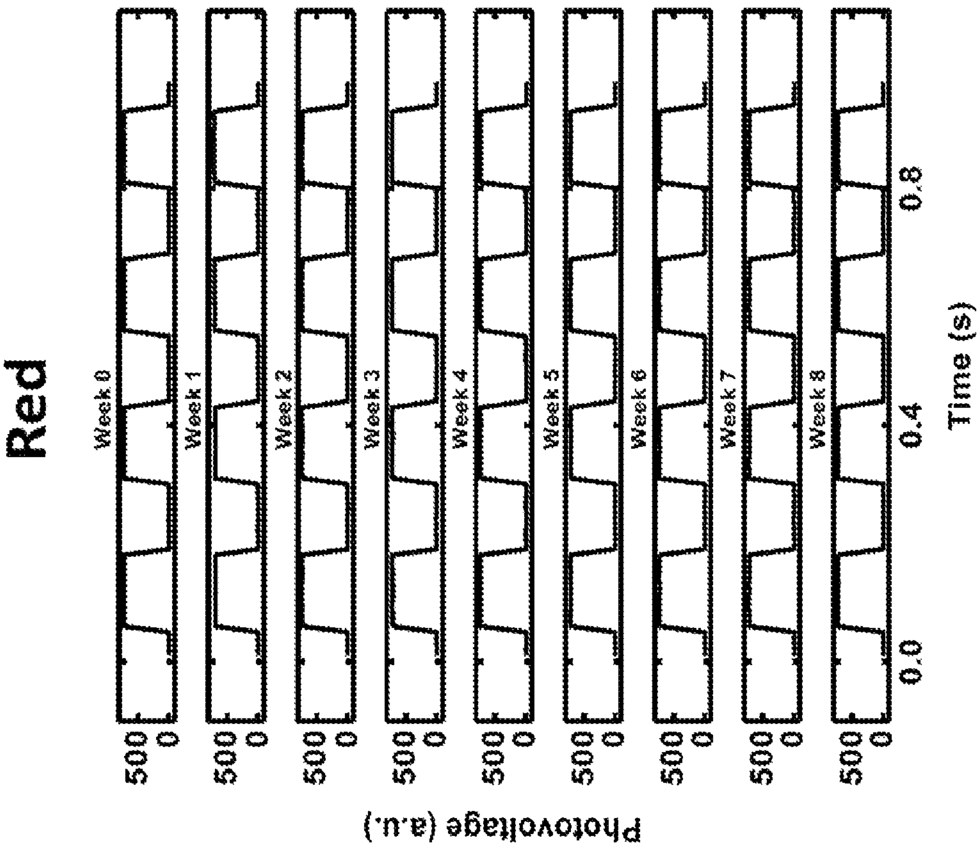
Figure 17B:
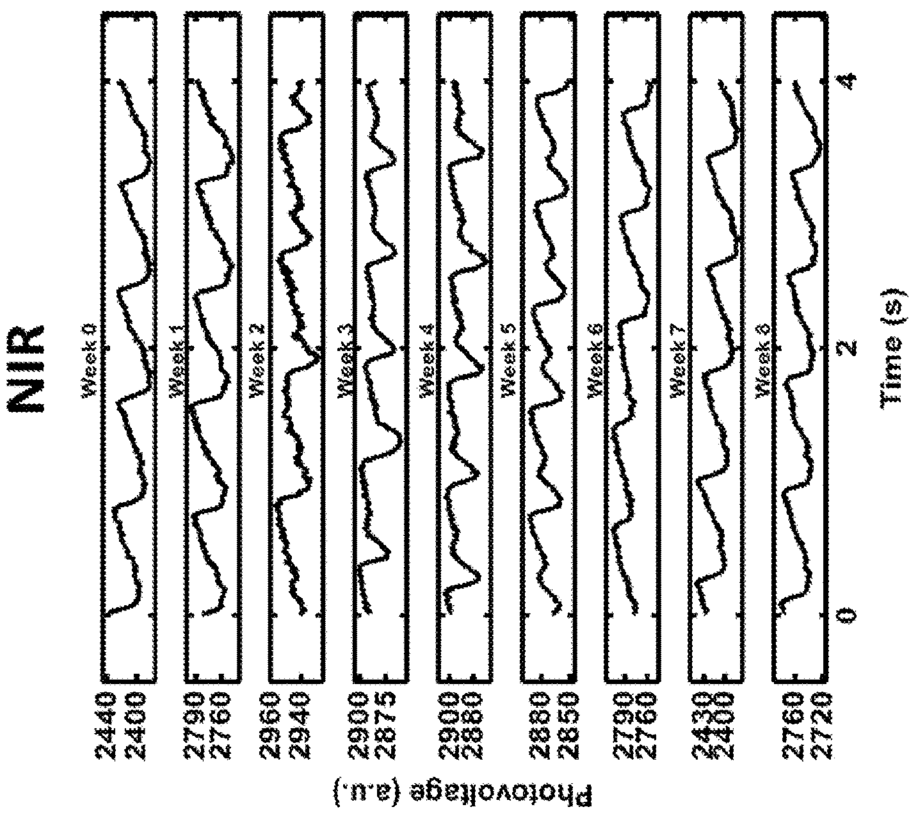
FIG. 17 shows measured human pulse signal captured by wireless catheter oximeter, with the catheter probe immersed for different times in phosphate-buffered saline (PBS) solution at 37° C. Human pulse signal from (A) Red, (B) NIR LEDs, respectively.
Figure 17A:
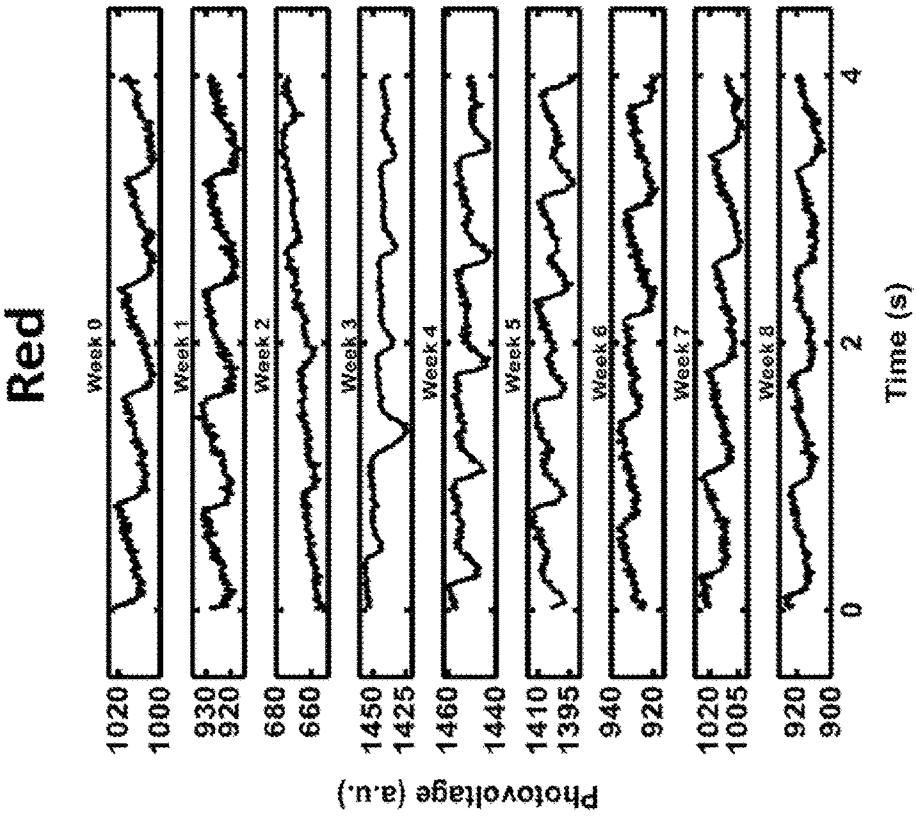

Results of FEA in FIG. 3C show that the strain distribution in copper remains below the copper elastic strain limit (0.3%) in the sensor probe and silicone-based catheter for an elastic bending radius of 22 mm and 27 mm, respectively. Studies indicate that bending to radii of 5 mm for more than 10,000 cycles leads to no change in the device performance (FIG. 12B). Specifically, FIG. 3D shows consistent photovoltages generated from the PD by operation of the red and NIR LEDs, with additional measurements inside an integrating sphere after various bending cycles, which measurement data are shown in FIGS. 13A-13B. FIGS. 14A-14B show signals generated from a finger, indicating stable performance over 10,000 bending cycles. The silicone encapsulation also provides an adequate barrier to biofluids. Immersion into a bath of phosphate-buffered saline (PBS) at 37° C. for 8 weeks (FIG. 15) induces a negligible change in device performance examined by both in vitro measurements inside the integrating sphere (FIGS. 3E and 16A-16B) and tests on the fingertips (FIGS. 17A-17B). The data shown in FIG. 3E use the same measurement approach as those in FIG. 3D. FIGS. 17A-17B uses the methods of FIGS. 14A-14B. All results indicate that the system supports stable performance over 8 weeks of immersion in PBS.

Figure 3F:
Figure 3G:
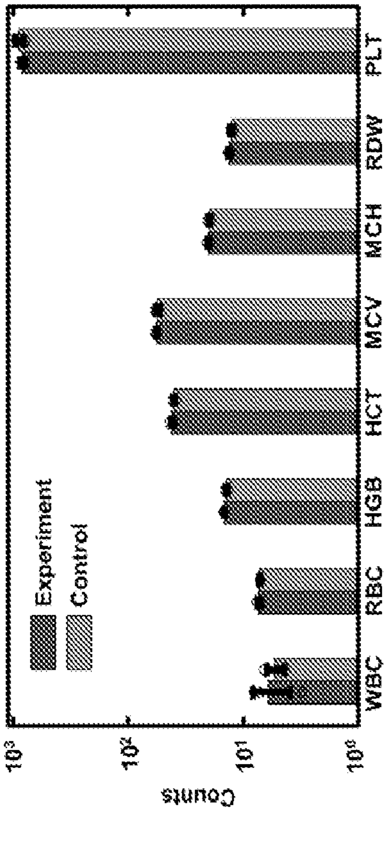
Figure 3H:
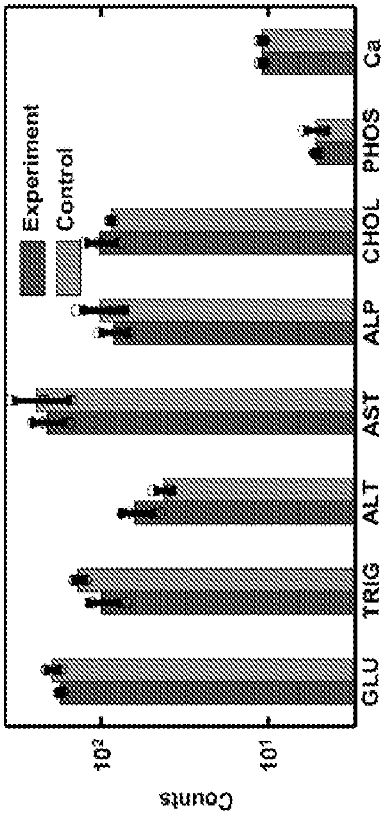

FIG. 3F presents a CT image of a mouse model 2 weeks after subdermal implantation of a device on the back near the spine. Analysis of complete blood count (FIG. 3G) and blood chemistry (FIG. 3H) for mice with implants for 30 days (labeled as Experiment) and mice without implants (labeled as Control) indicate no sign of organ damage or injury, and no change in the electrolyte or the enzyme balance. More measured parameters are presented in FIG. 18 (Details appear in the section of Materials and Methods).

Bench Tests

Mixed venous oxygen saturation ($SvO_2$) and central venous oxygen saturation ($ScvO_2$) are two essential diagnostic indicators. The former, measured in the pulmonary artery, reflects the global balance between oxygen delivery and consumption. The latter, measured via a central venous catheter, reflects principally the degree of oxygen extraction from the brain and the upper part of the body. Major surgeries, especially cardiac surgeries, rely on monitoring of $SvO_2$ and $ScvO_2$ with fiber optic oximeters (e.g. Swan Ganz series catheter and HemoSphere monitoring platform, Edwards LifeScience), to guide care. Such devices are implanted transvenously, where the fiber optics support the optical transmission from external sources and sensing of backscattered light using external detectors, thereby tethering the patient to bedside apparatus. FIGS. 3A-3B summarizes some advantages of the introduced wireless catheter probe in materials and mechanical properties, compared with a commercially available fiber optic probe, and FIGS. 4A-4B offer comparisons of optical performance and sensitivity of these two systems.

FIG. 4A (left) shows comparisons based on measurements obtained by placing both the wireless catheter oximetry probe and a commercial fiber optic oximetry catheter (Swan Ganz 777F8, Edwards Life Science Inc) in a fluorescent solution with 0.3 μM Alexa Fluor 647 (emission maximum at 672 nm when excited at 651 nm). The device introduced here involves a divergent illumination pattern normal to the surface of the LED and lateral to the long axis of the probe. By contrast, the commercial device exhibits a conical pattern of illumination with a low divergence angle centered at the tip of the fiber (FIG. 4A, left). Monte Carlo simulations of the light emission profiles for these two type sensors (FIG. 4A, right), are consistent with experimental results (FIG. 4A, left). The divergent and lateral emission features of the LED system maximize light-tissue coupling for a range of implantation sites, especially those that involve coupling to the surface of the heart. Moreover, the probe volume and probe depth can be adjusted through control over of light intensity and the distance between the LEDs and PD, to allow optimization for measurements of localized tissue oximetry on different sites of interest.

Figure 19:
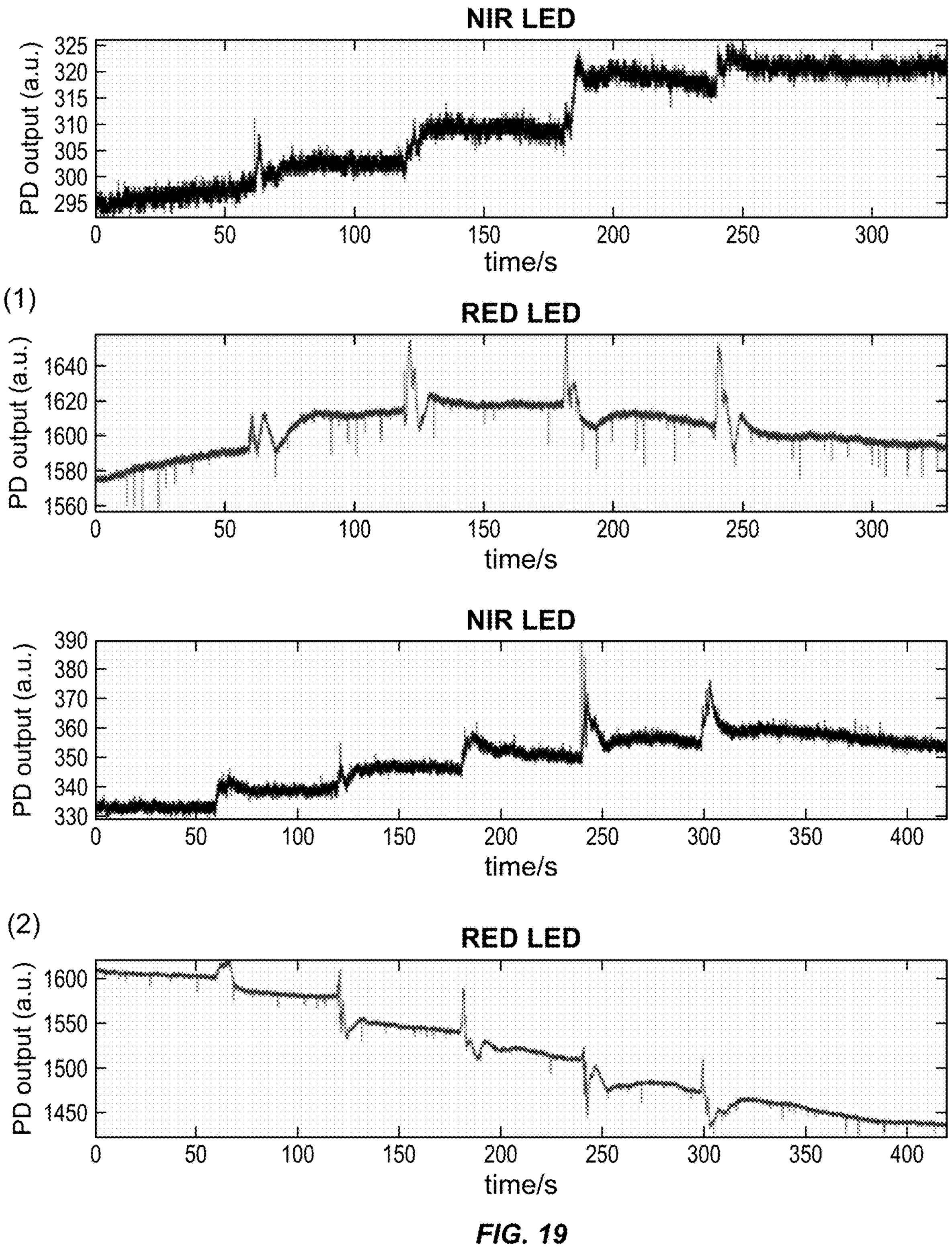
FIG. 19 shows raw data recorded from a wireless catheter oximeter in blood with time varying Hb/HbO, with comparison to measurements performed with a commercial (Edwards) oximeter.
Figure 19:
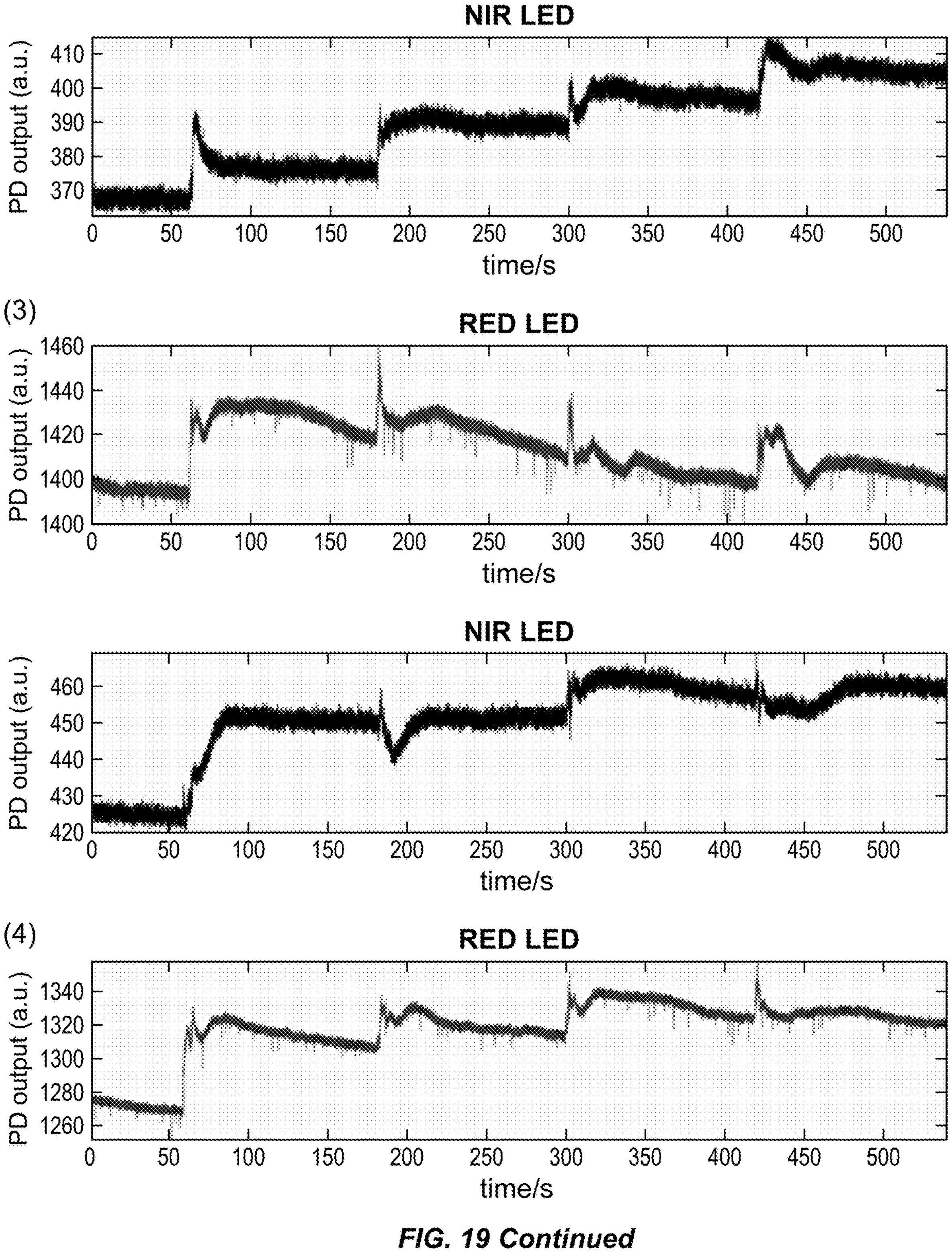

In vitro tests of the device with horse blood (Fisher Scientific) at various oxygenation levels yield results that agree well with those measured with the commercial system (FIG. 4B), with a correlation coefficient of 0.979. Adding sodium dithionite into the blood effectively transforms oxygenated hemoglobin into the deoxygenated form. The amount of sodium dithionite defines the oxygenation level, across a relevant range, which measurement and calculated data are shown in FIGS. 19 and 20A-20B, details on the measurements and calculation methods appear in Materials and Methods. The results demonstrate measurement capabilities for assessments of $SvO_2$ and $ScvO_2$ across relevant ranges.

Figure 4H:
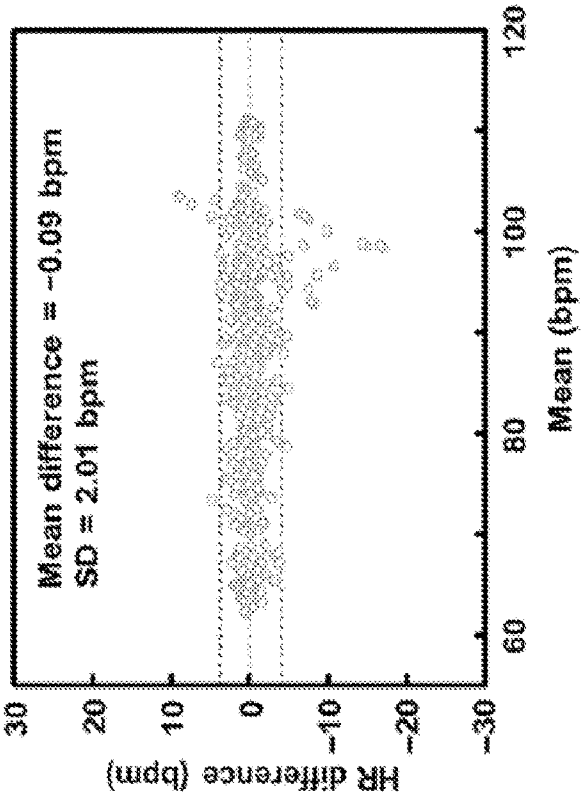
Figure 21B:
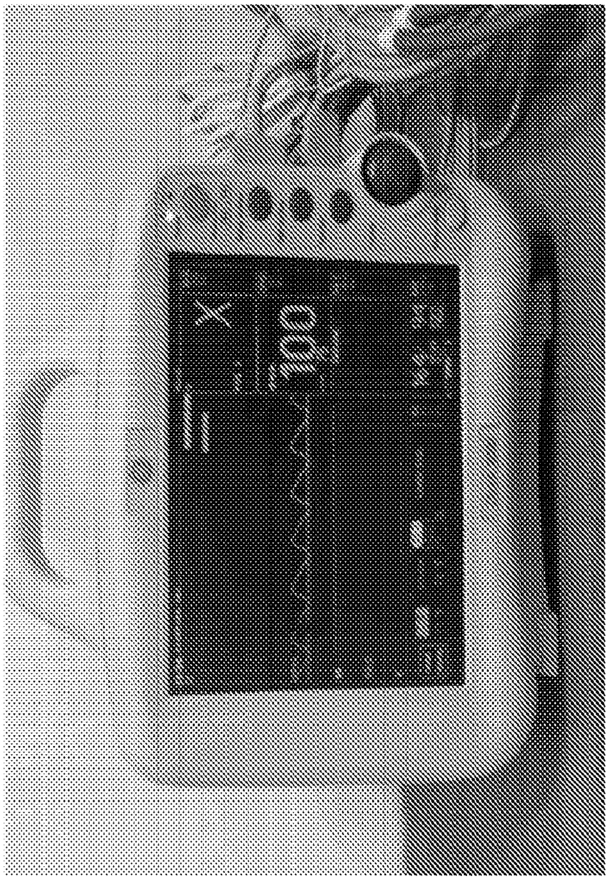
FIGS. 21A-21B show measurement method and the test platform for comparing the performance of a wireless catheter oximeter to a clinical standard pulse oximeter.
Figure 21A:
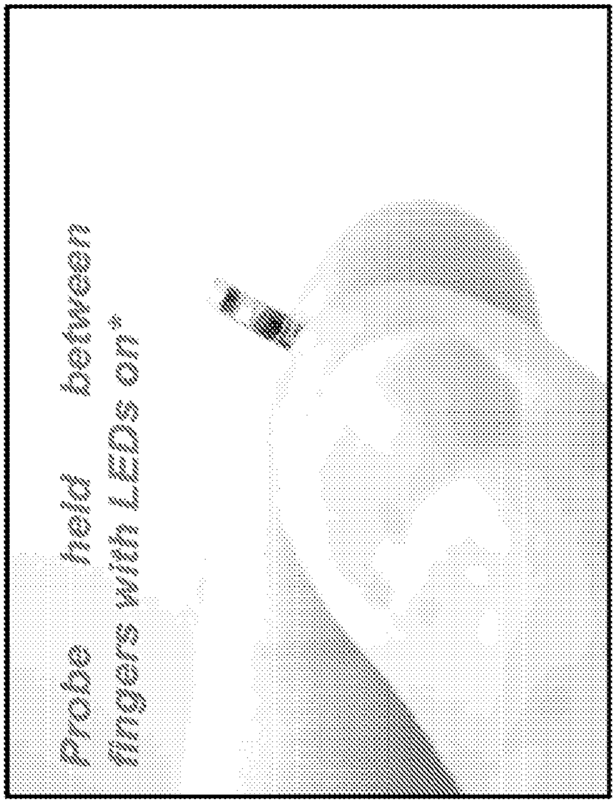

A simple demonstration involves measurements of pulse oxygen saturation by pressing the device onto an index finger (FIGS. 21A-21B), as raw pulse signal shown in FIG. 4C. Standard postprocessing algorithms based on the Beer-Lambert law (FIG. 4D) yield the pulse oxygen saturation ($SpO_2$) and HR (with the algorithms described in detail in the section of Materials and Methods). FIGS. 4E-4F present results from a subject during a period of rest followed by a breath holding and then another period of rest. The data match well with those determined with a clinical pulse oximeter (DASH 3000 Patient Monitor, General Electronic Inc.) attached onto the other finger. Additional independent experiments on different subjects appear in FIG. 22. The Bland-Altman plot shown in FIGS. 4G-4H highlights excellent agreement between the wireless catheter oximeter and the clinical gold standard oximeter in measuring pulse oximetry and HR. With a total of 801 data points on four independent subjects, the 95% confidence interval for $SpO_2$ is [−3.61 to 3.90] and for HR is [−4.05 to 3.85] bpm (breaths per minute).

In Vivo Studies

Figure 5B:
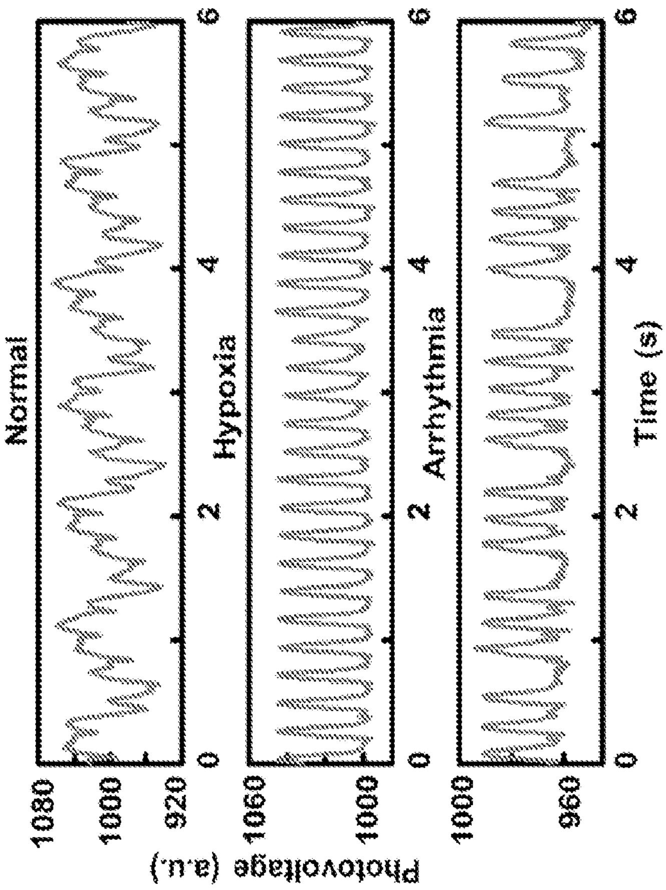
Figure 5A:
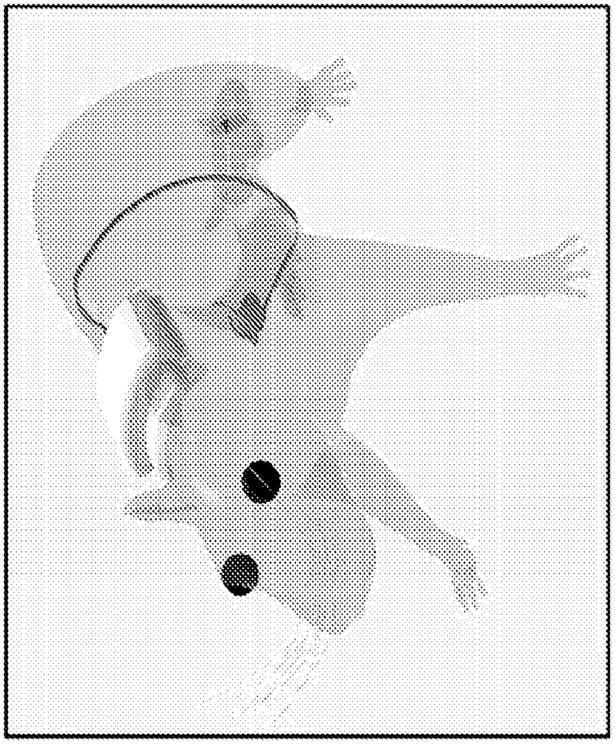
Figure 6:
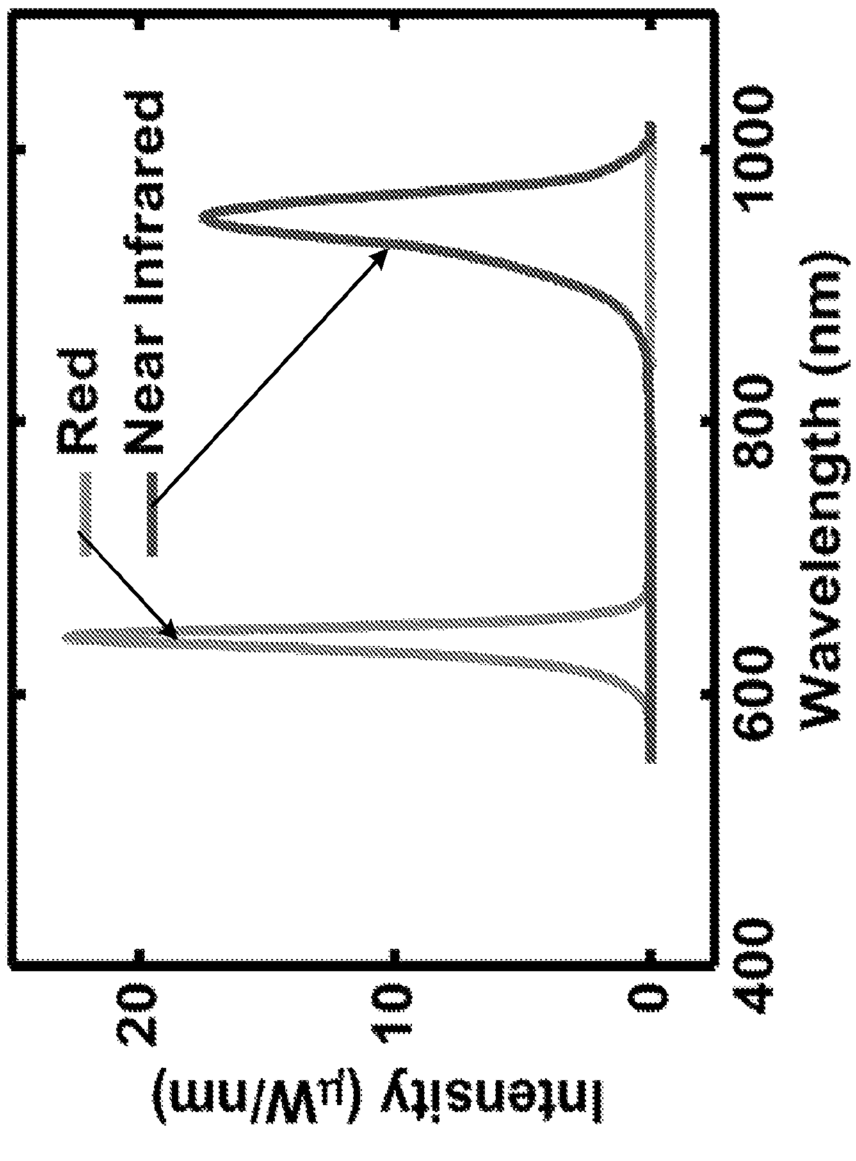
FIG. 6 shows measured spectra for the red and near-infrared (NIR) LEDs of the sensing probes. The measured spectral bandwidths are 34 nm and 53 nm for red and NIR LED, respectively.
Figure 23A:
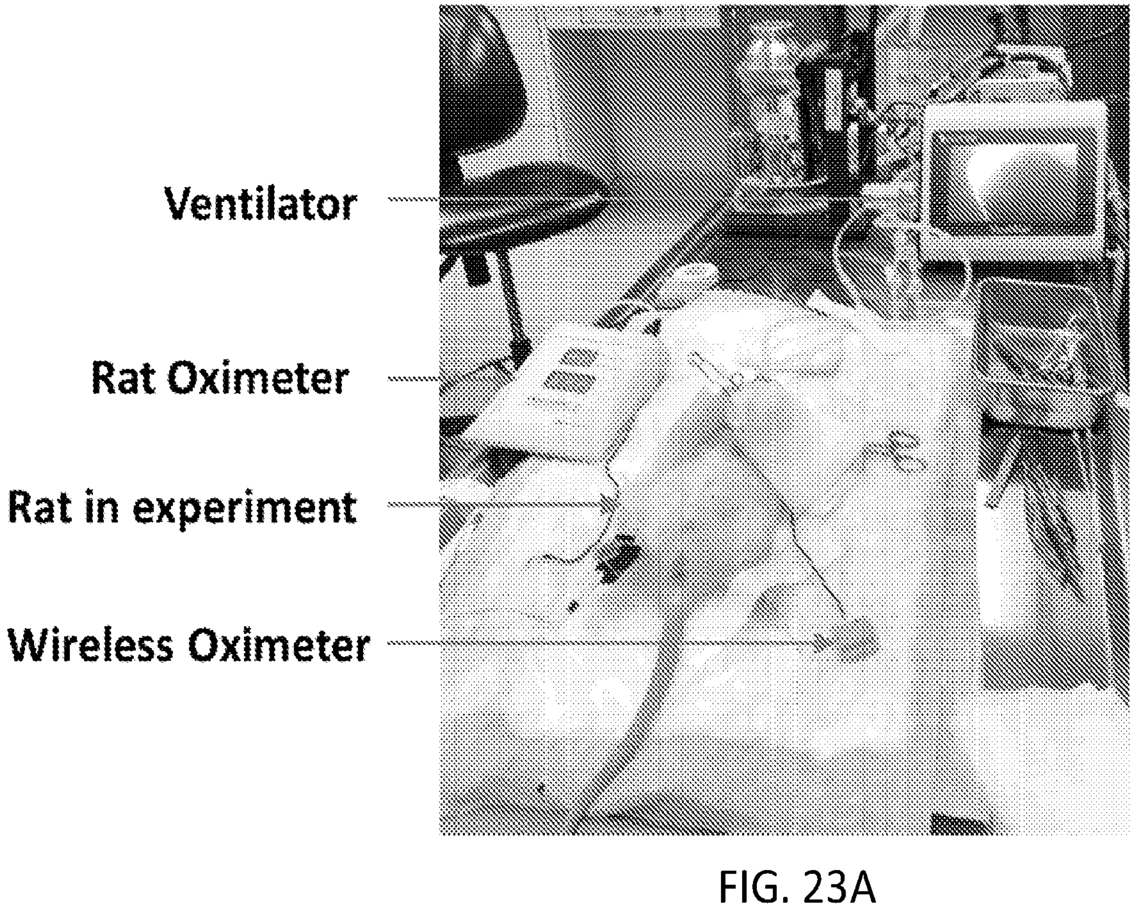
FIGS. 23A-23B show animal experiment platform.
Figure 23B:
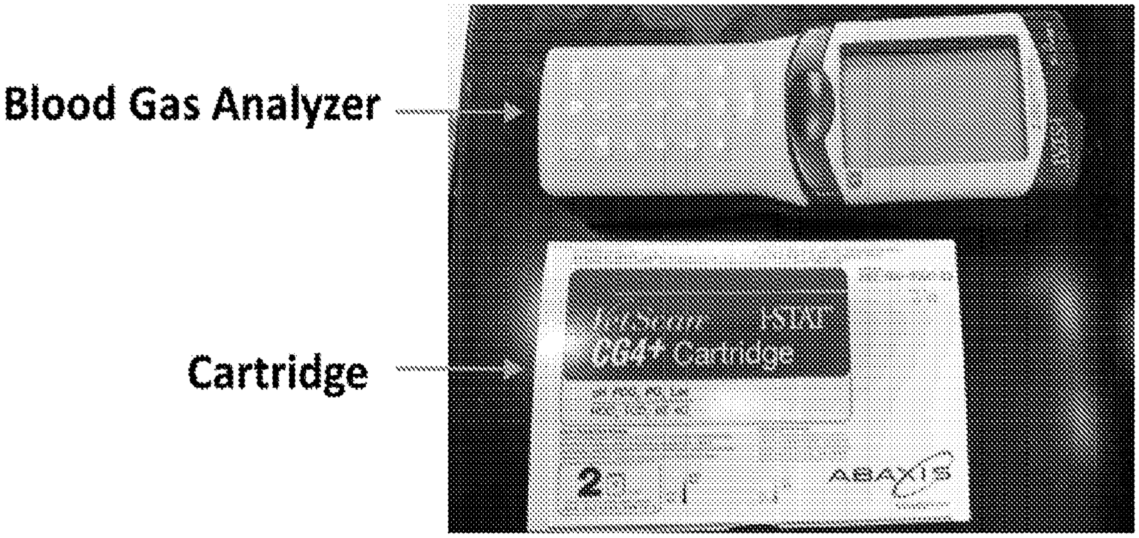

The primary envisioned application of the technology introduced here is in the context of pediatric cardiac surgery and recovery, where sutures hold the probe against the surface of major cardiac vessels for real-time monitoring of oxygen saturation within that vessel during the early and critical postoperative period of several days. Experiments on rat models, as illustrated in FIG. 5A, demonstrates the key features. FIGS. 23A-23B shows some details. The implantation procedures appear in the section of Materials and Methods. Sutures hold the probe to the anterior wall of the left ventricle (with thickness of ~2.6 mm) close to the left anterior descending coronary artery. Adjustments of the ventilation rate and tidal volume on the ventilator allow induced hypoxia and arrhythmias, for purposes of testing. As shown in FIG. 5B, the device captures changes in heart rate, respiration rate, ischemia, and arrhythmias (n=6 biologically independent rats, signal labeled as Normal, Hypoxia, and Arrhythmia, respectively). FIG. 5C highlights the signals associated with probing with red and NIR light, each of which shows expected waveforms, along with calculated respiration rate (RR) and heart rate (HR) from these signals (n=6 rats/group). The RR follows the ventilator machine settings i.e. 66 breaths per minute (bpm) in the beginning, 38 bpm in middle, and back to 66 bpm until the end, while the HR follows a normal value for rats. FIG. 5D summarizes calculated cardiac pulse oxygenation levels that can be captured by the implanted wireless sensing system. FIG. 5E presents results for cardiac oxygenation (n=4 biologically independent rats) and comparisons against measurements performed with a commercial blood gas analyzer using samples of blood from the left ventricle, starting with the initial phases of the open chest experiment. The high degree of correlation (Pearson correlation=0.971) demonstrates that the device offers sufficient sensitivity and precision in real-time oxygenation monitoring for use during cardiac surgery and associated surgical recovery. Details on the measurements and signal processing algorithm appear in the section of Materials and Methods.

Discussion

The results presented here include design features, feasibility testing, and validation data for an implantable optoelectronic system tailored for use in cardiovascular monitoring, specifically in the context of surgical operations. The designs yield devices that are mechanically compliant and water resistant. This millimeter-scale, wireless optoelectronic platform enables chronic, continuous, precision sensing of intravascular or intracardiac oxygen saturation, free from the entanglement by conventional catheter oximeters. The advancement in mechanical compliance and material softness, compared with fiber-optic catheter, suggests opportunities in mitigating the complications seen by old technology. Moreover, the lateral mode of illumination maximizes light-tissue coupling, allowing a range of implantation sites including blood vessel and cardiac tissue. Comparison test and validation studies on blood samples, on human fingertips, and on cardiac surfaces in live animal models indicate measurement performance comparable to that of clinical standard oximeters and with values that match those determined with a blood gas analyzer.

The values of cardiac oxygenation saturation detected using the platforms described here correlate with the oxygenation of left ventricular blood measured using a blood gas analyzer in experiments on anesthetized rats. The wall thickness of the left ventricle in rats is 1.5 to 2.8 mm. With a penetration depth of 4 to 5 mm in muscular tissues, light can pass through the entire transmural extent of left ventricular wall to detect the oxygen saturation of the blood inside. As mentioned previously, the penetration depth can be changed by adjusting the optical power. Future studies will examine the efficacy and reliability of the catheter-type oximeter in quantifying the oxygen saturation of the heart, superior vena cava, and main pulmonary artery in larger animals and patients undergoing open-heart surgery.

These in vivo results must, however, be interpreted within the constraints of a few potential limitations. In addition to intracardiac oxygen saturation, oxygenation levels of the superior vena cava or main pulmonary artery are important in open-heart surgery. The small-animal studies here prevent evaluations of capabilities in such anatomic locations. Additional work is necessary to test the accuracy and efficacy of the device in these major vascular locations acutely, and after the chest is closed in larger animals. The small-animal studies also prevent in vivo chronic demonstration of the reported device. Systematic examination of the inflammatory responses associated with subdermal implantation of the optical probes reveals no observable increases in leukocytes, indicating negligible inflammatory response (FIGS. 3G-3H). Experiments to examine effects with large-animal models are a subject of ongoing work. Another research direction is to examine further, through in vivo experiments, the mechanical compliance of the presented catheter and associated capabilities for mitigating complications often encountered with conventional fiber-optic systems, such as blood vessel damage, infection, and thrombosis. Other possibilities for future work include incorporation of multiple LEDs and additional wavelengths for additional measurement capabilities and by integrating collections of PDs for depth profiling. Additional options are in combinations with sensors of pressure and flow or for drug delivery, using concepts adapted from those recently reported for animal experiments in neuroscience.

In conclusion, the present study indicates that a flexible, thin, catheter-type oximeter can accurately monitor venous and cardiac oxygenation levels in real time. Specifically, results demonstrate that this millimeter-scale, wireless optoelectronic platform can detect cardiac oxygenation saturation in rats during open-heart surgery. To explore the potential of the device to monitor oxygenation levels in main vessels, further studies will focus on the efficacy and reliability for detecting the oxygenation saturation in the superior vena cava and main pulmonary artery of large animals, mimicking open-heart surgery of patients.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein. Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

[1]. F. Bloos, K. Reinhart, Venous oximetry. *Intensive Care Med* 31, 911-913 (2005).

[2]. J. Frazier, Theory and clinical application of continuous fiberoptic central venous oximetry (scvo2) monitoring. *Critical Care Marketing and Education, Edwards Lifesciences*, (2009).

[3]. J. L. Waller, et al., Clinical evaluation of a new fiberoptic catheter oximeter during cardiac surgery. *Anesth Analg* 61, 676-679 (1982).

[4]. O. J. Liakopoulos, et al., An experimental and clinical evaluation of a novel central venous catheter with integrated oximetry for pediatric patients undergoing cardiac surgery. *Anesth Analg* 105, 1598-1604, table of contents (2007).

[5]. G. Marx, K. Reinhart, Venous oximetry. *Curr Opin Crit Care* 12, 263-268 (2006).

[6]. R. Pearse, A. Rhodes, "Mixed and central venous oxygen saturation" in *Yearbook of Intensive Care and Emergency Medicine* 2005 (Springer, 2005), pp. 592-602.

[7]. M. L. Landsman, et al., A fiberoptic reflection oximeter. *Pflügers Archly* 373, 273-282 (1978).

[8]. S. D. Goldring. (Google Patents, 1987).

[9]. B. Boville, et al., Irvine, Quick Guide to Pediatric Cardiopulmonary Care. (2011).

[10]. D. C. McGee, M. K. Gould, Preventing complications of central venous catheterization. *New England journal of medicine* 348, 1123-1133 (2003).

[11]. E. M. Kagel, G. M. Rayan, Intravenous catheter complications in the hand and forearm. *Journal of Trauma and Acute Care Surgery* 56, 123-127 (2004).

[12]. A. Bowdle, Vascular complications of central venous catheter placement: evidence-based methods for prevention and treatment. *Journal of cardiothoracic and vascular anesthesia* 28, 358-368 (2014).

[13]. H. S. Vats, Complications of catheters: tunneled and nontunneled. *Advances in chronic kidney disease* 19, 188-194 (2012).

[14]. C. Kornbau, et al., Central line complications. *International Journal of Critical Illness and Injury Science* 5, 170 (2015).

[15]. H. U. Chung, et al., Binodal, wireless epidermal electronic systems with in-sensor analytics for neonatal intensive care. *Science* 363, eaau0780 (2019).

[16]. K. Lee, et al., Mechano-acoustic sensing of physiological processes and body motions via a soft wireless device placed at the suprasternal notch. *Nature biomedical engineering,* 1-11 (2019).

[17]. S. Y. Heo, et al., Wireless, battery-free, flexible, miniaturized dosimeters monitor exposure to solar radiation and to light for phototherapy. *Sci Transl Med* 10, eaau1643 (2018).

[18]. X. Yu, et al., Skin-integrated wireless haptic interfaces for virtual and augmented reality. *Nature* 575, 473-479 (2019).

[19]. K. Kwon, et al., Miniaturized, light-adaptive, wireless dosimeters autonomously monitor exposure to electromagnetic radiation. *Science Advances* 5, eaay2462 (2019).

[20]. H. Zhang, et al., Wireless, battery-free optoelectronic systems as subdermal implants for local tissue oximetry. *Science advances* 5, eaaw0873 (2019).

[21]. J. Kim, et al., Miniaturized Battery-Free Wireless Systems for Wearable Pulse Oximetry. *Adv Funct Mater* 27, 1604373 (2017).

[22]. Y. Mendelson, B. D. Ochs, Noninvasive pulse oximetry utilizing skin reflectance photoplethysmography. *IEEE Transactions on Biomedical Engineering* 35, 798-805 (1988).

[23]. J. L. Reuss, Multilayer modeling of reflectance pulse oximetry. *IEEE Trans Biomed Eng* 52, 153-159 (2005).

[24]. E. D. Chan, et al., Pulse oximetry: understanding its basic principles facilitates appreciation of its limitations. *Respiratory medicine* 107, 789-799 (2013).

[25]. M. Nitzan, A. Romem, R. Koppel, Pulse oximetry: fundamentals and technology update. *Medical Devices (Auckland, NZ)* 7, 231 (2014).

[26]. P. Scott, in *Oregon Medical Laser Center*. (1999).

[27]. TEMD7000X01 datasheet. www.vishay.com Rev. 1.6, (February 2015).

[28]. L. Wang, S. L. Jacques, Monte Carlo modeling of light transport in multi-layered tissues in standard C. *The University of Texas, MD Anderson Cancer Center, Houston,* 4-11 (1992).

[29]. A. N. Bashkatov, et al., Optical Properties of Skin, Subcutaneous, and Muscle Tissues: A Review. *J Innov Opt Heal Sci* 4, 9-38 (2011).

[30]. A. Bouchama, J. P. Knochel, Heat stroke. *N Engl J Med* 346, 1978-1988 (2002).

[31]. C. G. Crandall, T. E. Wilson, Human cardiovascular responses to passive heat stress. *Comprehensive Physiology* 5, 17-43 (2011).

[32]. P. G. Agache, et al., Mechanical properties and Young's modulus of human skin in vivo. *Arch Dermatol Res* 269, 221-232 (1980).

[33]. A. Kalra, et al., An overview of factors affecting the skins Youngs modulus. *Journal of Aging Science*, (2016).

[34]. A. B. Mathur, et al., Endothelial, cardiac muscle and skeletal muscle exhibit different viscous and elastic properties as determined by atomic force microscopy. *J Biomech* 34, 1545-1553 (2001).

[35]. P. Ingelmo, M. Barone, R. Fumagalli, Importance of monitoring in high risk surgical patients. *Minerva Anestesiol* 68, 226-230 (2002).

[36]. K. Reinhart, et al., Continuous central venous and pulmonary artery oxygen saturation monitoring in the critically ill. *Intensive Care Med* 30, 1572-1578 (2004).

[37]. R. M. McAdams, et al., Left ventricular hypertrophy is prevalent in Sprague ODawley rats. *Comparative medicine* 60, 357-363 (2010).

[38]. S. E. Litwin, et al., Serial echocardiographic assessment of left ventricular geometry and function after large myocardial infarction in the rat. *Circulation* 89, 345-354 (1994).

[39]. L. E. Watson, et al., Baseline echocardiographic values for adult male rats. *Journal of the American Society of Echocardiography* 17, 161-167 (2004).

[40]. J. Shin, et al., Bioresorbable pressure sensors protected with thermally grown silicon dioxide for the monitoring of chronic diseases and healing processes. *Nat Biomed Eng* 3, 37-46 (2019).

[41]. S. M. Won, et al., Multimodal Sensing with a Three-Dimensional Piezoresistive Structure. *ACS Nano* 13, 10972-10979 (2019).

[42]. S. R. Krishnan, et al., Epidermal electronics for noninvasive, wireless, quantitative assessment of ventricular shunt function in patients with hydrocephalus. *Sci Transl Med* 10, eaat8437 (2018).

[43]. R. C. Webb, et al., Epidermal devices for noninvasive, precise, and continuous mapping of macrovascular and microvascular blood flow. *Sci Adv* 1, e1500701 (2015).

[44]. Y. Zhang, et al., Battery-free, lightweight, injectable microsystem for in vivo wireless pharmacology and optogenetics. *Proc Natl Acad Sci USA* 116, 21427-21437 (2019).

[45]. Y. Zhang, et al., Battery-free, fully implantable optofluidic cuff system for wireless optogenetic and pharmacological neuromodulation of peripheral nerves. *Sci Adv* 5, eaaw5296 (2019).

[46]. J. W. Jeong, et al., Wireless Optofluidic Systems for Programmable In Vivo Pharmacology and Optogenetics. *Cell* 162, 662-674 (2015).

[47]. J. Ahrens, B. Geveci, C. Law, Paraview: An end-user tool for large data visualization. *The visualization handbook* 717, (2005).

[48]. J. M. Stujenske, et al., Modeling the Spatiotemporal Dynamics of Light and Heat Propagation for In Vivo Optogenetics. *Cell Rep* 12, 525-534 (2015).

[49]. I. Baotic, et al., Isoflurane favorably modulates guanosine triphosphate cyclohydrolase-1 and endothelial nitric oxide synthase during myocardial ischemia and reperfusion injury in rats. *Anesthesiology* 123, 582-589 (2015).

[50]. Y. Liu, et al., Vascular endothelial growth factor regulation of endothelial nitric oxide synthase phosphorylation is involved in isoflurane cardiac preconditioning. *Cardiovascular research* 115, 168-178 (2019).

[51]. A. Sassaroli, S. Fantini, Comment on the modified Beer-Lambert law for scattering media. *Phys Med Biol* 49, N255-257 (2004).

[52]. W. G. Zijlstra, et al., Absorption spectra of human fetal and adult oxyhemoglobin, de-oxyhemoglobin, carboxyhemoglobin, and methemoglobin. *Clin Chem* 37, 1633-1638 (1991).

[53]. F. Fabbri, et al., Optical measurements of absorption changes in two-layered diffusive media. *Phys Med Blot* 49, 1183-1201 (2004).

[54]. J. L. Kohl, et al., UVCS/SOHO empirical determinations of anisotropic velocity distributions in the solar corona. *Astrophys J*501, L127-L131 (1998).

[55]. F. Scholkmann, et al., End-tidal CO2: An important parameter for a correct interpretation in functional brain studies using speech tasks. *Neuroimage* 66, 71-79 (2013).

[56]. Signs & Symptoms of Anemia in Horses. https://www.succeed-equine.com/, (February 2014).

[57]. W. Bai, et al., Bioresorbable photonic devices for the spectroscopic characterization of physiological status and neural activity. *Nature biomedical engineering* 3, 644-654 (2019).

The invention claimed is:

1. An optoelectronic system, comprising:

an optoelectronic probe operably attached to a target region of a subject; and an electronic module coupled with the optoelectronic probe for wireless, real-time, and continuous measurements of physiological information of the subject, wherein the optoelectronic probe comprises a low modulus, flexible catheter with a probe tip comprising an optoelectronic sensor directly mounted onto a flexible printed circuit board (fPCB) in a geometry of a narrow, thin strip that detachably and electrically connects to the electronic module; and wherein the optoelectronic sensor comprises optical stimulation and sensing components, and optical blocking modules, and wherein the optical stimulation and sensing components comprise at least two light-emitting diodes (LEDs) and at least one photodiode (PD) configured for lateral emission and detection relative to a long axis of the flexible catheter.

2. The optoelectronic system of claim 1, wherein the narrow, thin strip has a width in a range of about 0.5-2 mm, a thickness in a range of about 50-180 μm, and a length in a range of about 5-20 mm.

3. The optoelectronic system of claim 1, wherein the fPCB comprises a flexible substrate and conductive traces, pads and outline defined on the flexible substrate.

4. The optoelectronic system of claim 3, wherein the flexible substrate is formed of a flexible material.

5. The optoelectronic system of claim 1, wherein the at least two LEDs and the at least one PD are surface mount (SMT) electronic components that are placed and attached onto the fPCB using reflow soldering.

6. The optoelectronic system of claim 1, wherein the at least two LEDs comprises a red LED with a peak emission wavelength in a range of about 600-700 nm and an infrared LED with a peak emission wavelength in a range of about 850-1050 nm.

7. The optoelectronic system of claim 6, wherein the optoelectronic probe further comprises one or more LEDs with peak emission wavelengths different from that of the red LED and the IR LED for additional measurement capabilities.

8. The optoelectronic system of claim 1, wherein the optical stimulation and sensing components are arranged in a lateral configuration such that the LEDs have divergent and lateral emission features that maximize light-tissue coupling for a range of implantation sites including blood vessel and cardiac tissue.

9. The optoelectronic system of claim 8, wherein the at least two LEDs are positioned laterally to a long axis of the probe.

10. The optoelectronic system of claim 9, wherein the PD is positioned to be equidistant to the two LEDs at a distance selected to balance sensing depth, probing volume, and signal to noise ratio.

11. The optoelectronic system of claim 10, wherein the probe volume and probe depth are operably adjusted through control over of light intensity of the LEDs and the distance between the LEDs and PD, to allow optimization for measurements of localized tissue oximetry on different sites of interest.

12. The optoelectronic system of claim 10, wherein the distance is in a range of about 1-3 mm.

13. The optoelectronic system of claim 1, wherein the optical blocking modules comprise at least two light-blocking structures for eliminating parasitic transmission of light from the LEDs directly to the PD without passing through surrounding tissues of interest.

14. The optoelectronic system of claim 13, wherein at least two light-blocking structures comprise two opaque silicone-based cuboid structures.

15. The optoelectronic system of claim 13, wherein one of the light-blocking structures is positioned between the PD and one side of the LEDs, and the other of the light-blocking structures is positioned at the probe tip close to the other side of the LEDs.

16. The optoelectronic system of claim 1, wherein a small plug-in connector serves as an electrical interface between the optoelectronic probe and the electronic module and allows battery recharge using a wired interface.

17. The optoelectronic system of claim 1, wherein a medical-grade, biocompatible silicone fully encapsulates the optoelectronic probe to define the low modulus, flexible catheter having a cylindrical shape and smooth surface that facilitates surgical manipulation and insertion.

18. The optoelectronic system of claim 17, wherein the low modulus, flexible catheter has a diameter in a range of about 0.5-2 mm.

19. The optoelectronic system of claim 1, wherein the optoelectronic probe is a catheter-type oximetry sensor.

20. The optoelectronic system of claim 1, wherein the optoelectronic probe further comprises sensors for measuring pressure and flow, and/or means for drug delivery.

* * * * *